United States Patent
Mumm et al.

(10) Patent No.: US 10,010,588 B2
(45) Date of Patent: Jul. 3, 2018

(54) METHODS OF USING PEGYLATED INTERLEUKIN-10 FOR TREATING HYPERLIPIDEMIA

(71) Applicant: ARMO BioSciences, Inc., Redwood City, CA (US)

(72) Inventors: John Brian Mumm, Los Altos Hills, CA (US); Ivan Ho Chan, Redwood City, CA (US)

(73) Assignee: ARMO BioSciences, Inc., Redwood City, CA (US)

( * ) Notice: Subject to any disclaimer, the term of this patent is extended or adjusted under 35 U.S.C. 154(b) by 0 days.

(21) Appl. No.: 14/908,992

(22) PCT Filed: Aug. 26, 2014

(86) PCT No.: PCT/US2014/052638
§ 371 (c)(1),
(2) Date: Jan. 29, 2016

(87) PCT Pub. No.: WO2015/031316
PCT Pub. Date: Mar. 5, 2015

(65) Prior Publication Data
US 2016/0193300 A1 Jul. 7, 2016

Related U.S. Application Data

(60) Provisional application No. 61/872,394, filed on Aug. 30, 2013.

(51) Int. Cl.
| | | |
|---|---|---|
| *A61K 38/20* | (2006.01) | |
| *A61K 45/06* | (2006.01) | |
| *A61K 31/397* | (2006.01) | |
| *A61K 31/455* | (2006.01) | |

(52) U.S. Cl.
CPC ........ *A61K 38/2066* (2013.01); *A61K 31/397* (2013.01); *A61K 31/455* (2013.01); *A61K 45/06* (2013.01); *C07K 2319/00* (2013.01)

(58) Field of Classification Search
None
See application file for complete search history.

(56) References Cited

U.S. PATENT DOCUMENTS

| | | |
|---|---|---|
| 5,231,012 A | 7/1993 | Mosmann et al. |
| 5,252,714 A | 10/1993 | Harris et al. |
| 5,328,989 A | 7/1994 | Vellekamp et al. |
| 5,624,823 A | 4/1997 | Sachs et al. |
| 5,643,575 A | 7/1997 | Martinez et al. |
| 5,665,345 A | 9/1997 | Yarchoan et al. |
| 5,710,251 A | 1/1998 | Vellekamp et al. |
| 5,824,784 A | 10/1998 | Kinstler et al. |
| 5,866,134 A | 2/1999 | Fine et al. |
| 5,876,969 A | 3/1999 | Fleer et al. |
| 5,908,621 A | 6/1999 | Glue et al. |
| 5,919,455 A | 7/1999 | Greenwald et al. |
| 5,932,462 A | 8/1999 | Harris et al. |
| 5,945,097 A | 8/1999 | Cutler |
| 5,951,974 A | 9/1999 | Gilbert et al. |
| 5,985,263 A | 11/1999 | Lee et al. |
| 5,985,265 A | 11/1999 | Kinstler et al. |
| 5,985,857 A | 11/1999 | Kinstler et al. |
| 5,989,867 A | 11/1999 | Knappe et al. |
| 6,217,857 B1 | 4/2001 | Mosmann et al. |
| 6,387,364 B1 | 5/2002 | Fersuson |
| 6,428,985 B1 | 8/2002 | Bromberg et al. |
| 6,660,258 B1 | 12/2003 | Tovey |
| 6,685,931 B1 | 2/2004 | Grint et al. |
| 6,770,272 B2 | 8/2004 | Strom et al. |
| 6,989,377 B2 | 1/2006 | Hayes et al. |
| 7,052,684 B2 | 5/2006 | Ferguson |
| 7,052,686 B2 | 5/2006 | Lee et al. |
| 7,056,701 B2 | 6/2006 | Fleer et al. |
| 7,261,882 B2 | 8/2007 | Watkins |

(Continued)

FOREIGN PATENT DOCUMENTS

| | | |
|---|---|---|
| CN | 1760209 | 10/2004 |
| CN | 102145178 | 8/2011 |

(Continued)

OTHER PUBLICATIONS

Anonymous, online publication titled "Blood volume calculator" by EasySurf (hereinafter "EasySurf") (available on the Internet URL: https://web.archive.org/web/20121001142649/http://www.easysurf.cc/cnver22.htm) (Sep. 23, 2012—accessed Nov. 21, 2016).*
R&D systems-Rec. human IL-10 Protein—https:/lwww.rndsystems.com/products/recom bi nant-human-il-1O-protein-cf_217-i l-cf. accessed Feb. 22, 2016.*
R&D systems-Rec. mouse IL-10 Protein—https:/lwww.rndsystems.com/products/recom bi nant-mouse-il-10-protein _417-ml. accessed Feb. 22, 2016.*
Accession NP_036986.2; GI 148747382; Aug. 10, 2014.
Accession NP_776513.1; GI 41386772; Jan. 4, 2015.
Accession NP_001009327.1; GI 57164347; Feb. 13, 2011.
Accession ABY86619.1; GI 166244598 ; Feb. 4, 2008.
Accession AAC23839.1; GI 3242896; Jun. 8, 2000.

(Continued)

*Primary Examiner* — Elly-Gerald Stoica
(74) *Attorney, Agent, or Firm* — Carol L. Francis; Bozicevic, Field & Francis LLP

(57) ABSTRACT

Methods of treating subjects having diseases, disorders, or conditions, including disorders associated with cholesterol homeostasis, responsive to IL-10, including methods of administration and dosing regimens associated therewith, are provided, More particularly, the present disclosure relates to optimized dosing parameters to achieve and maintain efficacy in the treatment and/or prevention of metabolic diseases, disorders and conditions in a subject, while minimizing the adverse effects associated therewith. Particular embodiments are directed to the treatment and/or prevention of abnormally high levels of cholesterol and/or manifestation(s) of hypercholesterolemia in as subject.

15 Claims, 11 Drawing Sheets

(56) References Cited

U.S. PATENT DOCUMENTS

| | | | |
|---|---|---|---|
| 7,611,700 B2 | 12/2009 | Gantier et al. | |
| 7,650,243 B2 | 1/2010 | Gantier et al. | |
| 7,666,400 B2 | 2/2010 | Chang et al. | |
| 7,749,490 B2 | 7/2010 | Sommer et al. | |
| 7,939,056 B2 | 5/2011 | Horwitz et al. | |
| 8,044,175 B2 | 10/2011 | Dransfield et al. | |
| 8,067,532 B2 | 11/2011 | MacLean | |
| 8,618,256 B2 | 12/2013 | Cox | |
| 2002/0044921 A1* | 4/2002 | Lee | C07K 14/5428 424/85.2 |
| 2003/0012775 A1 | 1/2003 | Brandt et al. | |
| 2003/0186386 A1 | 10/2003 | Hansen et al. | |
| 2004/0101965 A1 | 5/2004 | Griesenbach et al. | |
| 2004/0213795 A1 | 10/2004 | Collins et al. | |
| 2005/0008615 A1 | 1/2005 | Bam et al. | |
| 2005/0260767 A1 | 11/2005 | Clerici et al. | |
| 2006/0046961 A1 | 3/2006 | McKay et al. | |
| 2006/0210534 A1 | 9/2006 | Lee et al. | |
| 2006/0258607 A1 | 11/2006 | Jarosch et al. | |
| 2007/0134197 A1 | 6/2007 | Eichner et al. | |
| 2008/0058246 A1 | 3/2008 | Bhaskaran et al. | |
| 2008/0069797 A1 | 3/2008 | Roncarolo et al. | |
| 2008/0081031 A1 | 4/2008 | Oft et al. | |
| 2008/0096252 A1 | 4/2008 | Zamonst et al. | |
| 2009/0035256 A1 | 2/2009 | Sommer et al. | |
| 2009/0214463 A1 | 8/2009 | Slobedman et al. | |
| 2009/0214471 A1 | 8/2009 | Oft et al. | |
| 2009/0311187 A1 | 12/2009 | Berman et al. | |
| 2010/0068147 A1 | 3/2010 | Hibberd et al. | |
| 2010/0111898 A1 | 5/2010 | Pelura | |
| 2010/0129386 A1 | 5/2010 | Elson et al. | |
| 2010/0255496 A1 | 10/2010 | Schrader et al. | |
| 2010/0266532 A1 | 10/2010 | Ferguson | |
| 2010/0297070 A1 | 11/2010 | Dugan et al. | |
| 2011/0064690 A1 | 3/2011 | Lee et al. | |
| 2011/0091419 A1 | 4/2011 | Oft et al. | |
| 2011/0250163 A1 | 10/2011 | Blaisdell et al. | |
| 2011/0275123 A1 | 11/2011 | Paciotti et al. | |
| 2011/0305665 A1 | 12/2011 | Lee et al. | |
| 2011/0312010 A1 | 12/2011 | Manuilov | |
| 2012/0003221 A1 | 1/2012 | McDonagh et al. | |
| 2012/0115926 A1 | 5/2012 | Geary et al. | |
| 2012/0213793 A1 | 8/2012 | Huang et al. | |
| 2012/0252742 A1 | 10/2012 | Kranz et al. | |
| 2012/0270899 A1 | 10/2012 | Bannister et al. | |
| 2012/0321617 A1 | 12/2012 | Osterroth et al. | |
| 2013/0156774 A1 | 6/2013 | Kuchroo et al. | |
| 2014/0199750 A1 | 7/2014 | Weng et al. | |
| 2014/0256626 A1 | 9/2014 | Santi et al. | |
| 2014/0314795 A1 | 10/2014 | Riddell et al. | |
| 2014/0349402 A1 | 11/2014 | Cooper et al. | |
| 2015/0038678 A1 | 2/2015 | Eaton et al. | |
| 2015/0118244 A1 | 4/2015 | Shahabi et al. | |
| 2016/0340406 A1 | 11/2016 | Zhao et al. | |
| 2016/0361415 A1 | 12/2016 | Mumm et al. | |
| 2016/0375101 A1 | 12/2016 | Oft | |

FOREIGN PATENT DOCUMENTS

| | | |
|---|---|---|
| EP | 0251304 | 1/1988 |
| EP | 2066336 | 9/2012 |
| WO | WO 92/012725 | 8/1992 |
| WO | WO 92/012726 | 8/1992 |
| WO | 199404180 | 3/1994 |
| WO | 199417773 | 8/1994 |
| WO | 1995/03411 | 2/1995 |
| WO | 199503411 | 2/1995 |
| WO | WO 95/006058 | 3/1995 |
| WO | WO 95/019780 | 7/1995 |
| WO | WO 96/011953 | 4/1996 |
| WO | WO 97/003690 | 2/1997 |
| WO | WO 99/032134 | 7/1999 |
| WO | 200037096 | 6/2000 |
| WO | WO 01/005821 | 1/2001 |
| WO | WO 01/058950 | 8/2001 |
| WO | WO 02/026265 | 4/2002 |
| WO | WO 04/044006 | 5/2004 |
| WO | 2004060300 | 7/2004 |
| WO | WO 04/056850 | 7/2004 |
| WO | 2004106486 | 12/2004 |
| WO | WO 06/075138 | 7/2006 |
| WO | WO 06/119170 | 11/2006 |
| WO | 2006130580 | 12/2006 |
| WO | 2007139178 | 6/2007 |
| WO | WO 08/054585 | 5/2008 |
| WO | WO 09/016043 | 2/2009 |
| WO | 2009036568 | 3/2009 |
| WO | 2010022227 | 2/2010 |
| WO | WO 10/077853 | 7/2010 |
| WO | WO 11/051489 | 5/2011 |
| WO | 2011064399 | 6/2011 |
| WO | WO 12/004384 | 1/2012 |
| WO | WO 12/050923 | 4/2012 |
| WO | WO 12/050930 | 4/2012 |
| WO | 2012056251 | 5/2012 |
| WO | WO 13/113008 | 8/2013 |
| WO | 2013130913 | 9/2013 |
| WO | 2014172392 | 10/2014 |
| WO | 2015070060 | 5/2015 |
| WO | 2015153753 | 10/2015 |

OTHER PUBLICATIONS

"Guidance for Industry Immunogenicity Assessment for Therapeutic Protein Products," (2013) *FDA Guidances*.
"Highlights of Prescribing Information," (1997) *Rituxan*.
Recombinant Human IL-1 0 Protein, CF R&D Systems, accessed Feb. 22, 2016.
Recombinant Mouse I L -1 0 Protein R&D Systems, accessed Feb. 22, 2016.
Agata et al. (1996) "Expression of the PD-1 antigen on the surface of stimulated mouse T and B lymphocytes," *Int Immunol*; 8(5):765-772.
Aggen (2010) "Engineering Human Single-Chain T Cell Receptors," *Dissertation*; http://hdl.handle.net/2142/18585.
Alvarez et al. (2012) "Effects of PEGylation and Immune Complex Formation on the Pharmacokinetics and Biodistribution of Recombinant Interleukin10 in Mice," *Drug Metab Dispos*; 40(2):360-373.
Ansari and Raghava (2010) "Identification of conformational B-cell Epitopes in an antigen from its primary sequence," *Immunome Res*; 6:9pgs.
Ansell et al. (2002) "Phase 1 study of interleukin-12 in combination with rituximab in patients with B-cell non-Hodgkin lymphoma," *Blood*; 99:67-74.
Arakawa and Tsumoto (2003) "The effects of arginine on refolding of aggregated proteins: not facilitate refolding, but suppress aggregation," *Biochemical and Biophysical Research Communications*; 304:148-152.
Armstrong et al. (1996) "Interleukin 10 (IL-10) regulation of tumour necrosis factor cx (TNF-cx) from human alveolar macrophages and peripheral blood monocytes," *Thorax*; 51:143-149.
Asadullah et al. (1999) "Interleukin 10 Treatment of Psoriasis," *Arch Dermatol.*; 135-187-192.
Asadullah et al. (2003) "Interleukin 10 Therapy—Review of a New Approach," *Pharmacol. Rev.*; 55-241-269.
Bajetta et al. (1998) "Pilot Study of Subcutaneous Recombinant Human Interleukin 12 in Metastatic Melanoma," *Clinical Cancer Research*; 4:75-85.
Banerjee et al. (2012) "Poly(ethylene glycol)-Prodrug Conjugates: Concept, Design, and Applications," *Journal of Drug Delivery*; Article ID 103973:17 pages.
Bea at al. (2011) "Performance Evaluation of a Multiplex Assay for Future Use in Biomarker Discovery Efforts to Predict Body Composition," *Clin Chem Lab Med.*; 49(5):817-824.
Berger et al. (2009) "Safety and immunologic effects of IL-15 administration in nonhuman primates," *Blood*; 114:2417-2426.
Berman et al. (1996) "Systemic administration of cellular IL-10 induces an effective, specific, and long-lived immune response against established tumors in mice," *J Immunol*; 157:231-238.

(56) References Cited

OTHER PUBLICATIONS

Bilzer et al. (2006) "Role of Kupffer cells in host defense and liver disease," *Liver International*; 26:1175-1186.

Biswas et al. (2007) "Pathogen_specific CD8 T Cell Responses Are Directly Inhibited by IL-10," *J Immunol.*; 179:4520-4528.

Brady et al. (1994) "Reflections on a peptide," *Nature*; 368:692-693.

Brooks et al. (2008) "IL-10 and PD-L1 operate through distinct pathways to suppress T-cell activity during persistent viral infection," *PNAS*; 105(51):20428-20433.

Burgess (2009) "Refolding Solubilized Inclusion Body Proteins," *Methods in Enzymology*; 463:259-282.

Cai et al. (1999) "IL-10 enhances NK cell proliferation, cytotoxicity and production of IFN-q when combined with IL-18," *Eur. J. Immunol.*; 29:2658-2665.

Caliceti et al. (2012) "Effect of Plasma Membrane Cholesterol Depletion on Glucose Transport Regulation in Leukemia Cells," *PLoS One*; 7:e41246.

Cannistra & Niloff (1996) "Cancer of the uterine cervix," *New Eng I J Med* 334:1030-1038.

Cao et al. (2011) "Janus kinase activation by cytokine oncostatin M decreases PCSK9 expression in liver cells," *J Lipid Res.*; 52(3):513-530.

Capitini et al. (2009) "Modulating T cell Homeostasis with IL-7: Preclinical and Clinical Studies," *J Intern Med*; 266(2):141-153.

Cebon et al. (2003) "Two phase I studies of low dose recombinant human IL-12 with Melan-A and influenza peptides in subjects with advanced malignant melanoma," *Cancer Immunity*; 3:7 (18 pages).

Chamow et al. (1994) "Modification of CD4 Immunoadhesin with Monomethoxypoly(ethylene glycol) Aldehyde via Reductive Alkylation," *Bioconjugate Chern.*; 5:133-140.

Chan et al. (2015) "The Potentiation of IFN-γ and Induction of Cytotoxic Proteins by Pegylated IL-10 in Human CD8 T Cells," *J Interferon Cytokine Res*; 35(12):948-955.

Chen & Zlotnik (1991) "IL-10: a novel cytotoxic T cell differentiation factor," *J Immunol*; 147:528-534.

Chen et al. (2007) "Prediction of linear B-cell epitopes using amino acid pair antigenicity scale," *Amino Acids*; 33:423-428.

Choi et al. (2006) "Serum adiponectin, interleukin-10 levels and inflammatory markers in the metabolic 1-18 syndrome," *Diabetes Research and Clinical Practice*; 75:235-240.

Collins et al. (2012) "Trastuzumab induces antibody-dependent cellmediated cytotoxicity (ADCC) in HER-2-non-amplified breast cancer cell lines," *Annals of Oncology*; 23:1788-1795.

Compton et al. (2004) "Pathogenesis of Enterotropic Mouse Hepatitis Virus in Immunocompetent and Immunodeficient Mice," *Comparative Medicine*; 54(6):681-689.

Conlon et al. (2014) "Redistribution, Hyperproliferation, Activation of Natural Killer Cells and CDS T Cells, and Cytokine Production During First-in-Human Clinical Trial of Recombinant Human Interleukin-15 in Patients With Cancer," *Journal of Clinical Oncology*; 33(1):74-82.

Couder et al. (1993) "Synthesis and biological activities of φ(CH2NH) pseudopeptide analogues of the C-terminal hexapeptide of neurotensin," *Int. J. Peptide Protein Res.*; 41:181-184.

D'Andrea et al. (1993) "Interleukin 10 (IL-10) Inhibits Human Lymphocyte Interferon 3,-Production by Suppressing Natural Killer Cell Stimulatory Factor/IL-12 Synthesis in Accessory Cells," *J. Exp. Med*; 178:1041-1048.

Das et al. (2012) "IL-10-Producing Regulatory B Cells in the Pathogenesis of Chronic Hepatitis B Virus Infection," *J. Immunol.*; 189(8):3925-3935.

Davidson & Diamond (2001) "Autoimmune diseases," *New Engl J Med*; 345:340-350.

De Waal Malefyt et al. (1991) "Interleukin 10 (IL-10) and viral IL-10 strongly reduce antigen-specific human T cell proliferation by diminishing the antigen-presenting capacity of monocytes via downregulation of class II major histocompatibility complex expression," *J Exp Med*; 174(4):915-924.

De Waal Malefyt et al. (1991) "Interleukin 10(IL-10) Inhibits Cytokine Synthesis by Human Monocytes: An Autoregulatory Role of IL-10 Produced by Monocytes," *J. Exp. Med*; 174:1209-1220.

Devay et al. (2013) "Characterization of Proprotein Convertase Subtilisin/Kexin Type 9 (PCSK9) Trafficking Reveals a Novel Lysosomal Targeting Mechanism via Amyloid Precursor-like Protein 2 (APLP2)," *J. Biol. Chem.*; 288:10805-10818.

Dolgin (2011) "Trial puts niacin—and cholesterol dogma—in the line of fire," *Natue Medicine*; 17(7):356.

Dorner et al. (2011) "A genetically humanized mouse model for hepatitis C virus infection," *Nature*; 474:208-211.

Easy Surf. Blood Volume Calculator [online]Oct. 1, 2012 [retrieved Aug. 18, 2014]. Available on the internet: <URL: https://web.archive.org/web/20121 001142649/http://www.easysurf.cc/cnver22.htm >.

Ehrilich et al. (2013) "Preparation and Characterization of Albumin Conjugates of a Truncated Peptide YY Analogue for Half-Life Extension," *Bioconjug. Chem.*; 24(12):2015-2024.

El-Manzalawy et al. (2008) "Predicting linear B-cell epitopes using string kernels," *J Mol Recognit*; 21:243-255.

Emmerich et al. (2012) "IL-10 directly activates and expands tumor-resident CD8(+) T cells without de novo infiltration from secondary lymphoid organs," *Cancer Res*; 72(14):3570-3581.

Engel et al. (2006) "Using Endoproteinases Asp-N and Glu-C to Improve Protein Characterization," *Promega Corporation*; 10$^{th}$ edition.

Enzinger & Mayer (2003) "Esophageal cancer," *New Eng I J Med*; 349:2241-2252.

Fahnert et al. (2012) "Using Folding Promoting Agents in Recombinant Protein Production: A Review," *Methods inn Molecular Biology*; 824:3-36.

Fang et al. (2015) "Programmed Death 1 (PD-1) is involved in the development of proliferative diabetic retinopathy by mediating activation-induced apoptosis," *Mol Vis*; 21:901-910.

Farrar et al. (1999) "Cancer dormancy. VII. A regulatory role for COB+ T cells and IFN-gamma in establishing and maintaining the tumor-dormant state," *J Imunol* 162:2842-2849.

Fehniger and Caligiuri (2001) "Interleukin 15: biology and relevance to human disease," *Blood*; 97:14-32.

Feingold et al. (1996) "Endotoxin, TNF, and IL-I decrease cholesterol 7a-hydroxylase mRNA levels and activity," *Journ of Lipid Res*; 37:223-228.

Fiorentino et al. (1989) "Two types of mouse T helper cell. IV. Th2 clones secrete a factor that inhibits cytokine production by Th1 clones," *J Exp Med*; 170:2081-2095.

Forastiere et al. (2001) "Head and neck cancer," *New Engl J Med* 345:1890-1900.

Fridman et al. (2012) "The immune contexture in human tumours: impact on clinical outcome," *Nature*; 12:298-306.

Fry and Mackall (2002) "Interleukin-7: from bench to clinic," *Blood*; 99:3892-3904.

Fujiwara et al. (2010) "Extraction and purification of human interleukin-10 from transgenic rice seeds," *Protein Expression and Purification*; 72:125-130.

Galon et al. (2013) "The Continuum of Cancer Immunosurveillance: Prognostic, Predictive, and Mechanistic Signatures," *Immunity*; 39:11-26.

Gameren et al. (1994) "Effects of Recombinant human interleukin-6 in cancer patients: a phase I-II study," *Blood*; 84:1434-1441.

Gao et al. (2012) "BEST: Improved Prediction of B-Cell Epitopes from Antigen Sequences," *PLoS ONE*; 7(6): e40104.

GenBank Accession No. M37897 "Mouse interleukin 10 mRNA, complete cds," dated Apr. 27, 1993.

GenBank Accession No. NP 000563 "interleukin-10 precursor [*Homo sapiens*]," dated Mar. 3, 1995.

Georgescu et al. (1997) "Interleukin-10 Promotes Activation-induced Cell Death of SLE Lymphocytes Mediated by Fas Ligand," *J. Clin. Invest.*; 100:2622-2633.

Gerstein et al. (2008) "Effects of Intensive Glucose Lowering in Type 2 Diabetes," *New England J of Medicine*; 358(24):2545-2559.

Gesser et al. (1997) "Identification of functional domains on human interleukin 10," *Proc. Natl. Acad. Sci.*; 94:14620-14625.

(56) References Cited

OTHER PUBLICATIONS

Gierens et al. (2000) "Interleukin-6 Stimulates LDL Receptor Gene Expression via Activation of Sterol-Responsive and Sp1 Binding Elements," *Arterioscler Thromb Vasc Biol.*; 20:1777-1783.
Gregoriadis et al., (2005) "Improving the therapeutic efficacy of peptides and proteins: A role for polysialic acids," *Int. J. Pharmaceutics*; 300(1-2):125-130.
Groux et al. (1998) "A transgenic model to analyze the immunoregulatory role of IL-10 secreted by antigen- presenting cells," *J Immunol*; 162:1723-1729.
Groux et al. (1998) "Inhibitory and stimulatory effects of IL-10 on human COB+ T cells," *J Immunol*; 160:3188-3193.
Hagenbaugh et al. (1997) "Altered immune responses in interleukin 10 transgenic mice," *J Exp Med*; 185:2101-2110.
Hamada et al. (2009) "Effect of Additives on Protein Aggregation," *Current Pharm Biotech*; 10:400-407.
Hashizume et al. (2010) "Overproduced interleukin 6 decreases blood lipid levels via upregulation of very-low-density lipoprotein receptor," *Ann Rheum Dis*; 69:741-746.
Heeschen et al. (2003) "Serum Level of the Antiinflammatory Cytokine Interleukin-1 0 Is an Important Prognostic Determinant in Patients With Acute Coronary Syndromes," *Circulation*; 107:2109-2114.
Hombach et al. (2013) "Arming Cytokine-induced Killer Cells With Chimeric Antigen Receptors: CD28 Outperforms Combined CD28-OX40 'Super-stimulation'," *Molecular Therapy*; 12:2268-2277.
Howard et al. (1993) "Interleukin 10 Protects Mice from Lethal Endotoxemia," *J. Exp. Med.*; 177:1205-1208.
Huang et al. (1996) "Interleukin 10 Suppresses Tumor Growth and Metastasis of Human Melanoma Cells: Potential Inhibition of Angiogenesis," Clinical Cancer Research, *The American Assn for Cancer Research*; 2(12):1969-1979.
Huang et al. (2010) "Depletion of Liver Kupffer Cells Prevents the Development of Diet-Induced Hepatic Steatosis and Insulin Resistance," 59:347-357.
Huntington et al. (2008) "IL-15 trans-presentation promotes human NK cell development and diff erentiation in vivo," *J. Exp. Med.*; 206:25-34.
Hustoft et al. (2012) "A Critical Review of Trypsin Digestion for LC-MS Based Proteomics," *InTech*; Chapter 4.
Infante et al. (2015) "A first-in-human dose escalation study of PEGylated recombinant human IL-10 (AM0010) in advanced solid tumors," *ASCO Meeting Abstracts*; 33(15 suppl):3017.
International Search Report; PCT/US01/42431, dated Aug. 20, 2002.
Ishikawa et al. (2005) "Interleukin-10 plasmid DNA inhibits liver and lung metastasis of Colon 26 adenocarcinoma in mice," *Proceedings of the Annual Meeting, American Association for Cancer Research*; vol. 46, Abstract # 3364.
Izbicki et al. (1997) "Prognostic value of immunohistochemically identifiable tumor cells in lymph nodes of patients with completely resected esophageal cancer," *New Engl J Med*; 337:1188-1194.
Jameson et al. (1994) "A rationally designed CD4 analogue inhibits experimental allergic encephalomyelitis," *Nature*; 368:744-746.
Jevševar et al. (2010) "PEGylation of therapeutic proteins," *Biotechnol. J.*; 5:113-128.
Jiang et al. (2015) "T-cell exhaustion in the tumor microenvironment," *Cell Death Dis*; 6:e1792.
Josephson et al. (2001) "Crystal Structure of the IL-10/IL-10R1 Complex Reveals a Shared Receptor Binding Site," *Immunity*; 14:35-46.
Jungbauer et al. (2007) "Current status of Technical protein refolding," *Journal of Biotechnology*; 128:587-596.
Katre (1993) "The Conjugation of Proteins with Polyethylene Glycol and Other Polymers Altering Properties of Proteins to Enhance their Therapeutic Potential," *Advanced Drug Delivery Reviews*; 10(1):91-114.
Khow and Suntrarachun (2012) "Strategies for production of active eukaryotic proteins in bacterial expression system," *Asian Pac. J. Biomed.*; 2(2):159-162.

Kimball et al (2002) "Clinical and Immunologic Assessment of Patients With Psoriasis in a Randomized, Double-blind, Placebo-Controlled Trial Using Recombinant Human Interleukin 10," *Arch Dermatol*; 138:1341-1346.
Kinstler et al. (1996) "Characterization and Stability of N-terminally PEGylated rhG-CSF," *Pharm. Res.*; 13:996-1002.
Kinstler et al. (2002) "Mono-N-terminal poly(ethylene glycol)-protein conjugates," *Advanced Drug Delivery Reviews*; 54:477-485.
Klompus et al. (2008) "A simple novel method for the preparation of noncovalent homodimeric, biologically active human interleukin 10 in *Escherichia coli*—Enhancing protein expression by degenerate PCR of 59 DNA in the open reading frame," *Protein Expression and Purification*; 62:199-205.
Kokura et al. (2003) "The blocking of NFkB activation by systemicinterleukin-10 gene therapy inhibits liver and lung metastasis of colon 26 adenocarcinoma in mice" *Gastroenterology*; 124(4): Abstract No. W965.
Kokura et al. (2005) "Interleukin-1 0 plasmid DNA inhibits subcutaneous tumor growth of Colon adenocarcinoma in mice," *Cancer Letters*; 218:171-179.
Kong et al. (2005) "In vivo activities of cytokine oncostatin M in the regulation of plasma lipid levels," *Journal of Lipid Research*; 46:1163-1171.
Körholz et al. (1997) "The Role of Interleukin-10 (IL-10) in IL-15—Mediated T-Cell Responses," *Blood*; 90(11):4513-4521.
Kundu et al. (1996) "Antimetastatic and antitumor activities of interleukin 10 in a murine model of breast cancer," *J Nail Cancer Inst*; 88:536-541.
Kundu et al. (1997) "Interleukin-10 inhibits tumor metastasis, down regulates MHC class I, enhances NK lysis," *Cellular Immunology, Academic Press*; 180(1):55-61.
Kute et al. (2012) "Understanding key assay parameters that affect measurements of trastuzumab-mediated ADCC against Her2 positive breast cancer cells," *OncoImmunology*; 1(6):810-821.
Langowski et al. (2006) "IL-23 promotes tumour incidence and growth," *Nature*; 442:461-465.
Lasek et al. (2014) "Interleukin 12: still a promising candidate for tumor immunotherapy?" *Cancer Immunol Immunother*; 63:419-435.
Le et al. (2001) "Pre-existing tumor-sensitized T cells are essential for eradication of established tumors by IL-12 and cyclophosphamide plus IL-12," *J Immunol*; 167:6765-6772.
Lehmann et al. (2014) "IL-12 Directs Further Maturation of Ex Vivo Differentiated NK Cells with Improved Therapeutic Potential," *PLoS One*; 9(1):e87131 (12 pages).
Lewington and Clark (2005) "Combined Effects of Systolic Blood Pressure and Total Cholesterol on Cardiovascular Disease Risk," *Circulation*; 112:3373-3374.
Lindhout et al. (2011) "Site-specific enzymatic polysialylation of therapeutic proteins using bacterial enzymes," *PNAS*; 108(18)7397-7402.
Liu et al. (2003) "IL-10 Mediates Suppression of the CD8 T Cell IFN-γ Response to a Novel Viral Epitope in a Primed Host," *J Immunol*; 171:4765-4772.
Loebbermann et al. (2012) "IL-10 Regulates Viral Lung Immunopathology during Acute Respiratory Syncytial Virus Infection in Mice," *PLoS ONE*; 7(2):e32371.
Lopez et al. (2005) "IL-12 and IL-10 Expression Synergize to Induce the Immune-Mediated Eradication of Established Colon and Mammary Tumors and Lung Metastasis," *J Immunol*; 175:5885-5894.
Lowe et al. (1998) "Impact of Major Cardiovascular Disease Risk Factors, Particularly in Combination, on 22-Year Mortality in Women and Men," *Arch Intern Med*; 158:2007-2014.
Lu et al. (2004) "Prognostic factors in resected stage I non-small-cell lung cancer: a multivariate analysis of six molecular markers," *J Clin Oneal*; 22:4575-4583.
Lugli et al. (2010) "Transient and persistent effects of IL-15 on lymphocyte homeostasis in nonhuman primates," *Blood*; 116:3238-3248.
Lynch and Chapelle (2003) "Hereditary colorectal cancer," *New Eng I J Med*; 348:919-932.

(56) References Cited

OTHER PUBLICATIONS

Martin et al. (2001) "B-Cell Deficiency Suppresses Vaccine-Induced Protection against Murine Filariasis but Does Not Increase the Recovery Rate for Primary Infection," *Infect. Immun.*; 69(11):7067-7073.
Mattos et al. (2012) "PEGylation of interleukin-10 improves the pharmacokinetic profile and enhances the antifibrotic effectivity in CCl.-induced fibrogenesis in mice," *J Control Release*; 162(1):84-91.
Maus et al. (2014) "Antibody-modified T cells: CARs take the front seat for hematologic malignancies," *Blood*; 123(17):2625-2635.
Miki Toyokazu et al. (2000) "Anti-metastatic effect of IL-10 gene modification in human lung cancer cells is differentially regulated by organ microenvironments," *Proceedings of the Annual Meeting American Association for Cancer Research*; 41:3.
Monk (2011) "A Strategy for the Quantification of Protein Polyethylene Glycol (PEG) Derivatized Sites using iTRAQ," *University of California*, San Diego; 1-51.
Moore et al. (1990) "Homology of cytokine synthesis inhibitory factor (IL-10) to the Epstein-Barr virus gene BCRFI," *Science*; 248:1230-1234.
Moran et al. (1994) "Human leukemia inhibitory factor inhibits development of experimental atherosclerosis," *Arterioscler Thromb Vasc Biol.*; 14(8):1356-1363.
Motzer et al. (2001) "Randomized Multicenter Phase II Trial of Subcutaneous Recombinant Human Interleukin-12 Versus Interferon-α2a for Patients with Advanced Renal Cell Carcinoma," *Journal of Interferon and Cytokine Research*; 21:257-263.
Mumm et al. (2011) "IL-10 elicits IFNγ-dependent tumor immune surveillance," *Cancer Cell*; 20(6):781-796.
Naicker et al. (2009) "Interleukin-10 Promoter Polymorphisms Influence HIV-1 Susceptibility and Primary HIV-1 Pathogenesis," *J. Infect. Dis.*; 200(3):448-452.
Natsume et al. (2009) "Improving effector functions of antibodies for cancer treatment: Enhancing ADCC and CDC," *Drug Design, Development and Therapy*; 3:7-16.
Nenseter et al. (1992) "Role of liver endothelial and Kupffer cells in clearing low density lipoprotein from blood in hypercholesterolemic rabbits," *J of Lipid Res*; 33:867-877.
Neven et al. (2013) "A Mendelian predisposition to B cell lymphoma caused by IL-10R deficiency," *Blood*; 122(23):3712-3722.
Neyrinck et al. (2009) "Critical role of Kupffer cells in the management of diet-induced diabetes and obesity," *Biochemical and Biophysical Research Communications*; 385:351-356.
Nicholls et al. (2012) "Is niacin ineffective? or did AIM-HIGH miss its target?," *Cleveland Clinic Journ of Med*; 79(1):38-43.
Noguchi et al. (2003) "PDX-1 Protein Containing Its Own Antennapedia-Like Protein Transduction Domain Can Transduce Pancreatic Duct and Islet Cells," *Diabetes*; 52(7):1732-1737.
Osaki et al. (1999) "Potent antitumor effects mediated by local expression of the mature form of the interferon-γ inducing factor, interleukin-18 (IL-18)," *Gene Therapy*; 6:808-815.
Osborne (1998) "Tamoxifen in the treatment of breast cancer," *New Engl J Med*; 339:1609-1618.
Overdijk et al. (2011) "Epidermal Growth Factor Receptor (EGFR) Antibody-Induced Antibody-Dependent Cellular Cytotoxicity Plays a Prominent Role in Inhibiting Tumorigenesis, Even of Tumor Cells Insensitive to EGFR Signaling Inhibition," *Journal of Immunology*; 187:3383-3390.
Pardoll (2012) "The blockade of immune checkpoints in cancer immunotherapy," *Cancer*; 12:252-264.
Park et al. (2011) "IL-15-Induced IL-10 Increases the Cytolytic Activity of Human Natural Killer Cells," *Mol. Cells*; 32:265-272.
Pasut and Veronese (2012) "State of the art in PEGylation: The great versatility achieved after forty years of research," *Journal of Controlled Release*; 161:461-472.
Payne et al. (2010) "Product development issues for PEGylated proteins," *Pharmaceutical Development and Technology*; 16:423-440.
Pegram et al. (2012) "Interleukin 12: Stumbling Blocks and Stepping Stones to Effective Anti-Tumor Therapy," *Advancements in Tumor Immunotherapy and Cancer Vaccines*; Chapter 10:197-218.
Pellegrini et al. (2011) "IL-7 Engages Multiple Mechanisms to Overcome Chronic Viral Infection and Limit Organ Pathology," *Cell*; 144:1-13.
Pettit et al. (1997) "Structure-Function Studies of Interleukin 15 using Site-specific Mutagenesis, Polyethylene Glycol Conjugation, and Homology Modeling," *J. Biol. Chem.* 272:2312-2318.
Rachmawati et al. (2004) "Pharmacokinetic and Biodistribution Profile of Recombinant Human Interleukin-10 Following Intravenous Administration in Rats with Extensive Liver Fibrosis," *Pharm. Res.*; 21(11):2072-2078.
Rachmawati et al. (2007) "Chemical Modification of Interleukin-10 with Mannose 6-Phosphate Groups Yields a Liver-Selective Cytokine," *Drug Metabolism and Disposition*; 35(5):814-821.
Radwanski et al. (1998) "Pharmacokinetics and Leukocyte Responses of Recombinant Human Interleukin-10," *Pharm. Res.*; 15(12):1895-1901.
Ramirez-Montagut et al. (2003) "Immunity to melanoma: unraveling the relation of tumor immunity and autoimmunity," *Oncogene*; 22:3180-3187.
Re et al. (2002) "Preclinical evaluation of the antiproliferative potential of STI571 in Hodgkin's disease," *British Journal of Cancer*; 86:1333-1335.
Reynolds, et al. (2002) "Proteolytic 18O Labeling for Comparative Proteomics: Evaluation of Endoprotease Glu-C as the Catalytic Agent," *Journal of Proteome Research*; 1(1):27-33.
Roberts et al. (2012) "Chemistry for peptide and protein PEGylation," *Advanced Drug Delivery Reviews*; 64:116-127.
Rolfe et al. (2003) "Leukaemia inhibitory factor retards the progression of atherosclerosis," *Cardiovascular Research*; 58:222-230.
Russo et al. (2006) "Randomized trial of pegylated interferon a-2b monotherapy in haemodialysis patients with chronic hepatitis C," *Nephrol Dial Transplant*; 21:437-443.
Saha and Raghava (2006) "Prediction of continuous B-cell epitopes in an antigen using recurrent neural network," *Proteins*; 65:40-48.
Sakamoto et al. (2003) "Interleukin-10 gene therapy enhances antitumor effect of CPT-11 for lung metastasis of colon26 adenocarcinoma in mice," *Gastroenterology*; 124(4):A456-A457.
Sawaya et al. (2003) "Risk of cervical cancer associated with extending the interval between cervical-cancer screenings," *New Engl J Med*; 349:1501-1509.
Schäffner et al. (2001) "Cosecretion of Chaperones and Low-Molecular-Size Medium Additives Increases the Yield of Recombinant Disulfide-Bridged Proteins," *Applied and Environmental Microbiology*; 67(9):3994-4000.
Sela and Zisman (1997) "Different roles of D-amino acids in immune phenomena," *Faseb J.*; 11:449-456.
Shen et al. (2013) "Proprotein convertase subtilisin/kexin type 9 potentially influences cholesterol uptake in macrophages and reverse cholesterol transport," *FEBS Letters*; 587:1271-1274.
Smith et al. (1996) "Administration of interleukin-1 0 at the time of priming protects Corynebacterium parvum-primed mice against LPS- and TNF-alpha-induced lethality," *Cellular Immunology* 173(2):207-214.
Sneller et al. (2011) "IL-15 administered by continuous infusion to rhesus macaques induces massive expansion of CD8 T effector memory population in peripheral blood," *Blood*; 118(26):6845-6848.
Soman et al. (2009) "MTS dye based colorimetric CTLL-2 cell proliferation assay for product release and stability monitoring of Interleukin-15: Assay qualification, standardization and statistical analysis," *J Immunol Methods*; 348(1-2):83-94.
Song et al. (2012) "CD27 costimulation augments the survival and antitumor activity of redirected human T cells in vivo," *Blood*; 119(3):696-706.
Srivastava et al. (2013) "Effects of interleukin-18 on natural killer cells: costimulation of activation through Fc receptors for immunoglobulin," *Cancer Immunol Immunother*; 62(6):1073-1082.

(56) References Cited

OTHER PUBLICATIONS

Storici and Resnick (2006) "The delitto perfetto approach to in vivo site-directed mutagenesis and chromosome rearrangements with synthetic oligonucleotides in yeast," *Methods in Enzymology*; 409:329-345.

Sweredoski and Baldi (2009) "COBEpro: a novel system for predicting continuous B-cell epitopes," *Protein Eng Des Sel*; 22:113-120.

Syto et al. (1998) "Structural and biological stability of the human interleukin 10 homodimer," *Biochemistry*; 37(48):16943-16951.

Teng et al. (2015) "IL-12 and IL-23 cytokines: from discovery to targeted therapies for immune-mediated inflammatory diseases," *Nature Medicine*; 21:719-729.

Tilg et al. (2002) "Treatment of Crohn's disease with recombinant human interleukin 10 induces the proinflammatory cytokine interferon γ," *Gut*; 50:191-195.

Trandem et al. (2011) "Virally Expressed Interleukin-10 Ameliorates Acute Encephalomyelitis and Chronic Demyelination in Coronavirus-Infected Mice," *J. Virol.*; 85(14):6822-6831.

Tréhin et al. (2004) "Cellular uptake but low permeation of human calcitonin-derived cell penetrating peptides and Tat(47-57) through well-differentiated epithelial models," *Pharm. Research*; 21:1248-1256.

Tsumoto et al. (2003) "Practical considerations in refolding proteins from inclusion bodies," *Protein Expression and Purification*; 28:1-8.

Tsumoto et al. (2004) "Role of Arginine in Protein Refolding, Solubilization, and Purification," *Biotechnol. Prog.*; 20:1301-1308.

Valabrega et al. (2007) "Trastuzumab: mechanism of action, resistance and future perspectives in HER2-overexpressing breast cancer," *Annals of Oncology*; 18:977-984.

Van Deventer et al. (1997) "Multiple Doses of Intravenous Interleukin 10 in Steroid-Refractory Crohn's Disease," *Gastroenterology*, 113:383-389.

Vicari and Trinchieri (2004) "Interleukin-10 in viral diseases and cancer: exiting the labyrinth?," *Immunological Reviews*; 202:223-236.

Vigneron et al. (2013) "Database of T cell-defined human tumor antigens: the 2013 update," *Cancer Immunity*; 13:15-20.

Virgin, et al. (2009) "Redefining Chronic Viral Infection," *Cell*; 138:30-50.

Von Andrian and MacKay (2000) "T-cell function and migration. Two sides of the same coin," *New Engl J Med*; 343:1020-1034.

Waldmann et al. (2011) "Safety (toxicity), pharmacokinetics, immunogenicity, and impact on elements of the normal immune system of recombinant human IL-15 in rhesus macaques," *Blood*; 117:4787-4795.

Walter and Nagabhushan (1995) "Crystal structure of interleukin 10 reveals an interferon gamma-like fold," *Biochemistry*; (38):12118-12125.

Wee et al. (2010) "SVM-based prediction of linear B-cell epitopes using Bayes Feature Extraction," *BMC Genomics*; 11(Supp 4):S21.

Wender et al. (2000) "The design, synthesis, and evaluation of molecules that enable or enhance cellular uptake: peptoid molecular transporters," *Proc. Natl. Acad. Sci. USA*; 97:13003-13008.

Wilson et al. (2011) "The role of IL-10 in regulating immunity to persistent viral infections," *Curr Top Microbiol Immunol.*; 350:39-65.

Witsch et al. (2010) "Roles for Growth Facotes in Cancer Progression," *Physiology*; 25(2):85-101.

Wu et al. (2012) "Immunotherapies: The Blockade of Inhibitory Signals," *Int. J. Biol. Sci.*; 8:1420-1430.

Xu et al. (2010) "Regulation of Antitumor Immune Responses by the IL-12 Family Cytokines, IL-12, IL-23, and IL-27," *Clinical and Developmental Immunology*; Article ID:832454 (9 pages).

Yamaguchi and Miyazaki (2014) "Refolding Techniques for Recovering Biologically Active Recombinant Proteins from Inclusion Bodies," *Biomolecules*; 4:235-251.

Yoshioka et al. (2011) "Development of a novel DDS for site-specific PEGylated proteins," *Chem. Central J.*; 5:25.

Younes et al. (2004) "Phase II Clinical Trial of Interleukin-12 in Patients with Relapsed and Refractory Non-Hodgkin's Lymphoma and Hodgkin's Disease," *Clinical Cancer Research*; 10:5432-5438.

Zauner et al. (1996) "Glycerol Enhancement of Ligand-Polylysine/DNA Transfection," *BioTechniques*; 20:905-913.

Zdanov et al. (1995) "Crystal structure of interleukin-10 reveals the functional dimer with an unexpected topological similarity to interferon γ," *Structure*; 3:591-601.

Zdanov et al. (1996) "Crystal structure of human interleukin-10 at 1.6 A resolution and a model of a complex with its soluble receptor," *Protein Sci.*; (10):1955-1962.

Zender et al. (2002) "VP22-mediated intercellular transport of p53 in hepatoma cells in vitro and in vivo," *Cancer Gene Ther.*; 9(6):489-496.

Zheng et al. (1996) "Interleukin-10 inhibits tumor metastasis through an NK cell-dependent mechanism," *J Exp Med*; 184:579-584.

Mattos et al.,(2012) "11 PEGylation of interleukin-10 improves the pharmacokinetic profile and enhances the antifibrotic effectivity in eel-induced fibrogenesis in mice", Journal of Controlled Release, Elsevier, Amsterdam, NL, 162(I):84-91.

Gargett et al., (2015) "Different cytokine and stimul ation conditions influence t he expansion and immune phenotype of third-generat ion chimeric antigen receptor T cells specific for tumor antigen GD2", Cytotherapy, 17 (4):487-495.

Gill et al., (2015) "Going viral: Chimericantigen receptor T-cell therapy forhematological malignancies", Immunological Reviews 28150181 Blackwell Publishing Ltd GBR, 263(1):68-89.

Teng et al., (2011) "Stable IL-10: A new therapeutic that promotes tumor immunity" Cancer Cell 2011 Cell Press USA, 20(6):691-693.

Muecke, Susanne, et al., (2000) "Suppression of the Tumorigenic Growth of Burkitt's Lymphoma Cells in Immunodeficient Mice by Cytokine Gene Transfer Using EBV-Derived Episomal Expression Vectors", Int. J. Cancer, 86:301-306.

Mumm, John B., et al., (2012) "Killing from within" OncoImmunology, 1(9):1598-1600.

Klebanoff, CA et al., (2004) "IL-15 Enhances the in vivo Antitumor Activity of Tumor-reactive CD8+ T Cells", Proceedings of the National Academy of the Sciences of the U.S.A., 101(7):1969-1974.

Steel, JC et al., (2012) "Biology and its Therapeutic Implications in Cancer", Trends in Pharmacological Sciences, 33(1):35-41.

Aukrust et al., (2005) "Potential role for immunomodulatory therapy in atherosclerotic plaque stabilization", Expert Opinion Pharmacother, 6:2169-2180.

Cheon, H.G. (2013) "Latest research and development trends in non insulin anti-diabetics", Arch. Pharm. Res., 36:145-153.

Fichtlscherer et al., (2004) "Interleukin-10 serum levels and systemic endothelial vasoreactivity in patients with coronary artery desease", J. Am. Coll. Cardiol., 44:44-49.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Dec. 11, 2013, 3 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Jan. 31, 2014, 3 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Jul. 17, 2014, 6 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials. gov, Mar. 24, 2015, 7 pages.

NCT02009449, "A Phase 1, OpenLabel Dose Escalation FirstinHuman Study to Evaluate the Tolerability, Safety, Maximum Tolerated

(56) References Cited

OTHER PUBLICATIONS

Dose, Preliminary Clinical Activity and Pharmacokinetics of AM0010 in Patients With Advanced Solid Tumors", ClinicalTrials.gov, Jan. 12, 2016, 7 pages.

NCT02009449, "A Phase 1, OpenLabel Dose Escalation FirstinHuman Study to Evaluate the Tolerability, Safety, Maximum Tolerated Dose, Preliminary Clinical Activity and Pharmacokinetics of AM0010 in Patients With Advanced Solid Tumors", ClinicalTrials.gov, Oct. 2, 2016, 7 pages.

NCT02923921, "Randomized Study of AM0010 in Combination With FOLFOX Compared to FOLFOX Alone as Secondline Tx in Pts With Meta Pancreatic Cancer That Has Progressed During or Following a FirstLine Gemcitabine Containing Regimen", ClinicalTrials.gov, Oct. 4, 2016, 3 pages.

Cindric, et al., (2007) "Structural 1-16 characterization of PEGylated rHuG-CSF and location of PEG attachment sites". Journal of Pharmaceutical and Biomedical Analysis. New York. NY. US, 44(2)388-395.

Schneiderheinze, J., et al., (2009) "Rapid online proteolytic mapping of PEGylated rhGH for identity confirmation. quantitation of methionine oxidation and quantitation of UnPEGylated N-terminus using HPLC with UV detection", Journal of Chromatography B: Biomedical Sciences & Applications. Elsevier. Amsterdam. NL., 877(31):4065-4070.

Bowie, James, U., et al. (1990) "Deciphering the Message in Protein Sequences: Tolerance to Amino Acid Substitutions", Science, 247:1306-1310.

Burgess, Wilson, H., et al. (1990) "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue", J. Cell Bioi., 111:2129-2138.

Bork, Peer, (2000) "Powers and Pitfalls in Sequence Analysis: The 70% Hurdle", Genome Research, 10:398-400.

Lazar, Eliane, et al. (1988) "Transforming Growth Factor alpha: Mutation of Aspartic Acid 47 and Leucine 48 Results in Different Biological Activities", Mol. Cell. Bioi., 8:1247-1252.

UniProt reference P79338 (1L 1 O_MACFA) (downloaded from http://www.uniprot.org/uniprot/P79338, last sequence update May 1, 1997).

UniProt reference A21676 (1L 1 O_PANTR) (downloaded from http://www.uniprot.org/uniprot!A2T6Z6, last sequence update Mar. 6, 2007).

Soderquist, et al. (2010) "PEGylation of interleukin-1 0 for the mitigation of enhanced pain states", J Biomed Mater Res A, 3(93):1169-1179.

Gabriel, A., (2007) "Changes in plasma cholesterol in mood disorder patients: Does treatment make a difference?", Journal of Affective Disorders, 99:273-278.

Papadopoulou, Athanassia, et al., (2013) "Plasma total cholesterol in psychiatric patients after a suicide attempt and in follow-up", Journal of Affective Disorders, 148:440-443.

Virkkunen, M., (1979) "Serum Cholesterol in Antisocial Personality", Neuropsychobiology, 5:27-30.

Pjrek, Edda, et al., (2007) "Serum lipid levels in seasonal affective disorder", Eur Arch Psychiatry Clin Neurosci, 257:197-202.

Chang, et al., (2017) "CARs: Synthetic immunoreceptors for cancer therapy and beyond", Trends Mol. Med., 23:430-450.

Hermanson, et al., (2015) "Utilizing chimeric antigen receptors to direct natural killer cell activity", Frontiers in Immunology, 6:195.

Jaspers, et al., (2017) "Development of CART cells designed to improve antitumor efficacy and safety", Pharmac. & Therap., http://dx.doi.org,/1 0.1 016/j.pharmthera.2017.03.012.

Jensen, et al., (2015) "Designing chimeric antigen receptors to effectively and safely target tumors", Curr. Opin. Immunol., 33:9-15.

Chmielewski, et al, (2015) "TRUCKs: the fourth generation of CARs", Exp. Opin. Bioi. Ther., 15:1145-1154.

Hombach, et al., (2012) "OX40 costimulation by a chimeric antigen receptor abrogates CD28 and IL-2 induced IL-10 secretion by redirected CD4+ T cells", Oncolmmunol., 1:458-466.

Newick, et al., (2016) "CART cell therapy for solid tumors", Annu. Rev. Med., 68:139-152.

Gill, et al., (2015) "Going Viral: chimeric antigen receptor T-cell therapy for hematological malignancies", Immunol. Rev., 263:68-89.

Wylie et al. (2001) Pharm. Res., 2001 vol. 18, No. 9, pp. 1354-1360.

Dinant, et al., (2007) "1L-10 attenuates hepatic I/R injury and promotes hepatocyte proliferation", J. Surg. Res., 141:176-182.

Gotoh, et al., (2012) "A novel anti-inflammatory role for spleen-derived Interleukin-10 in obesity-induced inflammation in white adipose tissue and liver", Diabetes, 61:1994-2003.

Kumagai, et al., (2013) "Effects of Ezetimibe on hypercholesterolemia in the lipid profile in patients with metabolic syndrome", IJC Metabolic and Endocrine, 1:7-12.

\* cited by examiner

FIG. 1

Human IL-10 (NP_000563) (SEQ ID NO:1):
1         mhssallccl vlltgvrasp gqgtqsensc thfpgnlpnm lrdlrdafsr vktffqmkdq
61        ldnlllkesl ledfkgylgc qalsemiqfy leevmpqaen qdpdikahvn slgenlktlr
121       lrlrrchrfl pcenkskave qvknafnklq ekgiykamse fdifinyiea ymtmkirn Mouse IL-10 (NP_034678) (SEQ ID NO:2):
1         mpgsallccl llltgmrisr gqysrednnc thfpvgqshm llelrtafsq vktffqtkdq
61        ldnillltdsl mqdfkgylgc qalsemiqfy lvevmpqaek hgpeikehln slgeklktlr
121       mrlrrchrfl pcenkskave qvksdfnklq dqgvykamne fdifinciea ymmikmks

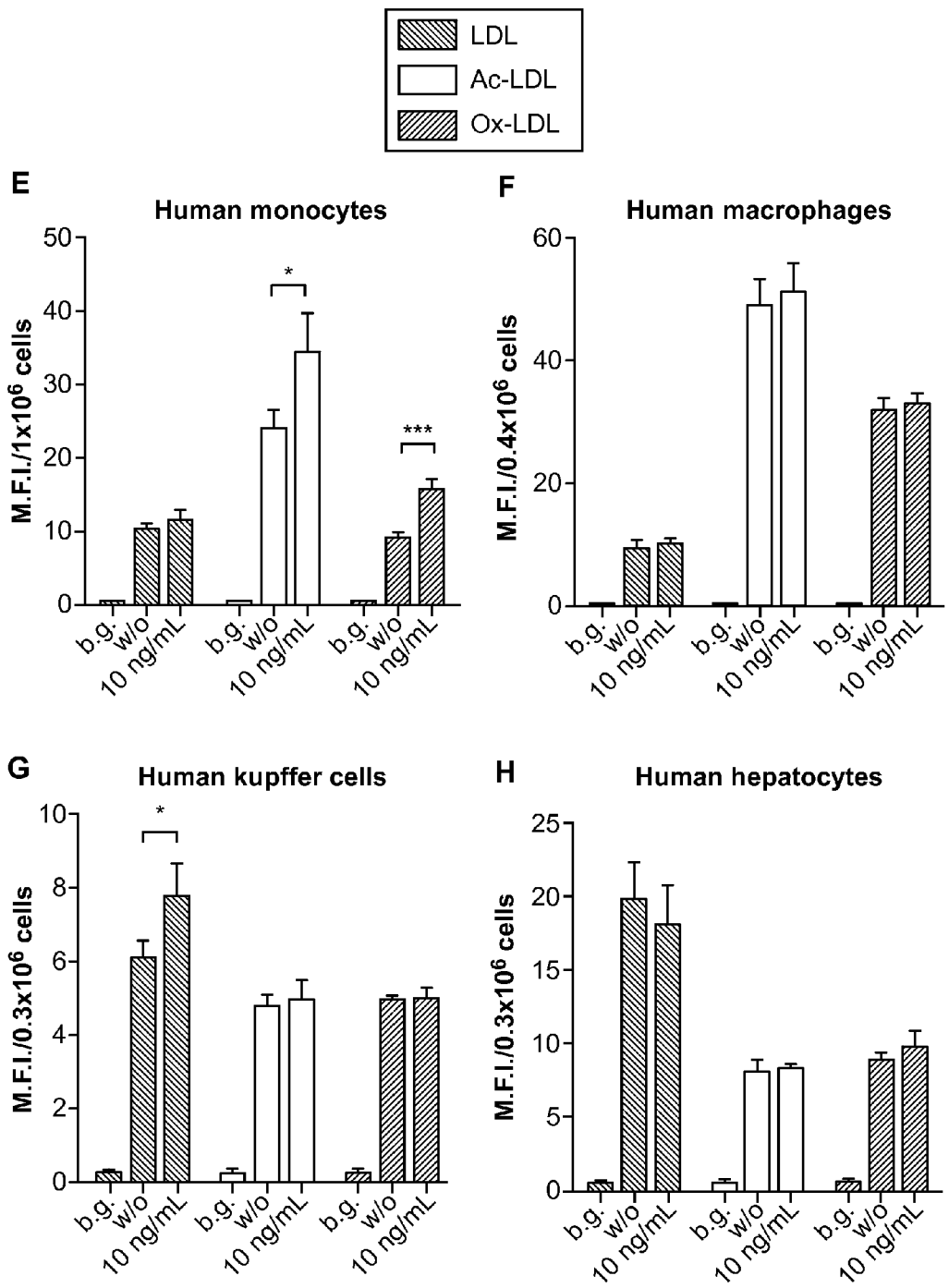
FIG. 8 (Cont. 1)

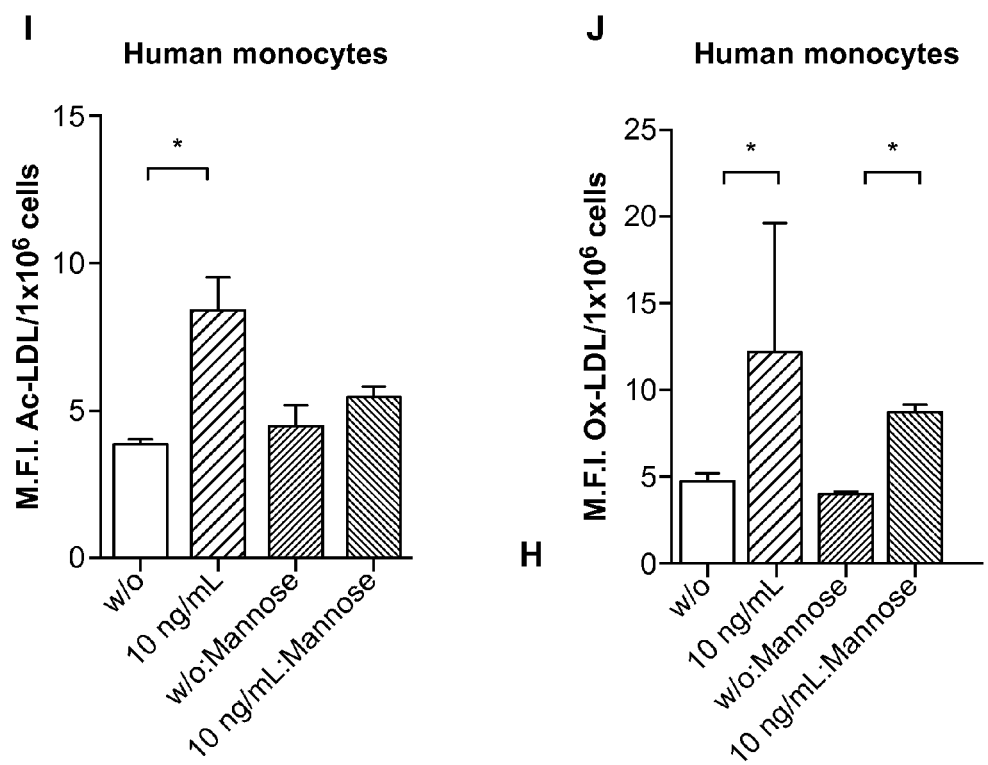
FIG. 8 (Cont. 2)

METHODS OF USING PEGYLATED INTERLEUKIN-10 FOR TREATING HYPERLIPIDEMIA

CROSS-REFERENCE TO RELATED APPLICATION

This application claims priority benefit of U.S. provisional application Ser. No. 61/872,394, filed Aug. 30, 2013, which application is incorporated herein in its entirety.

TECHNICAL FIELD

This invention generally relates to methods of using IL-10 and related agents in the treatment or prevention of hypercholesterolemia and a diverse array of related diseases and disorders.

INTRODUCTION

The cytokine interleukin-10 (IL-10) is a pleiotropic cytokine that regulates multiple immune responses through actions on T cells, B cells, macrophages, and antigen presenting cells (APC). IL-10 may suppress immune responses by inhibiting expression of IL-1α, IL-1β, IL-6, IL-8, TNF-α, GM-CSF and G-CSF in activated monocytes and activated macrophages, and it also suppresses IFN-γ production by NK cells. Although IL-10 is predominantly expressed in macrophages, expression has also been detected in activated T cells, B cells, mast cells, and monocytes. In addition to suppressing immune responses, IL-10 exhibits immunostimulatory properties, including stimulating the proliferation of IL-2 and IL-4-treated thymocytes, enhancing the viability of B cells, and stimulating the expression of MHC class II.

Human IL-10 is a homodimer that becomes biologically inactive upon disruption of the non-covalent interactions between the two monomer subunits. Data obtained from the published crystal structure of IL-10 indicates that the functional dimer exhibits certain similarities to IFN-γ (Zdanov et al, (1995) Structure (Lond) 3:591-601). As a result of its pleiotropic activity, IL-10 has been linked to a broad range of diseases, disorders and conditions, including inflammatory conditions, immune-related disorders, fibrotic disorders, metabolic disorders and cancer.

In view of the prevalence of metabolic diseases, disorders and conditions, such as hypercholesterolemia, and their associated morbidity, alternative treatment regimens and dosing parameters that optimize efficacy, patient tolerance and the like would be of tremendous value.

SUMMARY

The present disclosure contemplates methods of using IL-10, modified (e.g., pegylated) IL-10, and associated agents described herein, and compositions thereof, to treat and/or prevent various diseases, disorders and conditions, and/or the symptoms thereof. More particularly, the present disclosure relates to optimized dosing parameters to achieve and maintain efficacy in the treatment and/or prevention of metabolic diseases, disorders and conditions in a subject, while minimizing the adverse effects associated therewith. Particular embodiments are directed to the treatment and/or prevention of abnormally high levels of cholesterol and/or manifestation(s) of hypercholesterolemia in as subject. The present disclosure is based, in part, on the findings that there is an optimal mean IL-10 serum trough concentration range and an optimal dosing range that achieves maximally therapeutically relevant reduction of serum cholesterol with a minimum of exposure.

As set for the in detail hereafter, such optimization of dosing parameters involves, for example, the assessment of pharmacokinetic and pharmacodynamic parameters associated with absorption, distribution, metabolism, and excretion ("ADME"), taking into consideration the route of administration and other factors. It is understood that, unless indicated otherwise herein, terms related to ADME and other parameters are intended to have their ordinary accepted meanings in the relevant scientific fields. By way of example, the terms "serum half-life" or "$t_{1/2}$" refer to elimination half-life (i.e., the time at which the serum concentration of an agent has reached one-half of its initial or maximum value). As used herein, reference to serum concentration is meant to include plasma concentration, and vice versa.

Hypercholesterolemia itself is generally asymptomatic. However, chronic elevation of serum cholesterol contributes to formation of atheromatous plaques in the arteries. Relatively small plaques may rupture and cause a clot to form and obstruct blood flow. By comparison, larger plaques can result in arterial stenosis or occlusion of the involved arteries. A sudden occlusion of a coronary artery results in a myocardial infarction, whereas an occlusion of an artery supplying the brain can result in a stroke.

Gradual development of the stenosis or occlusion that causes a progressive reduction in the blood supply to the tissues and organs frequently results in impairment of the activity thereof. Tissue ischemia may manifest as one or more symptoms. For example, temporary ischemia of the brain (a transient ischemic attack) may manifest as temporary loss of vision, dizziness, or impairment of balance, aphasia, paresis and paresthesia. Insufficient blood supply to the heart may manifest as chest pain; ischemia of the eye may manifest as transient visual loss in one eye; and insufficient blood supply to the legs may manifest as calf pain.

Hypercholesterolemia may be categorized into various types with characteristic manifestations. For example, Type IIa hyperlipoproteinemia may be associated with xanthelasma palebarum (yellowish patches underneath the skin around the eyelids), arcus senilis (white or gray discoloration of the peripheral cornea), and xanthomata (deposition of yellowish cholesterol-rich material) of the tendons (usually the fingers). In contrast, Type III hyperlipidemia may be associated with xanthomata of the palms, knees and elbows.

According to the lipid hypothesis, abnormal cholesterol levels (generally higher concentrations of LDL particles and lower concentrations of functional HDL particles) in the blood are strongly associated with cardiovascular disease due to promotion of atheroma development in arteries (atherosclerosis). As high circulating LDL concentrations have been linked to atheroma formation, LDL is often referred to as "bad cholesterol"; in contrast, high concentrations of HDL can remove cholesterol from cells, diminishing atheroma formation, and thus HDL is often referred to as "good cholesterol". However, recent evidence suggests that total cholesterol is the most relevant indicator of cardiovascular abnormalities.

When dietary restrictions alone are insufficient in addressing hypercholesterolemia, one or more hypolipidemic agents (e.g., statins, fibrates, cholesterol absorption inhibitors, nicotinic acid derivatives and bile acid sequestrants) are often introduced. If pharmacological therapy is unsuccessful, several extreme procedures have been utilized (e.g., apheresisbased treatment). According to the teachings of the present disclosure, the IL-10-related agents described herein provide an alternative therapeutic modality that can be substituted for, or combined with, hypolipidemic agents such as those described herein.

As discussed further hereafter, human IL-10 is a homodimer and each monomer comprises 178 amino acids, the first 18 of which comprise a signal peptide. Particular embodiments of the present disclosure comprise mature human IL-10 polypeptides lacking the signal peptide (see, e.g., U.S. Pat. No. 6,217,857), or mature human PEG-IL-10. In further particular embodiments, the IL-10 agent is a variant of mature human IL-10. The variant may exhibit activity less than, comparable to, or greater than the activity of mature human IL-10; in certain embodiments the activity is comparable to or greater than the activity of mature human IL-10.

Certain embodiments of the present disclosure contemplate modification of IL-10 in order to enhance one or more properties (e.g., pharmacokinetic parameters, efficacy, etc.). Such IL-10 modifications include pegylation, glycosylation, albumin (e.g., human serum albumin (HSA)) conjugation and fusion, and hesylation. In particular embodiments, IL-10 is pegylated. In further embodiments, modification of IL-10 does not result in a therapeutically relevant, detrimental effect on immunogenicity, and in still further embodiments modified IL-10 is less immunogenic than unmodified IL-10. The terms "IL-10", "IL-10 polypeptide(s)," "agent(s)" and the like are intended to be construed broadly and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, the terms "IL-10", "IL-10 polypeptide(s), "agent(s)" are agonists. Particular embodiments relate to pegylated IL-10, which is also referred to herein as "PEG-IL-10". The present disclosure also contemplates nucleic acid molecules encoding the foregoing.

Particular embodiments of the present disclosure relate to methods of treating or preventing a disease, disorder or condition in a subject (e.g., a human), comprising administering to the subject a therapeutically effective amount of an IL-10 agent, wherein the amount is sufficient to achieve a mean IL-10 serum trough concentration from 1 pg/mL to 10.0 ng/mL; and wherein the disease disorder or condition is a) cardiovascular disorder, b) a thrombotic disorder, or c) an inflammatory disorder.

The present disclosure also contemplates embodiments drawn to methods of treating or preventing a disease, disorder or condition in a subject (e.g., a human), comprising administering to the subject a therapeutically effective amount of an IL-10 agent, wherein the amount is sufficient to maintain a mean IL-10 serum trough concentration over a period of time; wherein the disease disorder or condition is a) cardiovascular disorder, b) a thrombotic disorder, or c) an inflammatory disorder; wherein the mean IL-10 serum trough concentration is from 1.0 pg/mL to 10.0 ng/mL; and wherein the mean IL-10 serum trough concentration is maintained for at least 95% of the period of time.

In some embodiments of the present disclosure, the mean IL-10 serum trough concentration is in the range of from 1.0 pg/mL to 100 pg/mL; from 0.1 ng/mL to 1.0 ng/mL; from 1.0 ng/mL to 10 ng/mL; from 0.5 ng/mL to 5.0 ng/mL; from 0.75 ng/mL to 1.25 ng/mL or from 0.9 ng/mL to 1.1 ng/mL. In particular embodiments of the present disclosure, the mean IL-10 serum trough concentration is at least 1.25 ng/mL, at least 1.5 ng/mL, at least 1.6 ng/mL, at least 1.7 ng/mL, at least 1.8 ng/mL, at least 1.85 ng/mL, at least 1.9 ng/mL, at least 1.95 ng/mL, at least 1.97 ng/mL, and least 1.98 ng/mL, at least 1.99 ng/mL, at least 2.0 ng/mL or greater than 2 ng/mL. In further particular embodiments, the mean IL-10 serum trough concentration is less than 10.0 ng/mL, less than 9.0 ng/mL, less than 8.0 ng/mL, less than 7.0 ng/mL, less than 6.0 ng/mL, less than 5.0 ng/mL, less than 4.0 ng/mL, less than 3.0 ng/mL, less than 2.5 ng/mL, less than 2.0 ng/mL, less than 1.9 ng/mL, less than 1.8 ng/mL, less than 1.7 ng/mL, less than 1.6 ng/mL, less than 1.5 ng/mL, less than 1.4 ng/mL, less than 1.3 ng/mL, less than 1.2 ng/mL, less than 1.1 ng/mL, less than 1.0 ng/mL, less than 0.75 ng/mL, less than 0.5 ng/mL, less than 0.25 ng/mL, less than 0.1 ng/mL, less than 0.075 ng/mL, less than 0.05 ng/mL, less than 0.025 ng/mL or less than 0.01 ng/mL.

In further embodiments, the period of time is at least 12 hours, at least 24 hours, at least 48 hours, at least 72 hours, at least 1 week, at least 2 weeks, at least 3 weeks, at least 1 month, at least 6 weeks, at least 2 months, at least 3 months, at least 6 months, at least 9 months, or greater than 12 months.

In particular embodiments of the present disclosure, the mean IL-10 serum trough concentration is maintained for at least 85% of the period of time, at least 90%, at least 96%, at least 98%, at least 99% or 100% of the period of time.

It is envisaged that a dosing regimen sufficient to maintain a desired steady state serum trough concentration (e.g., 1 ng/mL) may result in an initial serum trough concentration that is higher than the desired steady state serum trough concentration. Because of the pharmacodynamic and pharmacokinetic characteristics of IL-10 in a mammalian subject, an initial trough concentration (achieved, for example, through the administration of one or more loading doses followed by a series of maintenance doses) gradually but continually decreases over a period of time even when the dosing parameters (amount and frequency) are kept constant. After that period to time, the gradual but continual decrease ends and a steady state serum trough concentration is maintained.

By way of example, parenteral administration (e.g., SC and IV) of about 0.1 mg/kg/day of an IL-10 agent (e.g., mIL-10) to a mouse (e.g., a C57BL/6 mouse) is required to maintain a steady state serum trough concentration of 2.0 ng/mL. However, that steady state serum trough concentration may not be achieved until approximately 30 days after initiation of dosing at 0.1 mg/kg/day (and also after any loading dose(s)). Rather, after an initial serum trough concentration has been achieved (e.g., 2.5 ng/mL), that concentration gradually but continually decreases over the course of, for example, the approximately 30-day period, after which time the desired steady state serum trough concentration (2.0 ng/mL) is maintained. One of skill in the art will be able to determine the dose needed to maintain the desired steady state trough concentration using, for example, ADME and patient-specific parameters.

The present disclosure contemplates methods wherein the IL-10 agent comprises at least one modification to form a modified IL-10 agent, wherein the modification does not alter the amino acid sequence of the IL-10 agent. In some embodiments, the modified IL-10 agent is a PEG-IL-10 agent. The PEG-IL-10 agent may comprise at least one PEG molecule covalently attached to at least one amino acid residue of at least one subunit of IL-10 or comprise a mixture of mono-pegylated and di-pegylated IL-10 in other embodiments. The PEG component of the PEG-IL-10 agent may have a molecular mass greater than about 5 kDa, greater than about 10 kDa, greater than about 15 kDa, greater than about 20 kDa, greater than about 30 kDa, greater than about 40 kDa, or greater than about 50 kDa. In some embodiments, the molecular mass is from about 5 kDa to about 10 kDa, from about 5 kDa to about 15 kDa, from about 5 kDa to about 20 kDa, from about 10 kDa to about 15 kDa, from about 10 kDa to about 20 kDa, from about 10 kDa to about 25 kDa or from about 10 kDa to about 30 kDa.

In some embodiments, the modified IL-10 agent comprises at least one Fc fusion molecule, at least one serum albumin (e.g., HSA or BSA), an HSA fusion molecule or an albumin conjugate. In additional embodiments, the modified IL-10 agent is glycosylated, is hesylated, or comprises at least one albumin binding domain. Some modified IL-10 agents may comprise more than one type of modification. In particular embodiments, the modification is site-specific. Some embodiments comprise a linker. Modified IL-10 agents are discussed in detail hereafter.

The present disclosure contemplates methods wherein the IL-10 agent is administered to the subject at least twice daily, at least once daily, at least once every 48 hours, at least once every 72 hours, at least once weekly, at least once every 2 weeks, at least once monthly, at least once every 2 months, or at least once every 3 months. Some embodiments also comprise administering the IL-10 agent with at least one additional prophylactic or therapeutic agent. In certain embodiments of the present disclosure, the prophylactic or therapeutic agent is a cholesterol homeostasis agent. In some embodiments, the cholesterol homeostasis agent comprises a statin, a bile acid resin, ezetimibe, a fibric acid, a niacin, or a PCSK9 inhibitor. The cholesterol hemostasis agent frequently improves, either directly or indirectly, a cardiovascular disorder. In particular embodiments, a prophylactic or therapeutic agent is one useful in the prevention or treatment of atherosclerosis. In additional embodiments, the prophylactic or therapeutic agent is an anti-diabetic agent or an anti-obesity agent, whereas in other embodiments it is an immune agent or an anti-inflammatory agent. Additional exemplary prophylactic and therapeutic agents are set forth hereafter.

The IL-10 agent may be administered by any effective route. In some embodiments, it is administered by parenteral injection, including subcutaneous injection.

Particular embodiments of the present disclosure relate to pharmaceutical compositions comprising a pharmaceutically acceptable amount of an IL-10 agent (e.g., a therapeutically effective amount), including those agents described above, along with one or more pharmaceutically acceptable diluent, carrier or excipient (e.g., an isotonic injection solution). The pharmaceutical composition is generally one that is suitable for human administration. Furthermore, in some embodiments the pharmaceutical composition comprises at least one additional prophylactic or therapeutic agent.

Certain embodiments of the present disclosure contemplate a sterile container that contains one of the above-mentioned pharmaceutical compositions and optionally one or more additional components. By way of example, but not limitation, the sterile container may be a syringe. In still further embodiments, the sterile container is one component of a kit; the kit may also contain, for example, a second sterile container that comprises at least one prophylactic or therapeutic agent, examples of which are set forth herein.

BRIEF DESCRIPTION OF THE DRAWINGS

FIG. 1 depicts the amino acid sequences of human IL-10 (SEQ ID NO:1) and mouse IL-10 (SEQ ID NO:2).

DETAILED DESCRIPTION

Figure 2A:
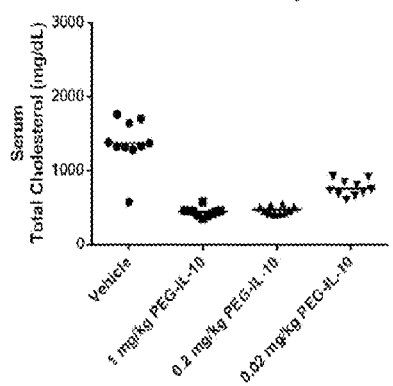
FIGS. 2A-E depict the effect of PEG-rmIL-10 exposure on the indicated lipid-related parameters in LDLR−/− mice fed a high fat diet. Mice were administered 1 mg/kg, 0.2 mg/kg, or 0.02 mg/kg or vehicle control SC daily for 14 days, and the following parameters were measured on Day 28: serum cholesterol (FIG. 2A); triglycerides (FIG. 2B); LDL (FIG. 2C); HDL (FIG. 2D); and LDL/HDL ratio (FIG. 2E). (n=10; bars represent the median of the datapoints).
Figure 2B:
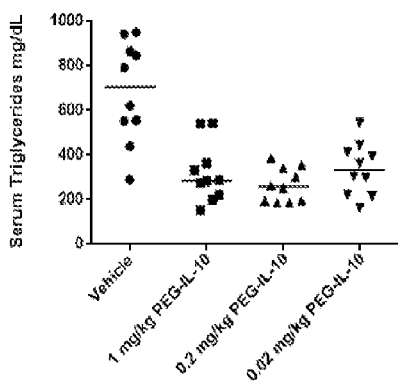
Figure 2C:
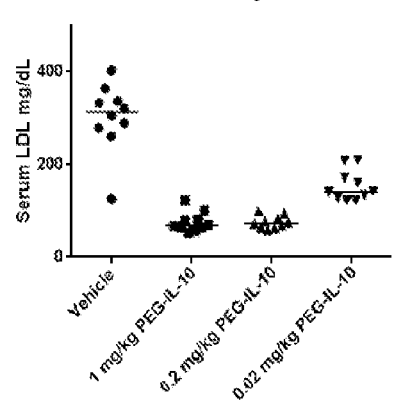

Before the present disclosure is further described, it is to be understood that the disclosure is not limited to the particular embodiments set forth herein, and it is also to be understood that the terminology used herein is for the purpose of describing particular embodiments only, and is not intended to be limiting.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention. Unless defined otherwise, all technical and scientific terms used herein have the same meaning as commonly understood by one of ordinary skill in the art to which this invention belongs.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology such as "solely," "only" and the like in connection with the recitation of claim elements, or use of a "negative" limitation.

The publications discussed herein are provided solely for their disclosure prior to the filing date of the present application. Further, the dates of publication provided may be different from the actual publication dates, which may need to be independently confirmed.

Overview

The present disclosure contemplates the use of the agents described herein, and compositions thereof, to treat and/or prevent various metabolic-related diseases (e.g., hypercholesterolemia), disorders and conditions, and/or the symptoms thereof. In certain aspects of the present disclosure, such treatment or prevention is effected by utilizing particular dosing parameters. The present disclosure is based on the findings that there is an optimal mean IL-10 serum trough concentration range and an optimal dosing range that achieves therapeutically relevant reduction of serum cholesterol and avoids severe toxicity resulting from higher IL-10 serum concentrations.

In some embodiments of the present disclosure, a subject having, or at risk of having, a disease or disorder treatable by an IL-10 agent (e.g., an IL-10 polypeptide) is administered the IL-10 agent in an amount sufficient to achieve a serum trough concentration greater than about 1 ng/mL but less than about 10 ng/mL, whereas in other embodiments the serum trough concentration is greater than about 2 ng/mL but less than about 10 ng/mL.

It should be noted that any reference to "human" in connection with the polypeptides and nucleic acid molecules of the present disclosure is not meant to be limiting with respect to the manner in which the polypeptide or nucleic acid is obtained or the source, but rather is only with reference to the sequence as it may correspond to a sequence of a naturally occurring human polypeptide or nucleic acid molecule. In addition to the human polypeptides and the nucleic acid molecules which encode them, the present disclosure contemplates IL-10-related polypeptides and corresponding nucleic acid molecules from other species.

Definitions

Unless otherwise indicated, the following terms are intended to have the meaning set forth below. Other terms are defined elsewhere throughout the specification.

The terms "patient" or "subject" are used interchangeably to refer to a human or a non-human animal (e.g., a mammal).

The terms "administration", "administer" and the like, as they apply to, for example, a subject, cell, tissue, organ, or biological fluid, refer to contact of, for example, IL-10 or PEG-IL-10), a nucleic acid (e.g., a nucleic acid encoding native human IL-10); a pharmaceutical composition comprising the foregoing, or a diagnostic agent to the subject, cell, tissue, organ, or biological fluid. In the context of a cell, administration includes contact (e.g., in vitro or ex vivo) of a reagent to the cell, as well as contact of a reagent to a fluid, where the fluid is in contact with the cell.

The terms "treat", "treating", treatment" and the like refer to a course of action (such as administering IL-10 or a pharmaceutical composition comprising IL-10) initiated after a disease, disorder or condition, or a symptom thereof, has been diagnosed, observed, and the like so as to eliminate, reduce, suppress, mitigate, or ameliorate, either temporarily or permanently, at least one of the underlying causes of a disease, disorder, or condition afflicting a subject, or at least one of the symptoms associated with a disease, disorder, condition afflicting a subject. Thus, treatment includes inhibiting (e.g., arresting the development or further development of the disease, disorder or condition or clinical symptoms association therewith) an active disease. The terms may also be used in other contexts, such as situations where IL-10 or PEG-IL-10 contacts an IL-10 receptor in, for example, the fluid phase or colloidal phase.

The term "in need of treatment" as used herein refers to a judgment made by a physician or other caregiver that a subject requires or will benefit from treatment. This judgment is made based on a variety of factors that are in the realm of the physician's or caregiver's expertise.

The terms "prevent", "preventing", "prevention" and the like refer to a course of action (such as administering IL-10 or a pharmaceutical composition comprising IL-10) initiated in a manner (e.g., prior to the onset of a disease, disorder, condition or symptom thereof) so as to prevent, suppress, inhibit or reduce, either temporarily or permanently, a subject's risk of developing a disease, disorder, condition or the like (as determined by, for example, the absence of clinical symptoms) or delaying the onset thereof, generally in the context of a subject predisposed to having a particular disease, disorder or condition. In certain instances, the terms also refer to slowing the progression of the disease, disorder or condition or inhibiting progression thereof to a harmful or otherwise undesired state.

The term "in need of prevention" as used herein refers to a judgment made by a physician or other caregiver that a subject requires or will benefit from preventative care. This judgment is made based on a variety of factors that are in the realm of a physician's or caregiver's expertise.

The phrase "therapeutically effective amount" refers to the administration of an agent to a subject, either alone or as part of a pharmaceutical composition and either in a single dose or as part of a series of doses, in an amount capable of having any detectable, positive effect on any symptom, aspect, or characteristic of a disease, disorder or condition when administered to the subject. The therapeutically effective amount can be ascertained by measuring relevant physiological effects, and it can be adjusted in connection with the dosing regimen and diagnostic analysis of the subject's condition, and the like. By way of example, measurement of the amount of inflammatory cytokines produced following administration may be indicative of whether a therapeutically effective amount has been used.

The phrase "in a sufficient amount to effect a change" means that there is a detectable difference between a level of an indicator measured before (e.g., a baseline level) and after administration of a particular therapy. Indicators include any objective parameter (e.g., serum concentration of IL-10) or subjective parameter (e.g., a subject's feeling of well-being).

The term "small molecules" refers to chemical compounds having a molecular weight that is less than about 10 kDa, less than about 2 kDa, or less than about 1 kDa. Small molecules include, but are not limited to, inorganic molecules, organic molecules, organic molecules containing an inorganic component, molecules comprising a radioactive atom, and synthetic molecules. Therapeutically, a small molecule may be more permeable to cells, less susceptible to degradation, and less likely to elicit an immune response than large molecules.

The term "ligand" refers to, for example, peptide, polypeptide, membrane-associated or membrane-bound molecule, or complex thereof, that can act as an agonist or antagonist of a receptor. "Ligand" encompasses natural and synthetic ligands, e.g., cytokines, cytokine variants, analogs, muteins, and binding compositions derived from antibodies. "Ligand" also encompasses small molecules, e.g., peptide mimetics of cytokines and peptide mimetics of antibodies. The term also encompasses an agent that is neither an agonist nor antagonist, but that can bind to a receptor without significantly influencing its biological properties, e.g., signaling or adhesion. Moreover, the term includes a membrane-bound ligand that has been changed, e.g., by chemical or recombinant methods, to a soluble version of the membrane-bound ligand. A ligand or receptor may be entirely intracellular, that is, it may reside in the cytosol, nucleus, or some other intracellular compartment. The complex of a ligand and receptor is termed a "ligand-receptor complex."

The terms "inhibitors" and "antagonists", or "activators" and "agonists" refer to inhibitory or activating molecules, respectively, for example, for the activation of, e.g., a ligand, receptor, cofactor, gene, cell, tissue, or organ. Inhibitors are molecules that decrease, block, prevent, delay activation, inactivate, desensitize, or down-regulate, e.g., a gene, protein, ligand, receptor, or cell. Activators are molecules that increase, activate, facilitate, enhance activation, sensitize, or up-regulate, e.g., a gene, protein, ligand, receptor, or cell. An inhibitor may also be defined as a molecule that reduces, blocks, or inactivates a constitutive activity. An "agonist" is a molecule that interacts with a target to cause or promote an increase in the activation of the target. An "antagonist" is a molecule that opposes the action(s) of an agonist. An antagonist prevents, reduces, inhibits, or neutralizes the activity of an agonist, and an antagonist can also prevent, inhibit, or reduce constitutive activity of a target, e.g., a target receptor, even where there is no identified agonist.

The terms "modulate", "modulation" and the like refer to the ability of a molecule (e.g., an activator or an inhibitor) to increase or decrease the function or activity of an IL-10 agent (or the nucleic acid molecules encoding them), either directly or indirectly; or to enhance the ability of a molecule to produce an effect comparable to that of an IL-10 agent. The term "modulator" is meant to refer broadly to molecules that can effect the activities described above. By way of example, a modulator of, e.g., a gene, a receptor, a ligand, or a cell, is a molecule that alters an activity of the gene, receptor, ligand, or cell, where activity can be activated, inhibited, or altered in its regulatory properties. A modulator may act alone, or it may use a cofactor, e.g., a protein, metal ion, or small molecule. The term "modulator" includes agents that operate through the same mechanism of action as IL-10 (i.e., agents that modulate the same signaling pathway as IL-10 in a manner analogous thereto) and are capable of eliciting a biological response comparable to (or greater than) that of IL-10.

Examples of modulators include small molecule compounds and other bioorganic molecules. Numerous libraries of small molecule compounds (e.g., combinatorial libraries) are commercially available and can serve as a starting point for identifying a modulator. The skilled artisan is able to develop one or more assays (e.g., biochemical or cell-based assays) in which such compound libraries can be screened in order to identify one or more compounds having the desired properties; thereafter, the skilled medicinal chemist is able to optimize such one or more compounds by, for example, synthesizing and evaluating analogs and derivatives thereof. Synthetic and/or molecular modeling studies can also be utilized in the identification of an Activator.

The "activity" of a molecule may describe or refer to the binding of the molecule to a ligand or to a receptor; to catalytic activity; to the ability to stimulate gene expression or cell signaling, differentiation, or maturation; to antigenic activity; to the modulation of activities of other molecules; and the like. The term may also refer to activity in modulating or maintaining cell-to-cell interactions (e.g., adhesion), or activity in maintaining a structure of a cell (e.g., a cell membrane). "Activity" can also mean specific activity, e.g., [catalytic activity]/[mg protein], or [immunological activity]/[mg protein], concentration in a biological compartment, or the like. The term "proliferative activity" encompasses an activity that promotes, that is necessary for, or that is specifically associated with, for example, normal cell division, as well as cancer, tumors, dysplasia, cell transformation, metastasis, and angiogenesis.

As used herein, "comparable", "comparable activity", "activity comparable to", "comparable effect", "effect comparable to", and the like are relative terms that can be viewed quantitatively and/or qualitatively. The meaning of the terms is frequently dependent on the context in which they are used. By way of example, two agents that both activate a receptor can be viewed as having a comparable effect from a qualitative perspective, but the two agents can be viewed as lacking a comparable effect from a quantitative perspective if one agent is only able to achieve 20% of the activity of the other agent as determined in an art-accepted assay (e.g., a dose-response assay) or in an art-accepted animal model. When comparing one result to another result (e.g., one result to a reference standard), "comparable" frequently means that one result deviates from a reference standard by less than 35%, by less than 30%, by less than 25%, by less than 20%, by less than 15%, by less than 10%, by less than 7%, by less than 5%, by less than 4%, by less than 3%, by less than 2%, or by less than 1%. In particular embodiments, one result is comparable to a reference standard if it deviates by less than 15%, by less than 10%, or by less than 5% from the reference standard. By way of example, but not limitation, the activity or effect may refer to efficacy, stability, solubility, or immunogenicity.

The term "response," for example, of a cell, tissue, organ, or organism, encompasses a change in biochemical or physiological behavior, e.g., concentration, density, adhesion, or migration within a biological compartment, rate of gene expression, or state of differentiation, where the change is correlated with activation, stimulation, or treatment, or with internal mechanisms such as genetic programming. In certain contexts, the terms "activation", "stimulation", and the like refer to cell activation as regulated by internal mechanisms, as well as by external or environmental factors; whereas the terms "inhibition", "down-regulation" and the like refer to the opposite effects.

The terms "polypeptide," "peptide," and "protein", used interchangeably herein, refer to a polymeric form of amino acids of any length, which can include genetically coded and non-genetically coded amino acids, chemically or biochemically modified or derivatized amino acids, and polypeptides having modified polypeptide backbones. The terms include fusion proteins, including, but not limited to, fusion proteins with a heterologous amino acid sequence; fusion proteins with heterologous and homologous leader sequences; fusion proteins with or without N-terminus methionine residues; fusion proteins with immunologically tagged proteins; and the like.

It will be appreciated that throughout this disclosure reference is made to amino acids according to the single letter or three letter codes. For the reader's convenience, the single and three letter amino acid codes are provided below:

| | | | | | |
|---|---|---|---|---|---|
| G | Glycine | Gly | P | Proline | Pro |
| A | Alanine | Ala | V | Valine | Val |
| L | Leucine | Leu | I | Isoleucine | Ile |
| M | Methionine | Met | C | Cysteine | Cys |
| F | Phenylalanine | Phe | Y | Tyrosine | Tyr |
| W | Tryptophan | Trp | H | Histidine | His |
| K | Lysine | Lys | R | Arginine | Arg |
| Q | Glutamine | Gln | N | Asparagine | Asn |
| E | Glutamic Acid | Glu | D | Aspartic Acid | Asp |
| S | Serine | Ser | T | Threonine | Thr |

As used herein, the term "variant" encompasses naturally-occurring variants and non-naturally-occurring variants. Naturally-occurring variants include homologs (polypeptides and nucleic acids that differ in amino acid or nucleotide sequence, respectively, from one species to another), and allelic variants (polypeptides and nucleic acids that differ in amino acid or nucleotide sequence, respectively, from one individual to another within a species). Non-naturally-occurring variants include polypeptides and nucleic acids that comprise a change in amino acid or nucleotide sequence, respectively, where the change in sequence is artificially introduced (e.g., muteins); for example, the change is generated in the laboratory by human intervention ("hand of man"). Thus, herein a "mutein" refers broadly to mutated recombinant proteins that usually carry single or multiple amino acid substitutions and are frequently derived from cloned genes that have been subjected to site-directed or random mutagenesis, or from completely synthetic genes.

The terms "DNA", "nucleic acid", "nucleic acid molecule", "polynucleotide" and the like are used interchangeably herein to refer to a polymeric form of nucleotides of any length, either deoxyribonucleotides or ribonucleotides, or analogs thereof. Non-limiting examples of polynucleotides include linear and circular nucleic acids, messenger RNA (mRNA), complementary DNA (cDNA), recombinant polynucleotides, vectors, probes, primers and the like.

As used herein in the context of the structure of a polypeptide, "N-terminus" (or "amino terminus") and "C-terminus" (or "carboxyl terminus") refer to the extreme amino and carboxyl ends of the polypeptide, respectively, while the terms "N-terminal" and "C-terminal" refer to relative positions in the amino acid sequence of the polypeptide toward the N-terminus and the C-terminus, respectively, and can include the residues at the N-terminus and C-terminus, respectively. "Immediately N-terminal" or "immediately C-terminal" refers to a position of a first amino acid residue relative to a second amino acid residue where the first and second amino acid residues are covalently bound to provide a contiguous amino acid sequence.

"Derived from", in the context of an amino acid sequence or polynucleotide sequence (e.g., an amino acid sequence "derived from" an IL-10 polypeptide), is meant to indicate that the polypeptide or nucleic acid has a sequence that is based on that of a reference polypeptide or nucleic acid (e.g., a naturally occurring IL-10 polypeptide or an IL-10-encoding nucleic acid), and is not meant to be limiting as to the source or method in which the protein or nucleic acid is made. By way of example, the term "derived from" includes homologs or variants of reference amino acid or DNA sequences.

In the context of a polypeptide, the term "isolated" refers to a polypeptide of interest that, if naturally occurring, is in an environment different from that in which it may naturally occur. "Isolated" is meant to include polypeptides that are within samples that are substantially enriched for the polypeptide of interest and/or in which the polypeptide of interest is partially or substantially purified. Where the polypeptide is not naturally occurring, "isolated" indicates that the polypeptide has been separated from an environment in which it was made by either synthetic or recombinant means.

"Enriched" means that a sample is non-naturally manipulated (e.g., by a scientist) so that a polypeptide of interest is present in a) a greater concentration (e.g., at least 3-fold greater, at least 4-fold greater, at least 8-fold greater, at least 64-fold greater, or more) than the concentration of the polypeptide in the starting sample, such as a biological sample (e.g., a sample in which the polypeptide naturally occurs or in which it is present after administration), or b) a concentration greater than the environment in which the polypeptide was made (e.g., as in a bacterial cell).

"Substantially pure" indicates that a component (e.g., a polypeptide) makes up greater than about 50% of the total content of the composition, and typically greater than about 60% of the total polypeptide content. More typically, "substantially pure" refers to compositions in which at least 75%, at least 85%, at least 90% or more of the total composition is the component of interest. In some cases, the polypeptide will make up greater than about 90%, or greater than about 95% of the total content of the composition.

The terms "specifically binds" or "selectively binds", when referring to a ligand/receptor, antibody/antigen, or other binding pair, indicates a binding reaction which is determinative of the presence of the protein in a heterogeneous population of proteins and other biologics. Thus, under designated conditions, a specified ligand binds to a particular receptor and does not bind in a significant amount to other proteins present in the sample. The antibody, or binding composition derived from the antigen-binding site of an antibody, of the contemplated method binds to its antigen, or a variant or mutein thereof, with an affinity that is at least two-fold greater, at least ten times greater, at least 20-times greater, or at least 100-times greater than the affinity with any other antibody, or binding composition derived therefrom. In a particular embodiment, the antibody will have an affinity that is greater than about $10^9$ liters/mol, as determined by, e.g., Scatchard analysis (Munsen, et al. 1980 Analyt. Biochem. 107:220-239).

IL-10 and PEG-IL-10

The anti-inflammatory cytokine IL-10, also known as human cytokine synthesis inhibitory factor (CSIF), is classified as a type(class)-2 cytokine, a set of cytokines that includes IL-19, IL-20, IL-22, IL-24 (Mda-7), and IL-26, interferons (IFN-α, -β, -γ, -δ, -ε, -κ, -Ω, and -τ) and interferon-like molecules (limitin, IL-28A, IL-28B, and IL-29).

IL-10 is a cytokine with pleiotropic effects in immunoregulation and inflammation. It is produced by mast cells, counteracting the inflammatory effect that these cells have at the site of an allergic reaction. While it is capable of inhibiting the synthesis of pro-inflammatory cytokines such as IFN-γ, IL-2, IL-3, TNFα and GM-CSF, IL-10 is also stimulatory towards certain T cells and mast cells and stimulates B-cell maturation, proliferation and antibody production. IL-10 can block NF-κB activity and is involved in the regulation of the JAK-STAT signaling pathway. It also induces the cytotoxic activity of CD8+ T-cells and the antibody production of B-cells, and it suppresses macrophage activity and tumor-promoting inflammation. The regulation of CD8+ T-cells is dose-dependent, wherein higher doses induce stronger cytotoxic responses.

Human IL-10 is a homodimer with a molecular mass of 37 kDa, wherein each 18.5 kDa monomer comprises 178 amino acids, the first 18 of which comprise a signal peptide, and two cysteine residues that form two intramolecular disulfide bonds. The IL-10 dimer becomes biologically inactive upon disruption of the non-covalent interactions between the two monomer subunits.

The present disclosure contemplates human IL-10 and murine IL-10, which exhibit 80% homology, and use thereof. In addition, the scope of the present disclosure includes IL-10 orthologs, and modified forms thereof, from other mammalian species, including rat (accession NP_036986.2; GI 148747382); cow (accession NP_776513.1; GI 41386772); sheep (accession NP_001009327.1; GI 57164347); dog (accession ABY86619.1; GI 166244598); and rabbit (accession AAC23839.1; GI 3242896).

As alluded to above, the terms "IL-10", "IL-10 polypeptide(s), "IL-10 agent(s)" and the like are intended to be broadly construed and include, for example, human and non-human IL-10-related polypeptides, including homologs, variants (including muteins), and fragments thereof, as well as IL-10 polypeptides having, for example, a leader sequence (e.g., the signal peptide), and modified versions of the foregoing. In further particular embodiments, IL-10, IL-10 polypeptide(s), and IL-10 agent(s) are agonists.

The IL-10 receptor, a type II cytokine receptor, consists of alpha and beta subunits, which are also referred to as R1 and R2, respectively. Receptor activation requires binding to both alpha and beta. One homodimer of an IL-10 polypeptide binds to alpha and the other homodimer of the same IL-10 polypeptide binds to beta.

The utility of recombinant human IL-10 is frequently limited by its relatively short serum half-life, which may be due to, for example, renal clearance, proteolytic degradation and monomerization in the blood stream. As a result, various approaches have been explored to improve the pharmacokinetic profile of IL-10 without disrupting its dimeric structure and thus adversely affecting its activity. Pegylation of IL-10 results in improvement of certain pharmacokinetic parameters (e.g., serum half-life) and/or enhancement of activity.

As used herein, the terms "pegylated IL-10" and PEG-IL-10" refer to an IL-10 molecule having one or more polyethylene glycol molecules covalently attached to at least one amino acid residue of the IL-10 protein, generally via a linker, such that the attachment is stable. The terms "monopegylated IL-10" and "mono-PEG-IL-10" indicate that one polyethylene glycol molecule is covalently attached to a single amino acid residue on one subunit of the IL-10 dimer, generally via a linker. In certain embodiments, the PEG-IL-10 used in the present disclosure is a mono-PEG-IL-10 in which one to nine PEG molecules are covalently attached via a linker to the alpha amino group of the amino acid residue at the N-terminus of one subunit of the IL-10 dimer. Monopegylation on one IL-10 subunit generally results in a non-homogeneous mixture of non-pegylated, monopegylated and dipegylated IL-10 due to subunit shuffling. Moreover, allowing a pegylation reaction to proceed to completion will generally result in non-specific and multi-pegylated IL-10, thus reducing its bioactivity. Thus, particular embodiments of the present disclosure comprise the administration of a mixture of mono- and di-pegylated IL-10 produced by the methods described herein (e.g., the Experimental section).

In particular embodiments, the average molecular weight of the PEG moiety is between about 5 kDa and about 50 kDa. Although the method or site of PEG attachment to IL-10 is not critical, in certain embodiments the pegylation does not alter, or only minimally alters, the activity of the IL-10 agent. In certain embodiments, the increase in half-life is greater than any decrease in biological activity. The biological activity of PEG-IL-10 is typically measured by assessing the levels of inflammatory cytokines (e.g., TNF-α or IFN-γ) in the serum of subjects challenged with a bacterial antigen (lipopolysaccharide (LPS)) and treated with PEG-IL-10, as described in U.S. Pat. No. 7,052,686.

IL-10 variants can be prepared with various objectives in mind, including increasing serum half-life, reducing an immune response against the IL-10, facilitating purification or preparation, decreasing conversion of IL-10 into its monomeric subunits, improving therapeutic efficacy, and lessening the severity or occurrence of side effects during therapeutic use. The amino acid sequence variants are usually predetermined variants not found in nature, although some may be post-translational variants, e.g., glycosylated variants. Any variant of IL-10 can be used provided it retains a suitable level of IL-10 activity.

The phrase "conservative amino acid substitution" refers to substitutions that preserve the activity of the protein by replacing an amino acid(s) in the protein with an amino acid with a side chain of similar acidity, basicity, charge, polarity, or size of the side chain. Conservative amino acid substitutions generally entail substitution of amino acid residues within the following groups: 1) L, I, M, V, F; 2) R, K; 3) F, Y, H, W, R; 4) G, A, T, S; 5) Q, N; and 6) D, E. Guidance for substitutions, insertions, or deletions may be based on alignments of amino acid sequences of different variant proteins or proteins from different species. Thus, in addition to any naturally-occurring IL-10 polypeptide, the present disclosure contemplates having 1, 2, 3, 4, 5, 6, 7, 8, 9, or 10 usually no more than 20, 10, or 5 amino acid substitutions, where the substitution is usually a conservative amino acid substitution.

The present disclosure also contemplates active fragments (e.g., subsequences) of mature IL-10 containing contiguous amino acid residues derived from the mature IL-10. The length of contiguous amino acid residues of a peptide or a polypeptide subsequence varies depending on the specific naturally-occurring amino acid sequence from which the subsequence is derived. In general, peptides and polypeptides may be from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

Additionally, IL-10 polypeptides can have a defined sequence identity compared to a reference sequence over a defined length of contiguous amino acids (e.g., a "comparison window"). Methods of alignment of sequences for comparison are well-known in the art. Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman, Proc. Nat'l. Acad. Sci. USA 85:2444 (1988), by computerized implementations of these algorithms (GAP, BESTFIT, FASTA, and TFASTA in the Wisconsin Genetics Software Package, Madison, Wis.), or by manual alignment and visual inspection (see, e.g., Current Protocols in Molecular Biology (Ausubel et al., eds. 1995 supplement)).

As an example, a suitable IL-10 polypeptide can comprise an amino acid sequence having at least about 75%, at least about 80%, at least about 85%, at least about 90%, at least about 95%, at least about 98%, or at least about 99%, amino acid sequence identity to a contiguous stretch of from about 20 amino acids to about 40 amino acids, from about 40 amino acids to about 60 amino acids, from about 60 amino acids to about 80 amino acids, from about 80 amino acids to about 100 amino acids, from about 100 amino acids to about 120 amino acids, from about 120 amino acids to about 140 amino acids, from about 140 amino acids to about 150 amino acids, from about 150 amino acids to about 155 amino acids, from about 155 amino acids up to the full-length peptide or polypeptide.

As discussed further below, the IL-10 polypeptides may be isolated from a natural source (e.g., an environment other than its naturally-occurring environment) and may also be recombinantly made (e.g., in a genetically modified host cell such as bacteria, yeast, Pichia, insect cells, and the like), where the genetically modified host cell is modified with a nucleic acid comprising a nucleotide sequence encoding the polypeptide. The IL-10 polypeptides may also be synthetically produced (e.g., by cell-free chemical synthesis).

Nucleic acid molecules encoding the IL-10 agents are contemplated by the present disclosure, including their naturally-occurring and non-naturally occurring isoforms, allelic variants and splice variants. The present disclosure also encompasses nucleic acid sequences that vary in one or more bases from a naturally-occurring DNA sequence but still translate into an amino acid sequence that corresponds to an IL-10 polypeptide due to degeneracy of the genetic code.

IL-10 Serum Concentration

The blood plasma levels of IL-10 in the methods described herein may be characterized in several manners, including: (1) a mean IL-10 serum trough concentration above some specified level or in a range of levels; (2) a mean IL-10 serum trough concentration above some specified level for some amount of time; (3) a steady state IL-10 serum concentration level above or below some specified level or in a range of levels; or (4) a $C_{max}$ of the concentration profile above or below some specified level or in some range of levels. As set forth herein, mean serum trough IL-10 concentrations have been found to be of particular import for efficacy in certain indications.

In some embodiments of the present disclosure, blood plasma and/or serum level concentration profiles that may be produced include: a mean IL-10 plasma and/or serum trough concentration of greater than about 1.0 pg/mL, greater than about 10.0 pg/mL, greater than about 20.0 pg/mL, greater than about 30 pg/mL, greater than about 40 pg/mL, greater than about 50.0 pg/mL, greater than about 60.0 pg/mL, greater than about 70.0 pg/mL, greater than about 80.0 pg/mL, greater than about 90 pg/mL, greater than about 0.1 ng/mL, greater than about 0.2 ng/mL, greater than about 0.3 ng/mL, greater than about 0.4 ng/mL, greater than about 0.5 ng/mL, greater than about 0.6 ng/mL, greater than about 0.7 ng/mL, greater than about 0.8 ng/mL, greater than about 0.9 ng/mL, greater than about 1.0 ng/mL, greater than about 1.5 ng/mL, greater than about 2.0 ng/mL, greater than about 2.5 ng/mL, greater than about 3.0 ng/mL, greater than about 3.5 ng/mL, greater than about 4.0 ng/mL, greater than about 4.5 ng/mL, greater than about 5.0 ng/mL, greater than about 5.5 ng/mL, greater than about 6.0 ng/mL, greater than about 6.5 ng/mL, greater than about 7.0 ng/mL, greater than about 7.5 ng/mL, greater than about 8.0 ng/mL, greater than about 8.5 ng/mL, greater than about 9.0 ng/mL, greater than about 9.5 ng/mL, or greater than about 10.0 ng/mL. In further embodiments, blood plasma and/or serum level concentration profiles that may be produced include: a mean IL-10 plasma and/or serum trough concentration of less than about 10.0 ng/mL, less than about 9.0 ng/mL, less than about 8.0 ng/mL, less than about 7.0 ng/mL, less than about 6.0 ng/mL, less than about 5.0 ng/mL, less than about 4.0 ng/mL, less than about 3.0 ng/mL, less than about 2.5 ng/mL, less than about 2.0 ng/mL, less than about 1.9 ng/mL, less than about 1.8 ng/mL, less than about 1.7 ng/mL, less than about 1.6 ng/mL, less than about 1.5 ng/mL, less than about 1.4 ng/mL, less than about 1.3 ng/mL, less than about 1.2 ng/mL, less than about 1.1 ng/mL, less than about 1.0 ng/mL, less than about 0.75 ng/mL, less than about 0.5 ng/mL, less than about 0.25 ng/mL, less than about 0.1 ng/mL, less than about 0.075 ng/mL, less than about 0.05 ng/mL, less than about 0.025 ng/mL or less than about 0.01 ng/mL.

In particular embodiments of the present disclosure, a mean IL-10 serum trough concentration is in the range of from 1.0 pg/mL to 10 ng/mL. In some embodiments, the mean IL-10 serum trough concentration is in the range of from 1.0 pg/mL to 100 pg/mL, In other embodiments, the mean IL-10 serum trough concentration is in the range of from 0.1 ng/mL to 1.0 ng/mL. In still other embodiments, the mean IL-10 serum trough concentration is in the range of from 1.0 ng/mL to 10 ng/mL. It is to be understood that the present disclosure contemplates ranges incorporating any concentrations encompassed by those set forth herein even if such ranges are not explicitly recited. By way of example, the mean serum IL-10 concentration in an embodiment may be in the range of from 0.5 ng/mL to 5 ng/mL. By way of further examples, particular embodiments of the present disclosure comprise a mean IL-10 serum trough concentration in a range of from about 1.0 pg/mL to about 9.5 ng/mL, from about 0.5 ng/mL to about 10.5 ng/mL, from about 1.0 ng/mL to about 10.0 ng/mL, from about 1.0 ng/mL to about 9.0 ng/mL, from about 1.0 ng/mL to about 8.0 ng/mL, from about 1.0 ng/mL to about 7.0 ng/mL, from about 1.5 ng/mL to about 10.0 ng/mL, from about 1.5 ng/mL to about 9.0 ng/mL, from about 1.5 ng/mL to about 8.0 ng/mL, from about 1.5 ng/mL to about 7.0 ng/mL, from about 2.0 ng/mL to about 10.0 ng/mL, from about 2.0 ng/mL to about 9.0 ng/mL, from about 2.0 ng/mL to about 8.0 ng/mL, and from about 2.0 ng/mL to about 7.0 ng/mL.

In particular embodiments, a mean IL-10 serum trough concentration of 1-2 ng/mL is maintained over the duration of treatment. The present disclosure also contemplates embodiments wherein the mean IL-10 serum peak concentration is less than or equal to about 10.0 ng/mL over the duration of treatment. Further embodiments contemplate a mean IL-10 serum trough concentration greater than or equal to about 1.0 pg/mL. The optimal mean serum concentration is generally that at which the desired therapeutic effect is achieved without introducing undesired adverse effects. In most patient populations, maximum serum cholesterol reduction is frequently achieved at mean IL-10 serum trough concentrations of from about 1.0 ng/mL to about 10 ng/mL; at such concentrations, unacceptable adverse effects are generally not observed. However, lower mean Il-10 serum trough concentrations may also be advantageous in certain patient populations. For example, IL-10 serum trough concentrations of from about 0.1 ng/mL to about 1.0 ng/mL have been shown to decrease serum cholesterol levels by approximately 30%; such lower IL-10 serum trough concentrations might be a therapeutic goal in patients who exhibit adverse effects at higher concentrations. Moreover, low picogram per milliliter IL-10 serum levels may dramatically decrease arterial and other plaques.

Certain embodiments of the present disclosure provide a method for monitoring a subject receiving IL-10 therapy to predict, and thus potentially avoid, adverse effects, the method comprising: (1) measuring the subject's peak concentration of IL-10; (2) measuring the subject's trough concentration of IL-10; (3) calculating a peak-trough fluctuation; and, (4) using the calculated peak-trough fluctuation to predict potential adverse effects in the subject. In particular subject populations, a smaller peak-trough fluctuation indicates a lower probability that the subject will experience IL-10-related adverse effects. In addition, in some embodiments particular peak-trough fluctuations are determined for the treatment of particular diseases, disorders and conditions using particular dosing parameters, and those fluctuations are used as reference standards.

For the majority of drugs, plasma drug concentrations decline in a multi-exponential fashion. Immediately after intravenous administration, the drug rapidly distributes throughout an initial space (minimally defined as the plasma volume), and then a slower, equilibrative distribution to extravascular spaces (e.g., certain tissues) occurs. Intravenous IL-10 administration is associated with such a two-compartment kinetic model (see Rachmawati, H. et al. (2004) Pharm. Res. 21(11):2072-78). The pharmacokinetics of subcutaneous recombinant hIL-10 has also been studied (Radwanski, E. et al. (1998) Pharm. Res. 15(12):1895-1901). Thus, volume-of-distribution considerations are pertinent when assessing appropriate IL-10 dosing-related parameters. Moreover, efforts to target IL-10 agents to specific cell types have been explored (see, e.g., Rachmawati, H. (May 2007) Drug Met. Dist. 35(5):814-21), and the leveraging of IL-10 pharmacokinetic and dosing principles may prove invaluable to the success of such efforts.

The present disclosure contemplates administration of any dose and dosing regimen that results in maintenance of any of the IL-10 serum trough concentrations set forth above. By way of example, but not limitation, when the subject is a human, non-pegylated hIL-10 may be administered at a dose greater than 0.5 µg/kg/day, greater than 1.0 µg/kg/day, greater than 2.5 µg/kg/day, greater than 5 µg/kg/day, greater than 7.5 µg/kg, greater than 10.0 µg/kg, greater than 12.5 µg/kg, greater than 15 µg/kg/day, greater than 17.5 µg/kg/day, greater than 20 µg/kg/day, greater than 22.5 µg/kg/day, greater than 25 µg/kg/day, greater than 30 µg/kg/day, or greater than 35 µg/kg/day. In addition, by way of example, but not limitation, when the subject is a human, pegylated hIL-10 comprising a relatively small PEG (e.g., 5 kDa mono-di-PEG-hIL-10) may be administered at a dose greater than 0.5 µg/kg/day, greater than 0.75 µg/kg/day, greater than 1.0 µg/kg/day, greater than 1.25 µg/kg/day, greater than 1.5 µg/kg/day, greater than 1.75 µg/kg/day, greater than 2.0 µg/kg/day, greater than 2.25 µg/kg/day, greater than 2.5 µg/kg/day, greater than 2.75 µg/kg/day, greater than 3.0 µg/kg/day, greater than 3.25 µg/kg/day, greater than 3.5 µg/kg/day, greater than 3.75 µg/kg/day, greater than 4.0 µg/kg/day, greater than 4.25 µg/kg/day, greater than 4.5 µg/kg/day, greater than 4.75 µg/kg/day, or greater than 5.0 µg/kg/day. In certain embodiments of the present disclosure, when the subject is a human, non-pegylated hIL-10 may be administered at a dose less than 50 µg/kg/day, less than 40 µg/kg/day, less than 35 µg/kg/day, less than 30 µg/kg/day, less than 25 µg/kg/day, less than 20 µg/kg/day, less than 15 µg/kg/day, less than 12.5 µg/kg/day, less than 10 µg/kg/day, less than 7.5 µg/kg/day, less than 5.0 µg/kg/day, less than 2.5 µg/kg/day, less than 2.0 µg/kg/day, less than 1.5 µg/kg/day, or less than 1.0 µg/kg/day. In further embodiments, by way of example, but not limitation, when the subject is a human, pegylated hIL-10 comprising a relatively small PEG (e.g., 5 kDa mono-di-PEG-hIL-10) may be administered at a dose less than 5.0 µg/kg/day, less than 4.5 µg/kg/day, less than 4.0 µg/kg/day, less than 3.5 µg/kg/day, less than 3.0 µg/kg/day, less than 2.5 µg/kg/day, less than 2.0 µg/kg/day, less than 1.75 µg/kg/day, less than 1.5 µg/kg/day, less than 1.25 µg/kg/day, less than 1.0 µg/kg/day, less than 0.75 µg/kg/day, or less than 0.5 µg/kg/day.

Cholesterol and the Effect of PEG-IL-10 on Cholesterol Homeostasis and Indicators Thereof Physiology:

Cholesterol plays an indispensable role in a vast array of physiological processes, including cell membrane structure, and biosynthesis of steroid hormones, bile acids and vitamin D. Cholesterol synthesis entails a complex 37-step process that begins with the reduction of 3-hydroxy-3-methylglutaryl CoA (HMG-CoA) to mevalonate by the enzyme HGM-CoA reductase. This is the regulated, rate-limiting and irreversible step in cholesterol synthesis and is the site of action for the statin drugs (HMG-CoA reductase competitive inhibitors).

The liver is the major regulator of cholesterol. Not only is it the site of formation of VLDL, the precursor of most LDL in the circulation, it is also the location where the vast majority of receptor-mediated clearance of LDL takes place.

The liver initially clears all the cholesterol that is absorbed from the small intestine. Absorption of excess cholesterol may increase the amount of cholesterol stored in the liver, resulting in increased VLDL secretion (and thus LDL formation) and down-regulation of hepatic LDL-receptor activity. On average, about half of all cholesterol entering the intestine is absorbed. The fractional absorption rate varies greatly among individuals, which may explain, at least in part, why some patients respond poorly, or not at all, to statins and other classes of lipid-lowering drugs. See, e.g., Turley, S D, (2004) Clin. Cardiol. 6 Suppl 3:11116-21. The liver also recycles cholesterol by excreting it in a non-esterified form (via bile) into the digestive tract.

Lipid Panel:

Total cholesterol is defined as the sum of LDL, HDL, and VLDL. In general, total blood cholesterol levels <200 mg/dL are considered normal, levels between 200-239 mg/dL are considered borderline-high, and levels >240 mg/dL are considered high.

Since 1988, the National Cholesterol Education Program (NCEP) has issued guidelines identifying LDL as the primary target of cholesterol therapy. The current guidelines, set forth in Adult Treatment Panel-III (ATP-III), set a goal for LDL <100 mg/dL (2.6 mmol/L). Increased LDL is associated with atherosclerotic disease, which confers high risk for coronary heart disease (CHD)-related events, including clinical CHD, symptomatic carotid artery disease, peripheral arterial disease, and abdominal aortic aneurysm. Diseases, disorders and conditions associated with elevated cholesterol levels, and the treatment and/or prevention thereof, are described in detail hereafter.

There is considerable evidence indicating that low levels of high-density cholesterol (HDL-C, or simply HDL) are a contributory factor in the development of atherosclerosis and CHD. Low HDL is one of the most common lipid disorders in patients with premature coronary artery disease. Patients with hypertriglyceridemia usually have lower HDL cholesterol. Certain medications, including beta-blockers, progesterone and testosterone, also lower HDL levels.

In the average man, HDL cholesterol levels range from 40 to 50 mg/dL, whereas in the average woman, they range from 50 to 60 mg/dL. Studies have indicated that the median values of HDL associated with the lowest risk for atherosclerotic events are 62 mg/dL in men and 81 mg/dL in women. The ATP-III guidelines for lipid-lowering therapy established an HDL level below 40 mg/dL as a major positive risk factor and LDL level ≥60 mg/dL as a negative risk factor (i.e., protective). A ratio of total cholesterol to HDL of less than 5:1 is considered to be desirable.

Triglycerides are predominantly carried in the blood stream by very low density lipoproteins (VLDL). There is considerable heterogeneity of triglyceride-rich particles. Triglyceride-rich particles derived from dietary fat—chylomicrons—are not themselves associated with CHD, but, when very high (>1,000 mg/dL) can cause pancreatitis, venous and arterial thrombi, acute heart attack and stroke. However, these chylomicron particles are gradually reduced in size by lipoprotein lipase to intermediate density lipoproteins (IDL) which are atherogenic. Similarly, VLDL from the liver is reduced in size by lipoprotein lipase, producing atherogenic IDL. VLDL is predictive of progression of coronary artery disease and CHD events, and thus hypertriglyceridemia has been increasingly recognized as a risk factor for CHD.

High triglyceride levels either result from genetic causes or are acquired. In terms of genetic causes, about 1/500 people have an inherited tendency towards high plasma triglycerides. Acquired high triglycerides are most commonly associated with excessive alcohol intake, exogenous estrogens or estrogen agonists, poorly controlled diabetes, beta-blockers, corticosteroids, and uremia. Triglycerides levels in excess of 1,000 mg/dL reflect an acquired cause for high triglycerides superimposed on a genetic cause. Less common causes of acquired high triglycerides include kidney failure, nephrotic syndrome, albuminuria, hypothyroidism, many liver diseases, hemochromatosis, hyperparathyroidism, and glycogen storage disease.

According to the American Heart Association, triglyceride levels of less than 150 mg/dL are normal; levels from 150 to 199 mg/dL are borderline high; levels from 200 to 499 mg/dL are high; and levels ≥500 mg/dL are very high. In general, triglyceride levels between 150 and 200 mg/dL are not pharmacologically treated.

Testing:

Several general methods and systems have been used in evaluating a subject's lipid profile. Any method or system, now in existence or subsequently developed, may be used in conjunction with the teachings of the present disclosure.

Fasting cholesterol tests, which generally utilize a colorimetric assay system, are the traditional means for measuring total serum cholesterol. Such tests require blood to be drawn after 12-hour fast to determine a lipoprotein profile. Usually, only the total cholesterol, HDL, and triglycerides are measured; for cost reasons, VLDL is usually estimated as one-fifth of the triglycerides and the LDL is estimated using the Friedewald formula. Although such tests are inexpensive and widely available (e.g., Sigma-Aldrich, St. Louis, Mo.; BioVision, Inc., Milpitas, Calif.), they require fasting and are not as sensitive as other tests because LDL is estimated rather than determined accurately.

When assessing hypercholesterolemia, it is frequently useful to measure all lipoprotein subfractions (VLDL, IDL, LDL and HDL). Because a particular therapeutic goal is to decrease LDL (while maintaining or increasing HDL), cholesterol tests that directly measure LDL levels are more accurate, and they are especially useful for those patients who have elevated triglycerides. Though commercially available (e.g., Beckman Coulter, Inc; Brea, Calif.), use of these direct measurement tests is sometimes limited due to their cost.

Effect of PEG-IL-10 on Cholesterol Homeostasis and Indicators Thereof:

As discussed in the Experimental section, administration of PEG-IL-10 to mice down-regulated expression levels of several hepatic enzymes involved in the cholesterol synthesis pathway (Mevalonate Pathway). In addition, the Experimental section describes the effect in mice of PEG-IL-10 on total serum cholesterol, triglycerides, LDL, HDL and the LDL/HDL ratio. As indicated in FIG. 2, levels of cholesterol (FIG. 2A); triglycerides (FIG. 2B); and LDL (FIG. 2C) were all significantly reduced at each of three doses of PEG-IL-10. Importantly, taken together these data indicate that it is not necessary to exceed a particular PEG-IL-10 dose (~0.2 mg/kg dose in mice) in order to achieve an optimal therapeutic effect. Thus, the more serious adverse effects (e.g., liver toxicity) observed with higher doses can be avoided. Translation of the murine dose to the human dose should lead to comparable results.

Figure 2D:
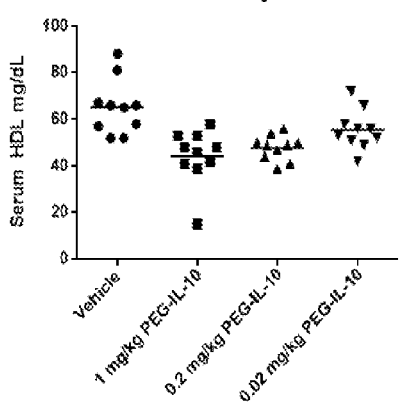

As indicated in FIG. 2D, PEG-IL-10 decreased serum HDL levels compared to vehicle control. According to the historically-accepted dogma that increasing HDL levels is beneficial (e.g., cardioprotective), this result might be considered disadvantageous. However, recent evidence, including that from the AIM-HIGH trial (Atherothrombosis Intervention in Metabolic Syndrome with Low HDL/Triglycerides: Impact on Global Health Outcomes), challenges the notion that any therapeutic agent targeting HDL is necessarily beneficial (see, e.g., Nicholls, (2012) Cleveland Clinic J. Med. 79(1):38-43). Thus, the observation that PEG-IL-10 decreases serum HDL levels might, in fact, be therapeutically irrelevant. Moreover, this result coincides and is not inconsistent with the findings that total serum cholesterol is associated with increased cardiovascular disease risk (see, e.g., Lewington et al., (2005) Circulation 12:3373-74).

Figure 3A:
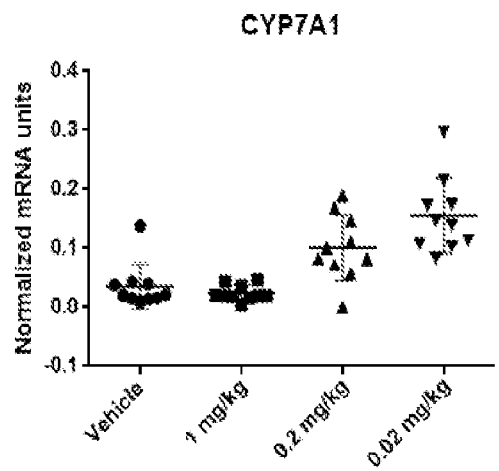
FIGS. 3A-3C depict the effect of PEG-rmIL-10 on regulators of bile acid synthesis, intracellular cholesterol trafficking, and cholesterol efflux (CYP7A1, APOL8 and ABCG1) in LDLR−/− mice fed a high-fat Western diet for four weeks. During weeks three and four, mice were administered PEG-rmIL-10 (1 mg/kg; 0.2 mg/kg; or 0.02 mg/kg) or vehicle control SC daily, after which livers were analyzed for changes in message expression of CYP7A1 (FIG. 3A); APOL8 (FIG. 3B); and ABCG1 (FIG. 3C). (n=10; bars represent the median of the datapoints).
Figure 3B:
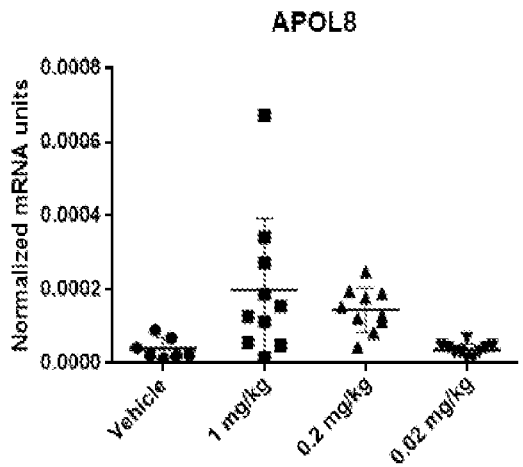

As described in detail in the Experimental section, the effects of PEG-IL-10 administered to mice on regulators of bile acid synthesis (CYP7A1); intracellular cholesterol trafficking (APOL8); and cholesterol efflux (ABCG1), were evaluated. CYP7A1, a cytochrome P450 heme enzyme that oxidizes cholesterol, is the rate-limiting enzyme in the synthesis of bile acid from cholesterol. As depicted in FIG. 3A, PEG-IL-10 increased message expression of CYP7A1, indicating that there is increased efflux of cholesterol from the liver. FIG. 3B shows that increasing doses of PEG-IL-10 correlated with increasing message expression of APOL8, a member of the HDL family that plays a central role in cholesterol transport; as a result, there is greater intracellular cholesterol trafficking and thus more substrate available for efflux. Moreover, IL-10 increased message expression of ABCG1, an efflux molecule involved in preparing cholesterol for removal from the liver as bile salts, which correlates with a reduction in serum cholesterol.

Figure 4A:
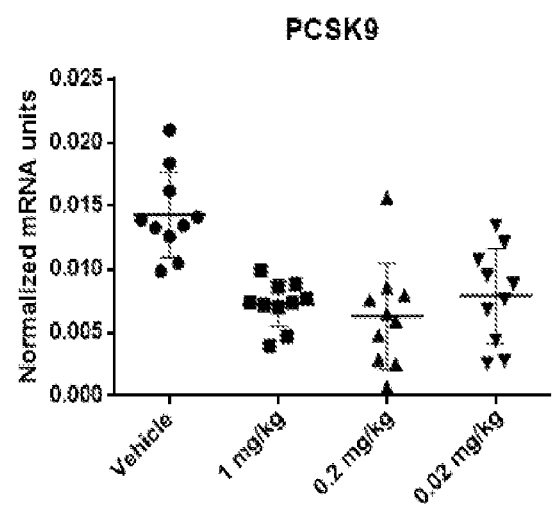
FIGS. 4A and 4B depict the effect of PEG-rmIL-10 on PCSK9 and APOA2, which are involved with regulation of LDL and HDL, respectively. LDLR−/− mice fed were a high-fat Western diet for four weeks. During weeks three and four, mice were administered PEG-rmIL-10 (1 mg/kg; 0.2 mg/kg; or 0.02 mg/kg) or vehicle control SC daily, after which livers were analyzed for changes in message expression of PCSK9 and APOA2. (n=10; bars represent the median of the datapoints).

Furthermore, the effect of PEG-IL-10 administered to mice on PCSK9, a major regulator in cholesterol homeostasis that impacts LDL, was determined. As indicated in FIG. 4A, PEG-IL-10 down-regulated message expression of PCSK9 in knock-out mice lacking the LDL receptor. These data indicate that PEG-IL-10 lowers cholesterol in a non-PCSK9-dependent manner. When administered to these knockout mice, PEG-IL-10 also caused a reduction in the message expression of the HDL particle protein APOA2 (see FIG. 4B). APOA2, which is involved in HDL construction, is the second most abundant protein of the high density lipoprotein particles. Thus, the reduction of APOA2 message expression contributes to hypercholesterolemia through reduction of HDL. However, as discussed elsewhere herein, the beneficial effects of pegylated IL-10 on LDL vastly outweigh any less favorable effects due to HDL reduction; this may be especially true when pegylated IL-10 is administered in combination with another agent(s) having a different mechanism of action.

Figure 5:
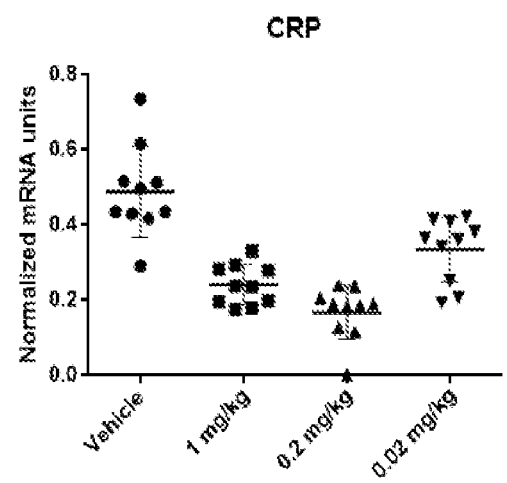
FIG. 5 depicts the effect of PEG-rmIL-10 on regulation of CRP, an indicator of inflammation and/or atherosclerosis, in LDLR−/− mice fed a high-fat Western diet for four weeks. During weeks three and four, mice were administered PEG-rmIL-10 (1 mg/kg; 0.2 mg/kg; or 0.02 mg/kg) or vehicle control SC daily, after which livers were analyzed for changes in message expression of CRP. (n=10; bars represent the median of the datapoints).

The effect of PEG-IL-10 on CRP in LDLR−/− mice was also evaluated. CRP is a member of the class of acute-phase reactants, and its levels rise dramatically during inflammatory processes occurring in the body. High levels of CRP have been associated with cardiovascular risk, largely due to its inflammatory and atherosclerotic effects. As depicted in FIG. 5, administration of PEG-IL-10 reduced CRP message expression, suggesting that IL-10 has a cardioprotective effect.

Figure 6A:
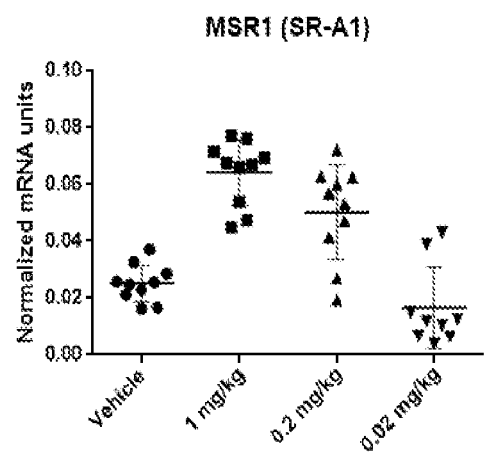
FIGS. 6A and 6B depict the effect of PEG-rmIL-10 on MSR1 and MARCO (Scavenger Receptor-A1 and Scavenger Receptor A-2, respectively), which are associated with the mechanism of cholesterol uptake. LDLR−/− mice were fed a high-fat Western diet for four weeks. During weeks three and four, mice were administered PEG-rmIL-10 (1 mg/kg; 0.2 mg/kg; or 0.02 mg/kg) or vehicle control SC daily, after which livers were analyzed for changes in message expression of MSR1 and MARCO. (n=10; bars represent the median of the datapoints).
Figure 6B:
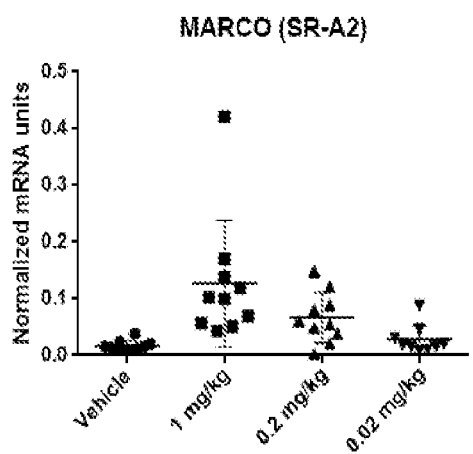

Furthermore, administration of PEG-IL-10 to LDLR−/− mice had a positive effect on several scavenger receptors implicated in cholesterol uptake. MSR1 (also known as SR-A1 (Scavenger Receptor-A1) and CD204 (Cluster of Differentiation 204)), and MARCO (also known as SR-A2 (Scavenger Receptor A-2)), are scavenger receptors that mediate the endocytosis of LDLs and are thus involved in cholesterol uptake. Increased message expression of both scavenger receptors was observed (see FIGS. 6A and 6B), which correlates with enhanced cholesterol uptake and indicates that MSR1 and MARCO are associated with normalizing hypercholesterolemia.

In particular embodiments, an IL-10 agent disclosed herein (e.g., PEG-IL-10) has an anti-hyperlipidemia activity capable of reducing the levels of VLDL, IDL, LDL, or a combination thereof by, e.g., at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90% or at least 95%. In yet other embodiments, an IL-10 agent disclosed herein (e.g., PEG-IL-10) has anti-hyperlipidemia activity capable of reducing the levels of VLDL, IDL, LDL, or a combination thereof in a range from, e.g., about 10% to about 100%, about 20% to about 100%, about 30% to about 100%, about 40% to about 100%, about 50% to about 100%, about 60% to about 100%, about 70% to about 100%, or about 80% to about 100%; about 10% to about 90%, about 20% to about 90%, about 30% to about 90%, about 40% to about 90%, about 50% to about 90%, about 60% to about 90%, about 70% to about 90%; about 10% to about 80%, about 20% to about 80%, about 30% to about 80%, about 40% to about 80%, about 50% to about 80%, or about 60% to about 80%; about 10% to about 70%, about 20% to about 70%, about 30% to about 70%, about 40% to about 70%, or about 50% to about 70%.

In another embodiment of the present disclosure, an IL-10 agent disclosed herein (e.g., PEG-IL-10) increases the level of HDL. In an aspect of this embodiment, the IL-10 agent increases the level of HDL by, e.g., at least 2%, at least 3%, at least 10%, at least 12%, at least 15%, at least 17%, at least 20%, at least 22%, at least 25%, at least 27%, at least 30%, at least 32%, at least 35%, at least 37%, at least 40%, at least 42%, at least 45% or at least 47%. In yet other embodiments of the present disclosure, the IL-10 agent increases the level of HDL in a range from, e.g., about 2% to about 100%; about 10% to about 50%, about 15% to about 50%, about 20% to about 50%, about 25% to about 50%, about 30% to about 50%, about 35% to about 50%, or about 40% to about 50%; about 2% to about 45%, about 10% to about 45%, about 15% to about 45%, about 20% to about 45%, about 25% to about 45%, about 30% to about 45%, or about 35% to about 45%; about 2% to about 40%, about 10% to about 40%, about 15% to about 40%, about 20% to about 40%, about 25% to about 40%, or about 30% to about 40%; about 2% to about 35%, about 10% to about 35%, about 15% to about 35%, about 20% to about 35%, or about 25% to about 35%.

It is to be understood that the aforementioned amounts, ranges, and the like are illustrative rather than limiting.

Methods of Production of IL-10

A polypeptide of the present disclosure can be produced by any suitable method, including non-recombinant (e.g., chemical synthesis) and recombinant methods.

A. Chemical Synthesis

Where a polypeptide is chemically synthesized, the synthesis may proceed via liquid-phase or solid-phase. Solid-phase peptide synthesis (SPPS) allows the incorporation of unnatural amino acids and/or peptide/protein backbone modification. Various forms of SPPS, such as 9-fluorenylmethoxycarbonyl (Fmoc) and t-butyloxycarbonyl (Boc), are available for synthesizing polypeptides of the present disclosure. Details of the chemical syntheses are known in the art (e.g., Ganesan A. (2006) Mini Rev. Med. Chem. 6:3-10; and Camarero J. A. et al., (2005) Protein Pept Lett. 12:723-8).

Solid phase peptide synthesis may be performed as described hereafter. The alpha functions (Nα) and any reactive side chains are protected with acid-labile or base-labile groups. The protective groups are stable under the conditions for linking amide bonds but can readily be cleaved without impairing the peptide chain that has formed. Suitable protective groups for the α-amino function include, but are not limited to, the following: Boc, benzyloxycarbonyl (Z), O-chlorbenzyloxycarbonyl, bi-phenylisopropyloxycarbonyl, tert-amyloxycarbonyl (Amoc), α,α-dimethyl-3,5-dimethoxy-benzyloxycarbonyl, o-nitrosulfenyl, 2-cyano-t-butoxy-carbonyl, Fmoc, 1-(4,4-dimethyl-2,6-dioxocylohex-1-ylidene)ethyl (Dde) and the like.

Suitable side chain protective groups include, but are not limited to: acetyl, allyl (All), allyloxycarbonyl (Alloc), benzyl (Bzl), benzyloxycarbonyl (Z), t-butyloxycarbonyl (Boc), benzyloxymethyl (Bom), o-bromobenzyloxycarbonyl, t-butyl (tBu), t-butyldimethylsilyl, 2-chlorobenzyl, 2-chlorobenzyloxycarbonyl, 2,6-dichlorobenzyl, cyclohexyl, cyclopentyl, 1-(4,4-dimethyl-2,6-dioxocyclohex-1-ylidene)ethyl (Dde), isopropyl, 4-methoxy-2,3-6-trimethylbenzylsulfonyl (Mtr), 2,3,5,7,8-pentamethylchroman-6-sulfonyl (Pmc), pivalyl, tetrahydropyran-2-yl, tosyl (Tos), 2,4,6-trimethoxybenzyl, trimethylsilyl and trityl (Trt).

In the solid phase synthesis, the C-terminal amino acid is coupled to a suitable support material. Suitable support materials are those which are inert towards the reagents and reaction conditions for the step-wise condensation and cleavage reactions of the synthesis process and which do not dissolve in the reaction media being used. Examples of commercially-available support materials include styrene/divinylbenzene copolymers which have been modified with reactive groups and/or polyethylene glycol; chloromethylated styrene/divinylbenzene copolymers; hydroxymethylated or aminomethylated styrene/divinylbenzene copolymers; and the like. When preparation of the peptidic acid is desired, polystyrene (1%)-divinylbenzene or TentaGel® derivatized with 4-benzyloxybenzyl-alcohol (Wang-anchor) or 2-chlorotrityl chloride can be used. In the case of the peptide amide, polystyrene (1%) divinylbenzene or TentaGel® derivatized with 5-(4'-aminomethyl)-3',5'-dimethoxyphenoxy)valeric acid (PAL-anchor) or p-(2,4-dimethoxyphenyl-amino methyl)-phenoxy group (Rink amide anchor) can be used.

The linkage to the polymeric support can be achieved by reacting the C-terminal Fmoc-protected amino acid with the support material by the addition of an activation reagent in ethanol, acetonitrile, N,N-dimethylformamide (DMF), dichloromethane, tetrahydrofuran, N-methylpyrrolidone or similar solvents at room temperature or elevated temperatures (e.g., between 40° C. and 60° C.) and with reaction times of, e.g., 2 to 72 hours.

The coupling of the Nα-protected amino acid (e.g., the Fmoc amino acid) to the PAL, Wang or Rink anchor can, for example, be carried out with the aid of coupling reagents such as N,N'-dicyclohexylcarbodiimide (DCC), N,N'-diisopropylcarbodiimide (DIC) or other carbodiimides, 2-(1H-benzotriazol-1-yl)-1,1,3,3-tetramethyluronium tetrafluoroborate (TBTU) or other uronium salts, O-acyl-ureas, benzotriazol-1-yl-tris-pyrrolidino-phosphonium hexafluorophosphate (PyBOP) or other phosphonium salts, N-hydroxysuccinimides, other N-hydroxyimides or oximes in the presence or absence of 1-hydroxybenzotriazole or 1-hydroxy-7-azabenzotriazole, e.g., with the aid of TBTU with addition of HOBt, with or without the addition of a base such as, for example, diisopropylethylamine (DIEA), triethylamine or N-methylmorpholine, e.g., diisopropylethylamine with reaction times of 2 to 72 hours (e.g., 3 hours in a 1.5 to 3-fold excess of the amino acid and the coupling reagents, for example, in a 2-fold excess and at temperatures between about 10° C. and 50° C., for example, 25° C. in a solvent such as dimethylformamide, N-methylpyrrolidone or dichloromethane, e.g., dimethylformamide).

Instead of the coupling reagents, it is also possible to use the active esters (e.g., pentafluorophenyl, p-nitrophenyl or the like), the symmetric anhydride of the Nα-Fmoc-amino acid, its acid chloride or acid fluoride, under the conditions described above.

The Nα-protected amino acid (e.g., the Fmoc amino acid) can be coupled to the 2-chlorotrityl resin in dichloromethane with the addition of DIEA and having reaction times of 10 to 120 minutes, e.g., 20 minutes, but is not limited to the use of this solvent and this base.

The successive coupling of the protected amino acids can be carried out according to conventional methods in peptide synthesis, typically in an automated peptide synthesizer. After cleavage of the Nα-Fmoc protective group of the coupled amino acid on the solid phase by treatment with, e.g., piperidine (10% to 50%) in dimethylformamide for 5 to 20 minutes, e.g., 2×2 minutes with 50% piperidine in DMF and 1×15 minutes with 20% piperidine in DMF, the next protected amino acid in a 3 to 10-fold excess, e.g., in a 10-fold excess, is coupled to the previous amino acid in an inert, non-aqueous, polar solvent such as dichloromethane, DMF or mixtures of the two and at temperatures between about 10° C. and 50° C., e.g., at 25° C. The previously mentioned reagents for coupling the first Nα-Fmoc amino acid to the PAL, Wang or Rink anchor are suitable as coupling reagents. Active esters of the protected amino acid, or chlorides or fluorides or symmetric anhydrides thereof can also be used as an alternative.

At the end of the solid phase synthesis, the peptide is cleaved from the support material while simultaneously cleaving the side chain protecting groups. Cleavage can be carried out with trifluoroacetic acid or other strongly acidic media with addition of 5%-20% V/V of scavengers such as dimethylsulfide, ethylmethylsulfide, thioanisole, thiocresol, m-cresol, anisole ethanedithiol, phenol or water, e.g., 15% v/v dimethylsulfide/ethanedithiol/m-cresol 1:1:1, within 0.5 to 3 hours, e.g., 2 hours. Peptides with fully protected side chains are obtained by cleaving the 2-chlorotrityl anchor with glacial acetic acid/trifluoroethanol/dichloromethane 2:2:6. The protected peptide can be purified by chromatography on silica gel. If the peptide is linked to the solid phase via the Wang anchor and if it is intended to obtain a peptide with a C-terminal alkylamidation, the cleavage can be carried out by aminolysis with an alkylamine or fluoroalkylamine. The aminolysis is carried out at temperatures between about −10° C. and 50° C. (e.g., about 25° C.), and reaction times between about 12 and 24 hours (e.g., about 18 hours). In addition the peptide can be cleaved from the support by re-esterification, e.g., with methanol.

The acidic solution that is obtained may be admixed with a 3 to 20-fold amount of cold ether or n-hexane, e.g., a 10-fold excess of diethyl ether, in order to precipitate the peptide and hence to separate the scavengers and cleaved protective groups that remain in the ether. A further purification can be carried out by re-precipitating the peptide several times from glacial acetic acid. The precipitate that is obtained can be taken up in water or tert-butanol or mixtures of the two solvents, e.g., a 1:1 mixture of tert-butanol/water, and freeze-dried.

The peptide obtained can be purified by various chromatographic methods, including ion exchange over a weakly basic resin in the acetate form; hydrophobic adsorption chromatography on non-derivatized polystyrene/divinylbenzene copolymers (e.g., Amberlite® XAD); adsorption chromatography on silica gel; ion exchange chromatography, e.g., on carboxymethyl cellulose; distribution chromatography, e.g., on Sephadex® G-25; countercurrent distribution chromatography; or high pressure liquid chromatography (HPLC) e.g., reversed-phase HPLC on octyl or octadecylsilylsilica (ODS) phases.

B. Recombinant Production

Methods describing the preparation of human and mouse IL-10 can be found in, for example, U.S. Pat. No. 5,231,012, which teaches methods for the production of proteins having IL-10 activity, including recombinant and other synthetic techniques. IL-10 can be of viral origin, and the cloning and expression of a viral IL-10 from Epstein Barr virus (BCRF1 protein) is disclosed in Moore et al., (1990) Science 248: 1230. IL-10 can be obtained in a number of ways using standard techniques known in the art, such as those described herein. Recombinant human IL-10 is also commercially available, e.g., from PeproTech, Inc., Rocky Hill, N.J.

Where a polypeptide is produced using recombinant techniques, the polypeptide may be produced as an intracellular protein or as a secreted protein, using any suitable construct and any suitable host cell, which can be a prokaryotic or eukaryotic cell, such as a bacterial (e.g., *E. coli*) or a yeast host cell, respectively. Other examples of eukaryotic cells that may be used as host cells include insect cells, mammalian cells, and/or plant cells. Where mammalian host cells are used, they may include human cells (e.g., HeLa, 293, H9 and Jurkat cells); mouse cells (e.g., NIH3T3, L cells, and C127 cells); primate cells (e.g., Cos 1, Cos 7 and CV 1); and hamster cells (e.g., Chinese hamster ovary (CHO) cells).

A variety of host-vector systems suitable for the expression of a polypeptide may be employed according to standard procedures known in the art. See, e.g., Sambrook et al., 1989 Current Protocols in Molecular Biology Cold Spring Harbor Press, New York; and Ausubel et al. 1995 Current Protocols in Molecular Biology, Eds. Wiley and Sons. Methods for introduction of genetic material into host cells include, for example, transformation, electroporation, conjugation, calcium phosphate methods and the like. The method for transfer can be selected so as to provide for stable expression of the introduced polypeptide-encoding nucleic acid. The polypeptide-encoding nucleic acid can be provided as an inheritable episomal element (e.g., a plasmid) or can be genomically integrated. A variety of appropriate vectors for use in production of a polypeptide of interest are commercially available.

Vectors can provide for extrachromosomal maintenance in a host cell or can provide for integration into the host cell genome. The expression vector provides transcriptional and translational regulatory sequences, and may provide for inducible or constitutive expression where the coding region is operably-linked under the transcriptional control of the transcriptional initiation region, and a transcriptional and translational termination region. In general, the transcriptional and translational regulatory sequences may include, but are not limited to, promoter sequences, ribosomal binding sites, transcriptional start and stop sequences, translational start and stop sequences, and enhancer or activator sequences. Promoters can be either constitutive or inducible, and can be a strong constitutive promoter (e.g., T7).

Expression constructs generally have convenient restriction sites located near the promoter sequence to provide for the insertion of nucleic acid sequences encoding proteins of interest. A selectable marker operative in the expression host may be present to facilitate selection of cells containing the vector. Moreover, the expression construct may include additional elements. For example, the expression vector may have one or two replication systems, thus allowing it to be maintained in organisms, for example, in mammalian or insect cells for expression and in a prokaryotic host for cloning and amplification. In addition, the expression construct may contain a selectable marker gene to allow the selection of transformed host cells. Selectable genes are well known in the art and will vary with the host cell used.

Isolation and purification of a protein can be accomplished according to methods known in the art. For example, a protein can be isolated from a lysate of cells genetically modified to express the protein constitutively and/or upon induction, or from a synthetic reaction mixture by immunoaffinity purification, which generally involves contacting the sample with an anti-protein antibody, washing to remove non-specifically bound material, and eluting the specifically bound protein. The isolated protein can be further purified by dialysis and other methods normally employed in protein purification. In one embodiment, the protein may be isolated using metal chelate chromatography methods. Proteins may contain modifications to facilitate isolation.

The polypeptides may be prepared in substantially pure or isolated form (e.g., free from other polypeptides). The polypeptides can be present in a composition that is enriched for the polypeptide relative to other components that may be present (e.g., other polypeptides or other host cell components). For example, purified polypeptide may be provided such that the polypeptide is present in a composition that is substantially free of other expressed proteins, e.g., less than about 90%, less than about 60%, less than about 50%, less than about 40%, less than about 30%, less than about 20%, less than about 10%, less than about 5%, or less than about 1%.

An IL-10 polypeptide may be generated using recombinant techniques to manipulate different IL-10-related nucleic acids known in the art to provide constructs capable of encoding the IL-10 polypeptide. It will be appreciated that, when provided a particular amino acid sequence, the ordinary skilled artisan will recognize a variety of different nucleic acid molecules encoding such amino acid sequence in view of her background and experience in, for example, molecular biology.

Amide Bond Substitutions

In some cases, IL-10 includes one or more linkages other than peptide bonds, e.g., at least two adjacent amino acids are joined via a linkage other than an amide bond. For example, in order to reduce or eliminate undesired proteolysis or other means of degradation, and/or to increase serum stability, and/or to restrict or increase conformational flexibility, one or more amide bonds within the backbone of IL-10 can be substituted.

In another example, one or more amide linkages (—CO—NH—) in IL-10 can be replaced with a linkage which is an isostere of an amide linkage, such as —CH$_2$NH—, —CH$_2$S—, —CH$_2$CH$_2$—, —CH=CH-(cis and trans), —COCH$_2$—, —CH(OH)CH$_2$— or —CH$_2$SO—. One or more amide linkages in IL-10 can also be replaced by, for example, a reduced isostere pseudopeptide bond. See Couder et al. (1993) Int. J. Peptide Protein Res. 41:181-184. Such replacements and how to effect them are known to those of ordinary skill in the art.

Amino Acid Substitutions

One or more amino acid substitutions can be made in an IL-10 polypeptide. The following are non-limiting examples:

a) substitution of alkyl-substituted hydrophobic amino acids, including alanine, leucine, isoleucine, valine, norleucine, (S)-2-aminobutyric acid, (S)-cyclohexylalanine or other simple alpha-amino acids substituted by an aliphatic side chain from C1-C10 carbons including branched, cyclic and straight chain alkyl, alkenyl or alkynyl substitutions;

b) substitution of aromatic-substituted hydrophobic amino acids, including phenylalanine, tryptophan, tyrosine, sulfotyrosine, biphenylalanine, 1-naphthylalanine, 2-naphthylalanine, 2-benzothienylalanine, 3-benzothienylalanine, histidine, including amino, alkylamino, dialkylamino, aza, halogenated (fluoro, chloro, bromo, or iodo) or alkoxy (from C$_1$-C$_4$)-substituted forms of the above-listed aromatic amino acids, illustrative examples of which are: 2-, 3- or 4-aminophenylalanine, 2-, 3- or 4-chlorophenylalanine, 2-, 3- or 4-methylphenylalanine, 2-, 3- or 4-methoxyphenylalanine, 5-amino-, 5-chloro-, 5-methyl- or 5-methoxytryptophan, 2'-, 3'-, or 4'-amino-, 2'-, 3'-, or 4'-chloro-, 2, 3, or 4-biphenylalanine, 2'-, 3'-, or 4'-methyl-, 2-, 3- or 4-biphenylalanine, and 2- or 3-pyridylalanine;

c) substitution of amino acids containing basic side chains, including arginine, lysine, histidine, ornithine, 2,3-diaminopropionic acid, homoarginine, including alkyl, alkenyl, or aryl-substituted (from $C_1$-$C_{10}$ branched, linear, or cyclic) derivatives of the previous amino acids, whether the substituent is on the heteroatoms (such as the alpha nitrogen, or the distal nitrogen or nitrogens, or on the alpha carbon, in the pro-R position for example. Compounds that serve as illustrative examples include: N-epsilon-isopropyl-lysine, 3-(4-tetrahydropyridyl)-glycine, 3-(4-tetrahydropyridyl)-alanine, N,N-gamma, gamma'-diethyl-homoarginine. Included also are compounds such as alpha-methyl-arginine, alpha-methyl-2,3-diaminopropionic acid, alpha-methyl-histidine, alpha-methyl-ornithine where the alkyl group occupies the pro-R position of the alpha-carbon. Also included are the amides formed from alkyl, aromatic, heteroaromatic (where the heteroaromatic group has one or more nitrogens, oxygens or sulfur atoms singly or in combination), carboxylic acids or any of the many well-known activated derivatives such as acid chlorides, active esters, active azolides and related derivatives, and lysine, ornithine, or 2,3-diaminopropionic acid;

d) substitution of acidic amino acids, including aspartic acid, glutamic acid, homoglutamic acid, tyrosine, alkyl, aryl, arylalkyl, and heteroaryl sulfonamides of 2,4-diaminopripionic acid, ornithine or lysine and tetrazole-substituted alkyl amino acids;

e) substitution of side chain amide residues, including asparagine, glutamine, and alkyl or aromatic substituted derivatives of asparagine or glutamine; and f) substitution of hydroxyl-containing amino acids, including serine, threonine, homoserine, 2,3-diaminopropionic acid, and alkyl or aromatic substituted derivatives of serine or threonine.

In some cases, IL-10 comprises one or more naturally occurring non-genetically encoded L-amino acids, synthetic L-amino acids, or D-enantiomers of an amino acid. For example, IL-10 can comprise only D-amino acids. For example, an IL-10 polypeptide can comprise one or more of the following residues: hydroxyproline, β-alanine, o-aminobenzoic acid, m-aminobenzoic acid, p-aminobenzoic acid, m-aminomethylbenzoic acid, 2,3-diaminopropionic acid, α-aminoisobutyric acid, N-methylglycine (sarcosine), ornithine, citrulline, t-butylalanine, t-butylglycine, N-methylisoleucine, phenylglycine, cyclohexylalanine, norleucine, naphthylalanine, pyridylalanine 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylic acid, β-2-thienylalanine, methionine sulfoxide, homoarginine, N-acetyl lysine, 2,4-diamino butyric acid, rho-aminophenylalanine, N-methylvaline, homocysteine, homoserine, ε-amino hexanoic acid, ω-aminohexanoic acid, ω-aminoheptanoic acid, ω-aminooctanoic acid, ω-aminodecanoic acid, ω-aminotetradecanoic acid, cyclohexylalanine, α,γ-diaminobutyric acid, α,β-diaminopropionic acid, δ-amino valeric acid, and 2,3-diaminobutyric acid.

Additional Modifications

A cysteine residue or a cysteine analog can be introduced into an IL-10 polypeptide to provide for linkage to another peptide via a disulfide linkage or to provide for cyclization of the IL-10 polypeptide. Methods of introducing a cysteine or cysteine analog are known in the art; see, e.g., U.S. Pat. No. 8,067,532.

An IL-10 polypeptide can be cyclized. One or more cysteines or cysteine analogs can be introduced into an IL-10 polypeptide, where the introduced cysteine or cysteine analog can form a disulfide bond with a second introduced cysteine or cysteine analog. Other means of cyclization include introduction of an oxime linker or a lanthionine linker; see, e.g., U.S. Pat. No. 8,044,175. Any combination of amino acids (or non-amino acid moieties) that can form a cyclizing bond can be used and/or introduced. A cyclizing bond can be generated with any combination of amino acids (or with an amino acid and —$(CH2)_n$—CO— or —$(CH2)_n$—$C_6H_4$—CO—) with functional groups which allow for the introduction of a bridge. Some examples are disulfides, disulfide mimetics such as the —$(CH2)_n$— carba bridge, thioacetal, thioether bridges (cystathionine or lanthionine) and bridges containing esters and ethers. In these examples, n can be any integer, but is frequently less than ten.

Other modifications include, for example, an N-alkyl (or aryl) substitution (ψ[CONR]), or backbone crosslinking to construct lactams and other cyclic structures. Other derivatives include C-terminal hydroxymethyl derivatives, o-modified derivatives (e.g., C-terminal hydroxymethyl benzyl ether), N-terminally modified derivatives including substituted amides such as alkylamides and hydrazides.

In some cases, one or more L-amino acids in an IL-10 polypeptide is replaced with one or more D-amino acids.

In some cases, an IL-10 polypeptide is a retroinverso analog (see, e.g., Sela and Zisman (1997) FASEB J. 11:449). Retro-inverso peptide analogs are isomers of linear polypeptides in which the direction of the amino acid sequence is reversed (retro) and the chirality, D- or L-, of one or more amino acids therein is inverted (inverso), e.g., using D-amino acids rather than L-amino acids. [See, e.g., Jameson et al. (1994) Nature 368:744; and Brady et al. (1994) Nature 368:692].

An IL-10 polypeptide can include a "Protein Transduction Domain" (PTD), which refers to a polypeptide, polynucleotide, carbohydrate, or organic or inorganic molecule that facilitates traversing a lipid bilayer, micelle, cell membrane, organelle membrane, or vesicle membrane. A PTD attached to another molecule facilitates the molecule traversing a membrane, for example going from extracellular space to intracellular space, or cytosol to within an organelle. In some embodiments, a PTD is covalently linked to the amino terminus of an IL-10 polypeptide, while in other embodiments, a PTD is covalently linked to the carboxyl terminus of an IL-10 polypeptide. Exemplary protein transduction domains include, but are not limited to, a minimal undecapeptide protein transduction domain (corresponding to residues 47-57 of HIV-1 TAT comprising YGRKKRRQRRR; SEQ ID NO:3); a polyarginine sequence comprising a number of arginine residues sufficient to direct entry into a cell (e.g., 3, 4, 5, 6, 7, 8, 9, 10, or 10-50 arginines); a VP22 domain (Zender et al. (2002) Cancer Gene Ther. 9(6):489-96); a *Drosophila Antennapedia* protein transduction domain (Noguchi et al. (2003) Diabetes 52(7):1732-1737); a truncated human calcitonin peptide (Trehin et al. (2004) Pharm. Research 21:1248-1256); polylysine (Wender et al. (2000) Proc. Natl. Acad. Sci. USA 97:13003-13008); RRQRRTSKLMKR (SEQ ID NO:4); Transportan GWTLNSAGYLLGKINLKALAALAKKIL (SEQ ID NO:5); KALAWEAKLAKALAKALAKHLAKALAKALKCEA (SEQ ID NO:6); and RQIKIWFQNRRMKWKK (SEQ ID NO:7). Exemplary PTDs include, but are not limited to, YGRKKRRQRRR (SEQ ID NO:3), RKKRRQRRR (SEQ ID NO:8); an arginine homopolymer of from 3 arginine residues to 50 arginine residues; exemplary PTD domain amino acid sequences include, but are not limited to, any of the following: YGRKKRRQRRR (SEQ ID NO:3); RKKRRQRR (SEQ ID NO:9); YARAAARQARA (SEQ ID NO:10); THRLPRRRRRR (SEQ ID NO:11); and GGRRARRRRRR (SEQ ID NO:12).

The carboxyl group $COR_3$ of the amino acid at the C-terminal end of an IL-10 polypeptide can be present in a free form ($R_3$=OH) or in the form of a physiologically-tolerated alkaline or alkaline earth salt such as, e.g., a sodium, potassium or calcium salt. The carboxyl group can also be esterified with primary, secondary or tertiary alcohols such as, e.g., methanol, branched or unbranched $C_1$-$C_6$-alkyl alcohols, e.g., ethyl alcohol or tert-butanol. The carboxyl group can also be amidated with primary or secondary amines such as ammonia, branched or unbranched $C_1$-$C_6$-alkylamines or $C_1$-$C_6$ di-alkylamines, e.g., methylamine or dimethylamine.

The amino group of the amino acid $NR_1R_2$ at the N-terminus of an IL-10 polypeptide can be present in a free form ($R_1$=H and $R_2$=H) or in the form of a physiologically-tolerated salt such as, e.g., a chloride or acetate. The amino group can also be acetylated with acids such that $R_1$=H and $R_2$=acetyl, trifluoroacetyl, or adamantyl. The amino group can be present in a form protected by amino-protecting groups conventionally used in peptide chemistry, such as those provided above (e.g., Fmoc, Benzyloxy-carbonyl (Z), Boc, and Alloc). The amino group can be N-alkylated in which $R_1$ and/or $R_2$=$C_1$-$C_6$ alkyl or $C_2$-$C_8$ alkenyl or $C_7$-$C_9$ aralkyl. Alkyl residues can be straight-chained, branched or cyclic (e.g., ethyl, isopropyl and cyclohexyl, respectively).

Particular Modifications to Enhance and/or Mimic IL-10 Function

It is frequently beneficial, and sometimes imperative, to improve one of more physical properties of the treatment modalities disclosed herein (e.g., IL-10) and/or the manner in which they are administered. Improvements of physical properties include, for example, modulating immunogenicity; methods of increasing water solubility, bioavailability, serum half-life, and/or therapeutic half-life; and/or modulating biological activity. Certain modifications may also be useful to, for example, raise of antibodies for use in detection assays (e.g., epitope tags) and to provide for ease of protein purification. Such improvements must generally be imparted without adversely impacting the bioactivity of the treatment modality and/or increasing its immunogenicity.

Pegylation of IL-10 is one particular modification contemplated by the present disclosure, while other modifications include, but are not limited to, glycosylation (N- and O-linked); polysialylation; albumin fusion molecules comprising serum albumin (e.g., human serum albumin (HSA), cyno serum albumin, or bovine serum albumin (BSA)); albumin binding through, for example a conjugated fatty acid chain (acylation); and Fc-fusion proteins.

Pegylation:

The clinical effectiveness of protein therapeutics is often limited by short plasma half-life and susceptibility to protease degradation. Studies of various therapeutic proteins (e.g., filgrastim) have shown that such difficulties may be overcome by various modifications, including conjugating or linking the polypeptide sequence to any of a variety of nonproteinaceous polymers, e.g., polyethylene glycol (PEG), polypropylene glycol, or polyoxyalkylenes. This is frequently effected by a linking moiety covalently bound to both the protein and the nonproteinaceous polymer, e.g., a PEG. Such PEG-conjugated biomolecules have been shown to possess clinically useful properties, including better physical and thermal stability, protection against susceptibility to enzymatic degradation, increased solubility, longer in vivo circulating half-life and decreased clearance, reduced immunogenicity and antigenicity, and reduced toxicity.

In addition to the beneficial effects of pegylation on pharmacokinetic parameters, pegylation itself may enhance activity. For example, PEG-IL-10 has been shown to be more efficacious against certain cancers than unpegylated IL-10 (see, e.g., EP 206636A2).

PEGs suitable for conjugation to a polypeptide sequence are generally soluble in water at room temperature, and have the general formula $R(O-CH_2-CH_2)_nO-R$, where R is hydrogen or a protective group such as an alkyl or an alkanol group, and where n is an integer from 1 to 1000. When R is a protective group, it generally has from 1 to 8 carbons. The PEG conjugated to the polypeptide sequence can be linear or branched. Branched PEG derivatives, "star-PEGs" and multi-armed PEGs are contemplated by the present disclosure. A molecular weight of the PEG used in the present disclosure is not restricted to any particular range, and examples are set forth elsewhere herein; by way of example, certain embodiments have molecular weights between 5 kDa and 20 kDa, while other embodiments have molecular weights between 4 kDa and 10 kDa.

The present disclosure also contemplates compositions of conjugates wherein the PEGs have different n values, and thus the various different PEGs are present in specific ratios. For example, some compositions comprise a mixture of conjugates where n=1, 2, 3 and 4. In some compositions, the percentage of conjugates where n=1 is 18-25%, the percentage of conjugates where n=2 is 50-66%, the percentage of conjugates where n=3 is 12-16%, and the percentage of conjugates where n=4 is up to 5%. Such compositions can be produced by reaction conditions and purification methods know in the art. Exemplary reaction conditions are described throughout the specification. Cation exchange chromatography may be used to separate conjugates, and a fraction is then identified which contains the conjugate having, for example, the desired number of PEGs attached, purified free from unmodified protein sequences and from conjugates having other numbers of PEGs attached.

Pegylation most frequently occurs at the alpha amino group at the N-terminus of the polypeptide, the epsilon amino group on the side chain of lysine residues, and the imidazole group on the side chain of histidine residues. Since most recombinant polypeptides possess a single alpha and a number of epsilon amino and imidazole groups, numerous positional isomers can be generated depending on the linker chemistry. General pegylation strategies known in the art can be applied herein. PEG may be bound to a polypeptide of the present disclosure via a terminal reactive group (a "spacer") which mediates a bond between the free amino or carboxyl groups of one or more of the polypeptide sequences and polyethylene glycol. The PEG having the spacer which may be bound to the free amino group includes N-hydroxysuccinylimide polyethylene glycol which may be prepared by activating succinic acid ester of polyethylene glycol with N-hydroxysuccinylimide. Another activated polyethylene glycol which may be bound to a free amino group is 2,4-bis(O-methoxypolyethyleneglycol)-6-chloro-s-triazine, which may be prepared by reacting polyethylene glycol monomethyl ether with cyanuric chloride. The activated polyethylene glycol which is bound to the free carboxyl group includes polyoxyethylenediamine.

Conjugation of one or more of the polypeptide sequences of the present disclosure to PEG having a spacer may be carried out by various conventional methods. For example, the conjugation reaction can be carried out in solution at a pH of from 5 to 10, at temperature from 4° C. to room temperature, for 30 minutes to 20 hours, utilizing a molar ratio of reagent to protein of from 4:1 to 30:1. Reaction conditions may be selected to direct the reaction towards producing predominantly a desired degree of substitution. In general, low temperature, low pH (e.g., pH=5), and short reaction time tend to decrease the number of PEGs attached, whereas high temperature, neutral to high pH (e.g., pH≥7), and longer reaction time tend to increase the number of PEGs attached. Various means known in the art may be used to terminate the reaction. In some embodiments the reaction is terminated by acidifying the reaction mixture and freezing at, e.g., −20° C. Pegylation of various molecules is discussed in, for example, U.S. Pat. Nos. 5,252,714; 5,643,575; 5,919,455; 5,932,462; and 5,985,263. PEG-IL-10 is described in, e.g., U.S. Pat. No. 7,052,686. Specific reaction conditions contemplated for use herein are set forth in the Experimental section.

The present disclosure also contemplates the use of PEG mimetics. Recombinant PEG mimetics have been developed that retain the attributes of PEG (e.g., enhanced serum half-life) while conferring several additional advantageous properties. By way of example, simple polypeptide chains (comprising, for example, Ala, Glu, Gly, Pro, Ser and Thr) capable of forming an extended conformation similar to PEG can be produced recombinantly already fused to the peptide or protein drug of interest (e.g., Amunix' XTEN technology; Mountain View, Calif.). This obviates the need for an additional conjugation step during the manufacturing process. Moreover, established molecular biology techniques enable control of the side chain composition of the polypeptide chains, allowing optimization of immunogenicity and manufacturing properties.

Glycosylation:

For purposes of the present disclosure, "glycosylation" is meant to broadly refer to the enzymatic process that attaches glycans to proteins, lipids or other organic molecules. The use of the term "glycosylation" in conjunction with the present disclosure is generally intended to mean adding or deleting one or more carbohydrate moieties (either by removing the underlying glycosylation site or by deleting the glycosylation by chemical and/or enzymatic means), and/or adding one or more glycosylation sites that may or may not be present in the native sequence. In addition, the phrase includes qualitative changes in the glycosylation of the native proteins involving a change in the nature and proportions of the various carbohydrate moieties present.

Glycosylation can dramatically affect the physical properties (e.g., solubility) of polypeptides such as IL-10 and can also be important in protein stability, secretion, and subcellular localization. Glycosylated polypeptides may also exhibit enhanced stability or may improve one or more pharmacokinetic properties, such as half-life. In addition, solubility improvements can, for example, enable the generation of formulations more suitable for pharmaceutical administration than formulations comprising the non-glycosylated polypeptide.

Addition of glycosylation sites can be accomplished by altering the amino acid sequence. The alteration to the polypeptide may be made, for example, by the addition of, or substitution by, one or more serine or threonine residues (for O-linked glycosylation sites) or asparagine residues (for N-linked glycosylation sites). The structures of N-linked and O-linked oligosaccharides and the sugar residues found in each type may be different. One type of sugar that is commonly found on both is N-acetylneuraminic acid (hereafter referred to as sialic acid). Sialic acid is usually the terminal residue of both N-linked and O-linked oligosaccharides and, by virtue of its negative charge, may confer acidic properties to the glycoprotein. A particular embodiment of the present disclosure comprises the generation and use of N-glycosylation variants.

The polypeptide sequences of the present disclosure may optionally be altered through changes at the nucleic acid level, particularly by mutating the nucleic acid encoding the polypeptide at preselected bases such that codons are generated that will translate into the desired amino acids.

Polysialylation:

The present disclosure also contemplates the use of polysialylation, the conjugation of polypeptides to the naturally occurring, biodegradable α-(2→8) linked polysialic acid ("PSA") in order to improve the polypeptides' stability and in vivo pharmacokinetics.

Albumin Fusion:

Additional suitable components and molecules for conjugation include albumins such as human serum albumin (HSA), cyno serum albumin, and bovine serum albumin (BSA).

According to the present disclosure, albumin may be conjugated to a drug molecule (e.g., a polypeptide described herein) at the carboxyl terminus, the amino terminus, both the carboxyl and amino termini, and internally (see, e.g., U.S. Pat. No. 5,876,969 and U.S. Pat. No. 7,056,701).

In the HSA-drug molecule conjugates contemplated by the present disclosure, various forms of albumin may be used, such as albumin secretion pre-sequences and variants thereof, fragments and variants thereof, and HSA variants. Such forms generally possess one or more desired albumin activities. In additional embodiments, the present disclosure involves fusion proteins comprising a polypeptide drug molecule fused directly or indirectly to albumin, an albumin fragment, and albumin variant, etc., wherein the fusion protein has a higher plasma stability than the unfused drug molecule and/or the fusion protein retains the therapeutic activity of the unfused drug molecule. In some embodiments, the indirect fusion is effected by a linker, such as a peptide linker or modified version thereof.

As alluded to above, fusion of albumin to one or more polypeptides of the present disclosure can, for example, be achieved by genetic manipulation, such that the nucleic acid coding for HSA, or a fragment thereof, is joined to the nucleic acid coding for the one or more polypeptide sequences.

Alternative Albumin Binding Strategies:

Several albumin-binding strategies have been developed as alternatives to direct fusion and may be used with the IL-10 agents described herein. By way of example, the present disclosure contemplates albumin binding through a conjugated fatty acid chain (acylation) and fusion proteins which comprise an albumin binding domain (ABD) polypeptide sequence and the sequence of one or more of the polypeptides described herein.

Conjugation with Other Molecules:

Additional suitable components and molecules for conjugation include, for example, thyroglobulin; tetanus toxoid; Diphtheria toxoid; polyamino acids such as poly(D-lysine: D-glutamic acid); VP6 polypeptides of rotaviruses; influenza virus hemaglutinin, influenza virus nucleoprotein; Keyhole Limpet Hemocyanin (KLH); and hepatitis B virus core protein and surface antigen; or any combination of the foregoing.

Thus, the present disclosure contemplates conjugation of one or more additional components or molecules at the N- and/or C-terminus of a polypeptide sequence, such as another polypeptide (e.g., a polypeptide having an amino acid sequence heterologous to the subject polypeptide), or a carrier molecule. Thus, an exemplary polypeptide sequence can be provided as a conjugate with another component or molecule.

An IL-10 polypeptide may also be conjugated to large, slowly metabolized macromolecules such as proteins; polysaccharides, such as sepharose, agarose, cellulose, or cellulose beads; polymeric amino acids such as polyglutamic acid, or polylysine; amino acid copolymers; inactivated virus particles; inactivated bacterial toxins such as toxoid from diphtheria, tetanus, cholera, or leukotoxin molecules; inactivated bacteria; and dendritic cells. Such conjugated forms, if desired, can be used to produce antibodies against a polypeptide of the present disclosure.

Additional candidate components and molecules for conjugation include those suitable for isolation or purification. Particular non-limiting examples include binding molecules, such as biotin (biotin-avidin specific binding pair), an antibody, a receptor, a ligand, a lectin, or molecules that comprise a solid support, including, for example, plastic or polystyrene beads, plates or beads, magnetic beads, test strips, and membranes.

Fc-Fusion Molecules:

In certain embodiments, the amino- or carboxyl-terminus of a polypeptide sequence of the present disclosure can be fused with an immunoglobulin Fc region (e.g., human Fc) to form a fusion conjugate (or fusion molecule). Fc fusion conjugates have been shown to increase the systemic half-life of biopharmaceuticals, and thus the biopharmaceutical product may require less frequent administration.

Fc binds to the neonatal Fc receptor (FcRn) in endothelial cells that line the blood vessels, and, upon binding, the Fc fusion molecule is protected from degradation and re-released into the circulation, keeping the molecule in circulation longer. This Fc binding is believed to be the mechanism by which endogenous IgG retains its long plasma half-life. More recent Fc-fusion technology links a single copy of a biopharmaceutical to the Fc region of an antibody to optimize the pharmacokinetic and pharmacodynamic properties of the biopharmaceutical as compared to traditional Fc-fusion conjugates.

Other Modifications:

The present disclosure contemplates the use of other modifications, currently known or developed in the future, of IL-10 to improve one or more properties. Examples include hesylation, various aspects of which are described in, for example, U.S. Patent Appln. Nos. 2007/0134197 and 2006/0258607, and fusion molecules comprising SUMO as a fusion tag (LifeSensors, Inc.; Malvern, Pa.).

Linkers:

Linkers and their use have been described above. Any of the foregoing components and molecules used to modify the polypeptide sequences of the present disclosure may optionally be conjugated via a linker. Suitable linkers include "flexible linkers" which are generally of sufficient length to permit some movement between the modified polypeptide sequences and the linked components and molecules. The linker molecules are generally about 6-50 atoms long. The linker molecules may also be, for example, aryl acetylene, ethylene glycol oligomers containing 2-10 monomer units, diamines, diacids, amino acids, or combinations thereof. Suitable linkers can be readily selected and can be of any suitable length, such as 1 amino acid (e.g., Gly), 2, 3, 4, 5, 6, 7, 8, 9, 10, 10-20, 20-30, 30-50 or more than 50 amino acids.

Examples of flexible linkers include glycine polymers $(G)_n$, glycine-serine polymers (for example, $(GS)_n$, $GSGGS_n$ (SEQ ID NO:13), $GGGS_n$ (SEQ ID NO:14), $(G_mS_o)_n$, $(G_m$-$S_oG_m)_n$, $(G_mS_oG_mS_oG_m)_n$ (SEQ ID NO:15), $(GSGGS_m)_n$ (SEQ ID NO:16), $(GSGS_mG)_n$ (SEQ ID NO:17) and $(GGGS_m)_n$ (SEQ ID NO:18), and combinations thereof, where m, and and o are each independently selected from an integer of at least one), glycine-alanine polymers, alanine-serine polymers, and other flexible linkers. Glycine and glycine-serine polymers are relatively unstructured, and therefore may serve as a neutral tether between components. Exemplary flexible linkers include, but are not limited to GGSG (SEQ ID NO:19), GGSGG (SEQ ID NO:20), GSGSG (SEQ ID NO:21), GSGGG (SEQ ID NO:22), GGGSG (SEQ ID NO:23), and GSSSG (SEQ ID NO:24).

Therapeutic and Prophylactic Uses

The present disclosure contemplates the use of the IL-10 polypeptides described herein (e.g., PEG-IL-10) in the treatment and/or prevention of diseases, disorders or conditions, and/or the symptoms thereof, relating to, or resulting from, for example, hypercholesterolemia, aberrant lipid profile, and other disorders associated, directly or indirectly, with cholesterol homeostasis. Indeed, the teachings of the present disclosure are meant to apply to any such disease, disorder or condition for which achieving or maintaining the above-described IL-10 mean serum trough concentration parameters may be beneficial. While particular uses are described in detail hereafter, it is to be understood that the present disclosure is not so limited. In addition, although specific categories of exemplary diseases, disorders and conditions associated with, or resulting from, hypercholesterolemia and aberrant lipid profile are discussed hereafter, it is to be understood that there is often overlap between one or more categories (e.g., certain cardiovascular diseases may have an inflammatory component).

Cardiovascular Diseases.

In particular embodiments, the present disclosure contemplates the use of the IL-10 polypeptides (e.g., PEG-IL-10) described herein to treat and/or prevent cardiovascular diseases, disorders and conditions, as well as disorders associated therewith, resulting from hypercholesterolemia and aberrant lipid profile.

As used herein, the terms "cardiovascular disease", "heart disease" and the like refer to any disease that affects the cardiovascular system, primarily cardiac disease, vascular diseases of the brain and kidney, and peripheral arterial diseases. Cardiovascular disease is a constellation of diseases, some of which are discussed further hereafter, that includes coronary heart disease (e.g., ischemic heart disease or coronary artery disease), atherosclerosis, cardiomyopathy, hypertension, hypertensive heart disease, cor pulmonale, cardiac dysrhythmias, endocarditis, cerebrovascular disease, and peripheral arterial disease. Cardiovascular disease is the leading cause of deaths worldwide, and while it usually affects older adults, the antecedents of cardiovascular disease, notably atherosclerosis, begin in early life.

In certain embodiments, the present disclosure contemplates the treatment and/or prevention of a peripheral vascular disease (PVD), also known as peripheral arterial disease (PAD) or peripheral arterial occlusive disease (PAOD). PVDs refer broadly to conditions characterized by an obstruction of large arteries, not within the coronary or cerebral vasculature, which results in either acute or chronic ischemia. PVDs also include a subset of diseases classified as microvascular diseases resulting from episodic narrowing of the arteries (e.g., Raynaud's phenomenon) or widening of the arteries (e.g., a vascular spasm). Symptoms of PVDs include, without limitation, pain, weakness, numbness, or cramping in muscles due to decreased blood flow, sores, wounds, or ulcers that heal slowly or not at all, and limb coolness or discoloration. About 20% of patients with mild PAD may be asymptomatic.

In particular embodiments, the IL-10 agents (e.g., PEG-IL-10) of the present disclosure are used in the treatment and/or prevention of a cardiovascular disease that comprises a cardiomyopathy, a condition characterized by the deterioration of myocardium function. Signs and symptoms may mimic those of almost any form of heart disease and include chest pain and EKG abnormalities. A mild cardiomyopathy is frequently asymptomatic, whereas a severe case is associated with heart failure, arrhythmias, systemic embolization or sudden cardiac death.

Several schemes may be used to classify a cardiomyopathy. One scheme classifies a cardiomyopathy functionally, as involving dilation, hypertrophy, or restriction. Another scheme classifies a cardiomyopathy as either extrinsic or intrinsic. An extrinsic cardiomyopathy refers to a cardiomyopathy where the primary pathology is outside the myocardium itself. For example, an extrinsic cardiomyopathy may be caused by a metabolic/storage disorder, an endocrine disorder, a neuromuscular disorder, a nutritional disorder, an inflammatory disorder, a toxicity (including drug and alcohol), an ischemia, and/or an infection (e.g., Hepatitis C). Non-limiting examples of extrinsic cardiomyopathies include acromegaly, alcoholic cardiomyopathy, amyloidosis, Chagas disease, diabetic cardiomyopathy, hemochromatosis, hypertensive cardiomyopathy, hyperthyroidism, inflammatory cardiomyopathy, ischemic cardiomyopathy, muscular dystrophy, valvular cardiomyopathy, a cardiomyopathy secondary to a systemic metabolic disease, a cardiomyopathy secondary to a systemic nutritional disease, a coronary artery disease, and a congenital heart disease. In contrast, an intrinsic cardiomyopathy refers to a cardiomyopathy characterized by weakness in the heart muscle that is of unknown origin. Non-limiting examples of intrinsic cardiomyopathies include dilated cardiomyopathy, hypertrophic cardiomyopathy, arrhythmogenic right ventricular cardiomyopathy, restrictive cardiomyopathy, isolated ventricular non-compaction, mitochondrial myopathy, Takotsubo cardiomyopathy, and Loeffler endocarditis.

Embodiments contemplated by the present disclosure include those wherein the disclosed IL-10 agents (e.g., PEG-IL-10) are used in the treatment and/or prevention of: i) an ischemic heart disease. Ischemic heart disease, or myocardial ischemia, refers to a condition characterized by reduced blood supply of the heart muscle, usually due to a narrowing or blockage of a coronary artery. Symptoms of ischemic heart disease include chest pain on exertion, in cold weather, or emotional situations; acute chest pain; acute coronary syndrome; unstable angina; myocardial infarction; heart failure, difficulty in breathing; or swelling of the extremities; ii) a congestive heart failure, conditions characterized by a heart abnormality that impairs the ability of the heart to fill with or pump a sufficient amount of blood throughout the body; and iii) a hypertensive heart disease, conditions characterized by high blood pressure that include, without limitation, left ventricular hypertrophy, coronary heart disease, congestive heart failure, hypertensive cardiomyopathy, and cardiac arrhythmias.

Particular embodiments of the present disclosure are directed to the use of the IL-10 polypeptides described herein to treat and/or prevent atherosclerosis, a chronic condition in which an arterial wall thickens to form plaques as a result of the accumulation of fatty materials such as cholesterol and triglycerides. As discussed further herein, atherosclerosis frequently involves a chronic inflammatory response in the walls of arteries, caused largely by the accumulation of macrophages and promoted by LDLs without adequate removal of fats and cholesterol from the macrophages by functional HDLs. Chronically expanding atherosclerotic lesions can cause complete closure of the lumen, which may only manifest when the lumen stenosis is so severe that blood supply to downstream tissue(s) is insufficient, resulting in ischemia.

Particularly contemplated by the present disclosure are embodiments wherein the cardiovascular disease comprises a hyperlipidemia (or hyperlipoproteinemia), conditions characterized by abnormally elevated levels of lipids and/or lipoproteins in the blood. Hyperlipidemias may be classified as familial (or primary) when caused by specific genetic abnormalities, acquired (or secondary) when resulting from another underlying disorder, or idiopathic, when of unknown cause. Hyperlipidemias may also be classified based on which types of lipids and/or lipoproteins are elevated. Non-limiting examples of hyperlipidemias include dyslipidemia, hypercholesterolemia, hyperglyceridemia, hypertriglyceridemia, hyperlipoproteinemia, hyperchylomicronemia, and combined hyperlipidemia. Hyperlipoproteinemias include, for example, hyperlipoproteinemia type Ia, hyperlipoproteinemia type Ib, hyperlipoproteinemia type Ic, hyperlipoproteinemia type IIa, hyperlipoproteinemia type IIb, hyperlipoproteinemia type III, hyperlipoproteinemia type IV, and hyperlipoproteinemia type V.

Attempts to treat cardiovascular disease by controlling levels of lipids and/or lipoproteins in the blood have met with limited success. For example, although administration of statins reduces cardiovascular risk in some individuals, these therapeutic compounds do not reduce triglyceride levels. In individuals at cardiovascular risk who exhibit deleteriously high levels of triglycerides, a member of the fibrate class of therapeutic agents may be administered. However, although lowering triglyceride and LDL levels, fibrates do not affect HDL levels. Moreover, combination treatments involving statins and fibrates, while sometimes effective, often cause a significant increase in the risk of myopathy and rhabdomyolysis, and therefore can only be carried out under very close medical supervision. In view of limitations as exemplified above, there is clearly a need for improved agents for the use and treatment of cardiovascular diseases, including those associated with high lipid and/or lipoprotein levels.

Thrombosis and Thrombotic Conditions.

In other embodiments, the present disclosure contemplates the use of the IL-10 polypeptides (e.g., PEG-IL-10) described herein to treat and/or prevent thrombosis and thrombotic diseases, disorders and conditions, as well as disorders associated therewith, resulting from hypercholesterolemia and aberrant lipid profile. Thrombosis, the formation of a thrombus inside a blood vessel resulting in obstruction of the flow of blood through the circulatory system, may be caused by abnormalities in one or more of the following (Virchow's triad): hypercoagulability or increased blood clotting, endothelial cell injury, or disturbed blood flow (stasis, turbulence).

Thrombosis is generally categorized as venous or arterial, each of which can be presented by several subtypes. Venous thrombosis includes deep vein thrombosis (DVT), portal vein thrombosis, renal vein thrombosis, jugular vein thrombosis, Budd-Chiari syndrome, Paget-Schroetter disease, and cerebral venous sinus thrombosis. Arterial thrombosis includes stroke and myocardial infarction.

Inflammatory Disorders.

When cholesterol and/or LDL become embedded in the walls of blood vessels, an immune response can be triggered, which, in turn, results in chronic inflammation. In response to this inflammation, blood monocytes adhere to the endothelium, transmigrate into the subendothelial space, and differentiate toward macrophages. Macrophages, in turn, engulf the cholesterol deposits and modified LDL by phagocytosis via scavenger receptors, which are distinct from LDL receptors. However, the adaptive mechanisms mediated by macrophages are not sufficient to process the uncontrolled cholesterol and/or LDL deposition seen under pathologic conditions. As a result, the lipid-laden macrophages transform into "foam cells", often accompanied by release of inflammation-inducing molecules. Both cholesterol/LDL deposition and the attendant foam cell-mediated pro-inflammatory reactions in the walls of the blood vessels lead to the development of atherosclerotic lesions. Thus, one consequence of modulating the levels of a lipid or lipoprotein is the reduction or elimination of a chronic inflammation.

The present disclosure includes embodiments wherein the IL-10 agents described herein (e.g., PEG-IL-10) are used in the treatment and/or prevention of a vasculitis. Vasculitis is a varied group of disorders featuring inflammation of a vessel wall including lymphatic vessels and blood vessels like veins (phlebitis), arteries (arteritis) and capillaries due to leukocyte migration and resultant damage. The inflammation may affect arteries and/or veins, regardless of size. It may be focal or widespread, with areas of inflammation scattered throughout a particular organ or tissue, or even affecting more than one organ system in the body. Vasculitis includes, without limitation, Buerger's disease (thromboangiitis obliterans), cerebral vasculitis (central nervous system vasculitis), Churg-Strauss arteritis, cryoglobulinemia, essential cryoglobulinemic vasculitis, giant cell (temporal) arteritis, Henoch-Schonlein purpura, hypersensitivity vasculitis (allergic vasculitis), Kawasaki disease, microscopic polyarteritis/polyangiitis, polyarteritis nodosa, polymyalgia rheumatica (PMR), rheumatoid vasculitis, Takayasu arteritis, thrombophlebitis, Wegener's granulomatosis; and vasculitis secondary to connective tissue disorders like systemic lupus erythematosus, rheumatoid arthritis, relapsing polychondritis, Behcet's disease, or other connective tissue disorders; and vasculitis secondary to viral infection.

Other embodiments are directed to an inflammatory heart disease, which refers to a condition characterized by inflammation of the heart muscle and/or the surrounding tissue. Examples include, but are not limited to, endocarditis, inflammatory cardiomegaly, and myocarditis.

Pharmaceutical Compositions

The IL-10 polypeptides of the present disclosure may be in the form of compositions suitable for administration to a subject. In general, such compositions are "pharmaceutical compositions" comprising IL-10 and one or more pharmaceutically acceptable or physiologically acceptable diluents, carriers or excipients. In certain embodiments, the IL-10 polypeptides are present in a therapeutically acceptable amount. The pharmaceutical compositions may be used in the methods of the present disclosure; thus, for example, the pharmaceutical compositions can be administered ex vivo or in vivo to a subject in order to practice the therapeutic and prophylactic methods and uses described herein.

The pharmaceutical compositions of the present disclosure can be formulated to be compatible with the intended method or route of administration; exemplary routes of administration are set forth herein. Furthermore, the pharmaceutical compositions may be used in combination with other therapeutically active agents or compounds as described herein in order to treat or prevent the diseases, disorders and conditions as contemplated by the present disclosure.

The pharmaceutical compositions typically comprise a therapeutically effective amount of an IL-10 polypeptide contemplated by the present disclosure and one or more pharmaceutically and physiologically acceptable formulation agents. Suitable pharmaceutically acceptable or physiologically acceptable diluents, carriers or excipients include, but are not limited to, antioxidants (e.g., ascorbic acid and sodium bisulfate), preservatives (e.g., benzyl alcohol, methyl parabens, ethyl or n-propyl, p-hydroxybenzoate), emulsifying agents, suspending agents, dispersing agents, solvents, fillers, bulking agents, detergents, buffers, vehicles, diluents, and/or adjuvants. For example, a suitable vehicle may be physiological saline solution or citrate buffered saline, possibly supplemented with other materials common in pharmaceutical compositions for parenteral administration. Neutral buffered saline or saline mixed with serum albumin are further exemplary vehicles. Those skilled in the art will readily recognize a variety of buffers that can be used in the pharmaceutical compositions and dosage forms contemplated herein. Typical buffers include, but are not limited to, pharmaceutically acceptable weak acids, weak bases, or mixtures thereof. As an example, the buffer components can be water soluble materials such as phosphoric acid, tartaric acids, lactic acid, succinic acid, citric acid, acetic acid, ascorbic acid, aspartic acid, glutamic acid, and salts thereof. Acceptable buffering agents include, for example, a Tris buffer, N-(2-Hydroxyethyl)piperazine-N'-(2-ethanesulfonic acid) (HEPES), 2-(N-Morpholino)ethanesulfonic acid (MES), 2-(N-Morpholino)ethanesulfonic acid sodium salt (MES), 3-(N-Morpholino)propanesulfonic acid (MOPS), and N-tris[Hydroxymethyl]methyl-3-aminopropanesulfonic acid (TAPS).

After a pharmaceutical composition has been formulated, it may be stored in sterile vials as a solution, suspension, gel, emulsion, solid, or dehydrated or lyophilized powder. Such formulations may be stored either in a ready-to-use form, a lyophilized form requiring reconstitution prior to use, a liquid form requiring dilution prior to use, or other acceptable form. In some embodiments, the pharmaceutical composition is provided in a single-use container (e.g., a single-use vial, ampoule, syringe, or autoinjector (similar to, e.g., an EpiPen®)), whereas a multi-use container (e.g., a multi-use vial) is provided in other embodiments. Any drug delivery apparatus may be used to deliver IL-10, including implants (e.g., implantable pumps) and catheter systems, slow injection pumps and devices, all of which are well known to the skilled artisan. Depot injections, which are generally administered subcutaneously or intramuscularly, may also be utilized to release the polypeptides disclosed herein over a defined period of time. Depot injections are usually either solid- or oil-based and generally comprise at least one of the formulation components set forth herein. One of ordinary skill in the art is familiar with possible formulations and uses of depot injections.

The pharmaceutical compositions may be in the form of a sterile injectable aqueous or oleagenous suspension. This suspension may be formulated according to the known art using those suitable dispersing or wetting agents and suspending agents mentioned herein. The sterile injectable preparation may also be a sterile injectable solution or suspension in a non-toxic parenterally-acceptable diluent or solvent, for example, as a solution in 1,3-butane diol. Acceptable diluents, solvents and dispersion media that may be employed include water, Ringer's solution, isotonic sodium chloride solution, Cremophor EL™ (BASF, Parsippany, N.J.) or phosphate buffered saline (PBS), ethanol, polyol (e.g., glycerol, propylene glycol, and liquid polyethylene glycol), and suitable mixtures thereof. In addition, sterile, fixed oils are conventionally employed as a solvent or suspending medium. For this purpose any bland fixed oil may be employed, including synthetic mono- or diglycerides. Moreover, fatty acids such as oleic acid, find use in the preparation of injectables. Prolonged absorption of particular injectable formulations can be achieved by including an agent that delays absorption (e.g., aluminum monostearate or gelatin).

The pharmaceutical compositions containing the active ingredient may be in a form suitable for oral use, for example, as tablets, capsules, troches, lozenges, aqueous or oily suspensions, dispersible powders or granules, emulsions, hard or soft capsules, or syrups, solutions, microbeads or elixirs. In particular embodiments, an active ingredient of an agent co-administered with an IL-10 agent described herein is in a form suitable for oral use. Pharmaceutical compositions intended for oral use may be prepared according to any method known to the art for the manufacture of pharmaceutical compositions, and such compositions may contain one or more agents such as, for example, sweetening agents, flavoring agents, coloring agents and preserving agents in order to provide pharmaceutically elegant and palatable preparations. Tablets, capsules and the like contain the active ingredient in admixture with non-toxic pharmaceutically acceptable excipients which are suitable for the manufacture of tablets. These excipients may be, for example, diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc.

The tablets, capsules and the like suitable for oral administration may be uncoated or coated by known techniques to delay disintegration and absorption in the gastrointestinal tract and thereby provide a sustained action. For example, a time-delay material such as glyceryl monostearate or glyceryl distearate may be employed. They may also be coated by techniques known in the art to form osmotic therapeutic tablets for controlled release. Additional agents include biodegradable or biocompatible particles or a polymeric substance such as polyesters, polyamine acids, hydrogel, polyvinyl pyrrolidone, polyanhydrides, polyglycolic acid, ethylenevinylacetate, methylcellulose, carboxymethylcellulose, protamine sulfate, or lactide/glycolide copolymers, polylactide/glycolide copolymers, or ethylenevinylacetate copolymers in order to control delivery of an administered composition. For example, the oral agent can be entrapped in microcapsules prepared by coacervation techniques or by interfacial polymerization, by the use of hydroxymethylcellulose or gelatin-microcapsules or poly (methylmethacrolate) microcapsules, respectively, or in a colloid drug delivery system. Colloidal dispersion systems include macromolecule complexes, nano-capsules, microspheres, microbeads, and lipid-based systems, including oil-in-water emulsions, micelles, mixed micelles, and liposomes. Methods for the preparation of the above-mentioned formulations will be apparent to those skilled in the art.

Formulations for oral use may also be provided as hard gelatin capsules wherein the active ingredient is mixed with an inert solid diluent, for example, calcium carbonate, calcium phosphate, kaolin or microcrystalline cellulose, or as soft gelatin capsules wherein the active ingredient is mixed with water or an oil medium, for example peanut oil, liquid paraffin, or olive oil.

Aqueous suspensions contain the active materials in admixture with excipients suitable for the manufacture thereof. Such excipients can be suspending agents, for example sodium carboxymethylcellulose, methylcellulose, hydroxy-propylmethylcellulose, sodium alginate, polyvinylpyrrolidone, gum tragacanth and gum acacia; dispersing or wetting agents, for example a naturally-occurring phosphatide (e.g., lecithin), or condensation products of an alkylene oxide with fatty acids (e.g., polyoxy-ethylene stearate), or condensation products of ethylene oxide with long chain aliphatic alcohols (e.g., for heptadecaethyleneoxycetanol), or condensation products of ethylene oxide with partial esters derived from fatty acids and a hexitol (e.g., polyoxyethylene sorbitol monooleate), or condensation products of ethylene oxide with partial esters derived from fatty acids and hexitol anhydrides (e.g., polyethylene sorbitan monooleate). The aqueous suspensions may also contain one or more preservatives.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified herein.

The pharmaceutical compositions of the present disclosure may also be in the form of oil-in-water emulsions. The oily phase may be a vegetable oil, for example olive oil or *arachis* oil, or a mineral oil, for example, liquid paraffin, or mixtures of these. Suitable emulsifying agents may be naturally occurring gums, for example, gum acacia or gum tragacanth; naturally occurring phosphatides, for example, soy bean, lecithin, and esters or partial esters derived from fatty acids; hexitol anhydrides, for example, sorbitan monooleate; and condensation products of partial esters with ethylene oxide, for example, polyoxyethylene sorbitan monooleate.

Formulations can also include carriers to protect the composition against rapid degradation or elimination from the body, such as a controlled release formulation, including implants, liposomes, hydrogels, prodrugs and microencapsulated delivery systems. For example, a time delay material such as glyceryl monostearate or glyceryl stearate alone, or in combination with a wax, may be employed.

The present disclosure contemplates the administration of the IL-10 polypeptides in the form of suppositories for rectal administration. The suppositories can be prepared by mixing the drug with a suitable non-irritating excipient which is solid at ordinary temperatures but liquid at the rectal temperature and will therefore melt in the rectum to release the drug. Such materials include, but are not limited to, cocoa butter and polyethylene glycols.

The IL-10 polypeptides contemplated by the present disclosure may be in the form of any other suitable pharmaceutical composition (e.g., sprays for nasal or inhalation use) currently known or developed in the future.

The concentration of a polypeptide or fragment thereof in a formulation can vary widely (e.g., from less than about 0.1%, usually at or at least about 2% to as much as 20% to 50% or more by weight) and will usually be selected primarily based on fluid volumes, viscosities, and subject-based factors in accordance with, for example, the particular mode of administration selected.

Routes of Administration

The present disclosure contemplates the administration of IL-10, and compositions thereof, in any appropriate manner. Suitable routes of administration include parenteral (e.g., intramuscular, intravenous, subcutaneous (e.g., injection or implant), intraperitoneal, intracisternal, intraarticular, intraperitoneal, intracerebral (intraparenchymal) and intracerebroventricular), oral, nasal, vaginal, sublingual, intraocular, rectal, topical (e.g., transdermal), sublingual and inhalation. Depot injections, which are generally administered subcutaneously or intramuscularly, may also be utilized to release the IL-10 polypeptides disclosed herein over a defined period of time.

Particular embodiments of the present disclosure contemplate parenteral administration, and in further particular embodiments the parenteral administration is subcutaneous.

Combination Therapy

The present disclosure contemplates the use of IL-10 (e.g., PEG-IL-10) in combination with one or more active therapeutic agents or other prophylactic or therapeutic modalities (e.g., radiation). In such combination therapy, the various active agents frequently have different mechanisms of action than IL-10. Such combination therapy may be especially advantageous by allowing a dose reduction of one or more of the agents, thereby reducing or eliminating the adverse effects associated with one or more of the agents; furthermore, such combination therapy may have a synergistic therapeutic or prophylactic effect on the underlying disease, disorder, or condition.

In particular embodiments, the present disclosure provides methods for treating and/or preventing diseases, disorders or conditions associated with (either directly or indirectly) cholesterol homeostasis, including associated cardiovascular, thrombotic and inflammatory disorders, with the IL-10 polypeptides described herein (e.g., PEG-IL-10) and at least one additional therapeutic or diagnostic agent. It is to be understood that combination therapy is not limited to agents that treat and/or prevent the aforementioned diseases, disorders and conditions; for example, agents contemplated for use in combination with the IL-10 polypeptides may have efficacy in treating or preventing other metabolic disorders, such as diabetes or obesity. Use of the IL-10 polypeptides (e.g., PEG-IL-10) in combination with modified diets and/or exercise regimens is also contemplated herein.

As used herein, "combination" is meant to include therapies that can be administered separately, for example, formulated separately for separate administration (e.g., as may be provided in a kit), and therapies that can be administered together in a single formulation (i.e., a "co-formulation").

In certain embodiments, the IL-10 polypeptides are administered or applied sequentially, e.g., where one agent is administered prior to one or more other agents. In other embodiments, the IL-10 polypeptides are administered simultaneously, e.g., where two or more agents are administered at or about the same time; the two or more agents may be present in two or more separate formulations or combined into a single formulation (i.e., a co-formulation). Regardless of whether the two or more agents are administered sequentially or simultaneously, they are considered to be administered in combination for purposes of the present disclosure.

The IL-10 polypeptides of the present disclosure may be used in combination with at least one active agent in any manner appropriate under the circumstances. In one embodiment, treatment with the at least one active agent and at least one IL-10 polypeptide of the present disclosure is maintained over a period of time. In another embodiment, treatment with the at least one active agent is reduced or discontinued (e.g., when the subject is stable), while treatment with the IL-10 polypeptide of the present disclosure is maintained at a constant dosing regimen. In a further embodiment, treatment with the at least one active agent is reduced or discontinued (e.g., when the subject is stable), while treatment with the IL-10 polypeptide of the present disclosure is reduced (e.g., lower dose, less frequent dosing or shorter treatment regimen). In yet another embodiment, treatment with the at least one active agent is reduced or discontinued (e.g., when the subject is stable), and treatment with the IL-10 polypeptide of the present disclosure is increased (e.g., higher dose, more frequent dosing or longer treatment regimen). In yet another embodiment, treatment with the at least one active agent is maintained and treatment with the IL-10 polypeptide of the present disclosure is discontinued or reduced (e.g., lower dose, less frequent dosing or shorter treatment regimen). In yet another embodiment, treatment with the at least one active agent and treatment with the IL-10 polypeptide of the present disclosure are discontinued or reduced (e.g., lower dose, less frequent dosing or shorter treatment regimen).

While particular agents suitable for use in combination with the IL-10 polypeptides (e.g., PEG-IL-10) disclosed herein are set forth hereafter, it is to be understood that the present disclosure is not so limited. Hereafter, certain agents are set forth in specific categories of exemplary diseases, disorders and conditions; however, it is to be understood that there is often overlap between one or more categories (e.g., certain agents may have both cardiovascular and anti-inflammatory effects).

Cholesterol Homeostasis Agents.

Particular embodiments of the present disclosure involve combinations of IL-10 polypeptides with agents associated with cholesterol homeostasis. Many of these agents target different pathways involving the absorption, synthesis, transport, storage, catabolism, and excretion of cholesterol, and are thus particularly useful candidates for combination therapy.

Examples of therapeutic agents useful in combination therapy for the treatment of hypercholesterolemia (and thus frequently atherosclerosis, for example) include statins (e.g., CRESTOR, LESCOL, LIPITOR, MEVACOR, PRAVACOL, and ZOCOR), which inhibit the enzymatic synthesis of cholesterol; bile acid resins (e.g., COLESTID, LO-CHOLEST, PREVALITE, QUESTRAN, and WELCHOL), which sequester cholesterol and prevent its absorption; ezetimibe (ZETIA), which blocks cholesterol absorption; fibric acid (e.g., TRICOR), which reduce triglycerides and may modestly increase HDL; niacin (e.g., NIACOR), which modestly lowers LDL cholesterol and triglycerides; and/or a combination of the aforementioned (e.g., VYTORIN (ezetimibe with simvastatin). Alternative cholesterol treatments that may be candidates for use in combination with the IL-10 polypeptides described herein include various supplements and herbs (e.g., garlic, policosanol, and guggul). Several classes of the aforementioned therapeutic agents are discussed further hereafter.

Particular embodiments of the present disclosure comprise an IL-10 agent in combination with a fibrate. Fibrates, a class of amphipathic carboxylic acids, may be used as anti-hyperlipidemic agents to decrease levels of, e.g., triglycerides and LDL, and to increase levels of HDL. Examples of suitable fibrates include, without limitation, Bezafibrate, Ciprofibrate, Clofibrate, Gemfibrozil, and Fenofibrate.

Further particular embodiments of the present disclosure comprise an IL-10 agent in combination with a HMG-CoA Reductase Inhibitor (a statin). HMG-CoA Reductase Inhibitors may lower LDL and/or cholesterol levels by inhibiting the enzyme HMG-CoA Reductase, which plays a central role in the production of cholesterol in the liver. To compensate for the decreased cholesterol availability, synthesis of hepatic LDL receptors is increased, resulting in increased clearance of LDL particles from the blood. Examples of suitable statins include, without limitation, Atorvastatin, Fluvastatin, Lovastatin, Pitavastatin, Pravastatin, Rosuvastatin, and Simvastatin. Combinations of IL-10 polypeptides with a statin are particularly contemplated herein.

Still further particular embodiments of the present disclosure comprise an IL-10 agent in combination with a niacin. Niacins may lower LDL levels by selectively inhibiting hepatic diacyglycerol acyltransferase-2; reducing triglyceride synthesis, and reducing VLDL secretion through a receptor HM74 and HM74A or GPR109A. A non-limiting use of a niacin is as an anti-hyperlipidemic agent to inhibit the breakdown of fats in adipose tissue. By blocking the breakdown of fats, a niacin causes a decrease in free fatty acids in the blood and, as a consequence, decreases the secretion of VLDL and cholesterol by the liver. By lowering VLDL levels, a niacin may also increase the level of HDL in blood. Examples of suitable niacins include, without limitation, acipimox, niacin, nicotinamide, and vitamin B3.

Other particular embodiments of the present disclosure comprise an IL-10 agent in combination with a bile acid sequestrant. Bile acid sequestrants (also known as resins) bind certain components of bile in the gastrointestinal tract, thereby disrupting the enterohepatic circulation of bile acids by sequestering them and preventing their reabsorption from the gut. Bile acid sequestrants are particularly effective for lowering LDL and cholesterol, and may also raise HDL levels. Examples of suitable bile acid sequestrants include, without limitation, Cholestyramine, Colesevelam, and Colestipol.

Additional particular embodiments of the present disclosure comprise an IL-10 agent in combination with a cholesterol absorption inhibitor. Cholesterol absorption inhibitors decrease absorption of cholesterol from the intestine; this leads to up-regulation of LDL-receptors on the surface of cells and increased LDL cholesterol uptake into these cells, thus decreasing levels of LDL in the blood plasma. Examples of suitable cholesterol absorption inhibitors include, without limitation, ezetimibe, a phytosterol, a sterol and a stanol. Combinations of IL-10 polypeptides with ezetimibe are particularly contemplated herein. Ezetimibe selectively blocks cholesterol absorption and lowers plasma LDL levels by an average of 18%. When ezetimibe is co-administered with lower doses of statins, there is an additive reduction in LDL levels, which equals the reduction achieved with maximal doses of statins alone. Reduction in the statin dose results in fewer statin-related adverse effects.

Still further particular embodiments of the present disclosure comprise an IL-10 agent in combination with a fat absorption inhibitor. Fat absorption inhibitors decrease the absorption of fat from the intestine, thereby reducing caloric intake. In one aspect, a fat absorption inhibitor inhibits pancreatic lipase, an enzyme that breaks down triglycerides in the intestine. Examples of suitable fat absorption inhibitors include, without limitation, Orlistat.

In still other particular embodiments, the present disclosure contemplates use of the PEG-IL-10 agents described herein in combination with modulators of PCSK9 (Proprotein convertase subtilisin/kexin type 9). PCSK9 plays a major regulatory role in cholesterol homeostasis. It is a serine protease expressed predominantly in the liver, intestine and kidney. The encoded protein is synthesized as a soluble zymogen that undergoes autocatalytic intramolecular processing in the endoplasmic reticulum.

As part of the cholesterol homeostasis process, LDL cholesterol is removed from the blood when it binds to LDL receptors (LDLR) on the surface of liver cells and is taken up by such cells. PCSK9 functions by binding to LDLR and inducing receptor degradation, thereby preventing LDLR recycling to the cell surface to remove more LDL cholesterol, ultimately resulting in decreased metabolism thereof. Preventing PCSK9 binding to LDLR allows the receptor to return to the cell surface and remove more cholesterol. As discussed further herein, PEG-IL-10 down-regulates message expression of PCSK9 in knock-out mice lacking the LDL receptor. Thus, PEG-IL-10 dramatically lowers cholesterol in a non-PCSK9-dependent manner, indicating that combination of PEG-IL-10 with a PCSK9 inhibitor would have additive effects.

Inhibitors of PCSK9 function have been shown to cause much more cholesterol lowering than traditional commercially available agents, with an acceptable adverse effect profile. The present disclosure contemplates the use of PEG-IL-10 with any modulator having a direct or indirect inhibitory effect on PCSK9. Several monoclonal antibodies that bind to PCSK9 and interfere with its interaction with the LDLR are being developed (e.g., by Amgen (AMG145), Merck (1D05-IgG2) and Aventis/Regeneron (SAR236553/REGN727)). In addition, peptides that mimic the EGFA domain of the LDLR that binds to PCSK9 are being developed, and gene silencing through the administration of a PCSK9 antisense oligonucleotide (ISIS Pharmaceuticals) has been shown to increase expression of the LDLR and decrease circulating total cholesterol levels in mice. Other modulators of PCSK9 function contemplated for combination therapy with the PEG-IL-10 agents described herein are those which act by means of RNA interference (RNAi) (Alnylam Pharmaceuticals) and as a locked nucleic acid (LNA) (Santaris Pharma), also referred to as inaccessible RNA.

The present disclosure encompasses pharmaceutically acceptable salts, acids or derivatives of any of the above.

Immune and Inflammatory Conditions.

The present disclosure provides methods for treating and/or preventing immune- and/or inflammatory-related diseases, disorders and conditions, as well as disorders associated therewith, with an IL-10 polypeptide (e.g., PEG-IL-10) and at least one additional agent having immune- and/or inflammatory-related properties. By way of example, an IL-10 polypeptide may be administered with an agent having efficacy in a cardiovascular disorder having an inflammatory component.

Examples of therapeutic agents useful in combination therapy include, but are not limited to, non-steroidal anti-inflammatory drugs (NSAIDs). NSAIDs, a large group of therapeutic compounds with analgesic, anti-inflammatory, and anti-pyretic properties, reduce inflammation by blocking cyclooxygenase. Examples of such agents include ibuprofen, and other propionic acid derivatives (alminoprofen, benoxaprofen, bucloxic acid, carprofen, fenbufen, fenoprofen, fluprofen, flurbiprofen, indoprofen, ketoprofen, miroprofen, naproxen, oxaprozin, pirprofen, pranoprofen, suprofen, tiaprofenic acid, and tioxaprofen); acetic acid derivatives (indomethacin, acemetacin, alclofenac, clidanac, diclofenac, fenclofenac, fenclozic acid, fentiazac, fuirofenac, ibufenac, isoxepac, oxpinac, sulindac, tiopinac, tolmetin, zidometacin, and zomepirac); fenamic acid derivatives (flufenamic acid, meclofenamic acid, mefenamic acid, niflumic acid and tolfenamic acid); biphenylcarboxylic acid derivatives (diflunisal and flufenisal); oxicams (isoxicam, piroxicam, sudoxicam and tenoxican); salicylates (acetyl salicylic acid, sulfasalazine); and the pyrazolones (apazone, bezpiperylon, feprazone, mofebutazone, oxyphenbutazone, phenylbutazone).

Other combinations include selective cyclooxygenase-2 (COX-2) inhibitors, selective cyclooxygenase 1 (COX 1) inhibitors, and non-selective cyclooxygenase (COX) inhibitors. Particular embodiments of the present disclosure contemplate the IL-10 polypeptides described herein (e.g., PEG-IL-10) in combination with a suitable selective COX-2 inhibitor(s), such as Celecoxib, Etoricoxib, Firocoxib, Lumiracoxib, Meloxicam, Parecoxib, Rofecoxib, and Valdecoxib.

Other active agents for combination include steroids such as prednisolone, prednisone, methylprednisolone, betamethasone, dexamethasone, or hydrocortisone. Such a combination may be especially advantageous, since one or more side-effects of the steroid can be reduced or even eliminated by decreasing the steroid dose required when treating patients in combination with the present IL-10 polypeptides.

Additional examples of active agents for combinations for treating, for example, rheumatoid arthritis include cytokine suppressive anti-inflammatory drug(s) (CSAIDs); antibodies to or antagonists of other human cytokines or growth factors, for example, TNF, LT, IL-1β, IL-2, IL-6, IL-7, IL-8, IL-15, IL-16, IL-18, EMAP-II, GM-CSF, FGF, or PDGF.

Particular combinations of active agents may interfere at different points in the autoimmune and subsequent inflammatory cascade, and include TNF antagonists like chimeric, humanized or human TNF antibodies, REMICADE, anti-TNF antibody fragments (e.g., CDP870), and soluble p55 or p75 TNF receptors, derivatives thereof, p75TNFRIgG (ENBREL) or p55TNFR1gG (LENERCEPT), soluble IL-13 receptor (sIL-13), and also TNFα converting enzyme (TACE) inhibitors; similarly IL-1 inhibitors (e.g., Interleukin-1-converting enzyme inhibitors) may be effective. Other combinations include Interleukin 11, anti-P7s and p-selectin glycoprotein ligand (PSGL). Other examples of agents useful in combination with the IL-10 polypeptides described herein include interferon-β1a (AVONEX); interferon-β1b (BETASERON); copaxone; hyperbaric oxygen; intravenous immunoglobulin; clabribine; and antibodies to or antagonists of other human cytokines or growth factors (e.g., antibodies to CD40 ligand and CD80).

The present disclosure encompasses pharmaceutically acceptable salts, acids or derivatives of any of the above.

Anti-Diabetic and Anti-Obesity Agents.

Some patients requiring pharmacological treatment for a cholesterol-related disorder(s) are also taking anti-diabetic and/or anti-obesity agents. The present disclosure contemplates combination therapy with numerous anti-diabetic agents (and classes thereof), including 1) insulin, insulin mimetics and agents that entail stimulation of insulin secretion, including sulfonylureas (e.g., chlorpropamide, tolazamide, acetohexamide, tolbutamide, glyburide, glimepiride, glipizide) and meglitinides (e.g., repaglinide (PRANDIN) and nateglinide (STARLIX)); 2) biguanides (e.g., metformin (GLUCOPHAGE)) and other agents that act by promoting glucose utilization, reducing hepatic glucose production and/or diminishing intestinal glucose output; 3) alpha-glucosidase inhibitors (e.g., acarbose and miglitol) and other agents that slow down carbohydrate digestion and consequently absorption from the gut and reduce postprandial hyperglycemia; 4) thiazolidinediones (e.g., rosiglitazone (AVANDIA), troglitazone (REZULIN), pioglitazone (ACTOS), glipizide, balaglitazone, rivoglitazone, netoglitazone, troglitazone, englitazone, ciglitazone, adaglitazone, darglitazone that enhance insulin action (e.g., by insulin sensitization), thus promoting glucose utilization in peripheral tissues; 5) glucagon-like-peptides including DPP-IV inhibitors (e.g., vildagliptin (GALVUS) and sitagliptin (JANUVIA)) and Glucagon-Like Peptide-1 (GLP-1) and GLP-1 agonists and analogs (e.g., exenatide (BYETTA)); 6) and DPP-IV-resistant analogues (incretin mimetics), PPAR gamma agonists, dual-acting PPAR agonists, pan-acting PPAR agonists, PTP1B inhibitors, SGLT inhibitors, insulin secretagogues, glycogen synthase kinase-3 inhibitors, immune modulators, beta-3 adrenergic receptor agonists, 11beta-HSD1 inhibitors, and amylin analogues. In still other embodiments, the IL-10 agents described herein are used in combination with one or more suitable nuclear receptor binding agents (e.g., a Retinoic Acid Receptor (RAR) binding agent, a Retinoid X Receptor (RXR) binding agent, a Liver X Receptor (LXR) binding agent and a Vitamin D binding agent).

Furthermore, the present disclosure contemplates combination therapy with agents and methods for promoting weight loss, such as agents that stimulate metabolism or decrease appetite, and modified diets and/or exercise regimens to promote weight loss.

The present disclosure encompasses pharmaceutically acceptable salts, acids or derivatives of any of the above.

Dosing

The IL-10 polypeptides of the present disclosure may be administered to a subject in an amount that is dependent upon, for example, the goal of the administration (e.g., the degree of resolution desired); the age, weight, sex, and health and physical condition of the subject the formulation being administered; the route of administration; and the nature of the disease, disorder, condition or symptom thereof. The dosing regimen may also take into consideration the existence, nature, and extent of any adverse effects associated with the agent(s) being administered. Effective dosage amounts and dosage regimens can readily be determined from, for example, safety and dose-escalation trials, in vivo studies (e.g., animal models), and other methods known to the skilled artisan.

The present disclosure contemplates administration of IL-10 to achieve certain serum trough concentrations and/or maintain certain mean serum trough concentrations. Methodologies specific to IL-10 are described elsewhere herein and in this section below.

In general, dosing parameters dictate that the dosage amount be less than an amount that could be irreversibly toxic to the subject (i.e., the maximum tolerated dose, "MTD") and not less than an amount required to produce a measurable effect on the subject. Such amounts are determined by, for example, the pharmacokinetic and pharmacodynamic parameters associated with ADME, taking into consideration the route of administration and other factors.

An effective dose (ED) is the dose or amount of an agent that produces a therapeutic response or desired effect in some fraction of the subjects taking it. The "median effective dose" or ED50 of an agent is the dose or amount of an agent that produces a therapeutic response or desired effect in 50% of the population to which it is administered. Although the ED50 is commonly used as a measure of reasonable expectance of an agent's effect, it is not necessarily the dose that a clinician might deem appropriate taking into consideration all relevant factors. Thus, in some situations the effective amount is more than the calculated ED50, in other situations the effective amount is less than the calculated ED50, and in still other situations the effective amount is the same as the calculated ED50.

In addition, an effective dose of the IL-10 polypeptide of the present disclosure may be an amount that, when administered in one or more doses to a subject, produces a desired result relative to a healthy subject. For example, for a subject experiencing a particular disorder, an effective dose may be one that improves a diagnostic parameter, measure, marker and the like of that disorder by at least about 5%, at least about 10%, at least about 20%, at least about 25%, at least about 30%, at least about 40%, at least about 50%, at least about 60%, at least about 70%, at least about 80%, at least about 90%, or more than 90%, where 100% is defined as the diagnostic parameter, measure, marker and the like exhibited by a normal subject.

The amount of PEG-IL-10 necessary to treat a disease, disorder or condition described herein is based on the IL-10 activity of the conjugated protein, which can be determined by IL-10 activity assays known in the art. By way of example, in the tumor context, suitable IL-10 activity includes, for example, CD8+ T-cell infiltrate into tumor sites, expression of inflammatory cytokines, such as IFN-γ, IL-4, IL-6, IL-10, and RANK-L, from these infiltrating cells, and increased levels of TNF-α or IFN-γ in biological samples.

The therapeutically effective amount of PEG-IL-10 can range from about 0.01 to about 100 µg protein/kg of body weight/day, from about 0.1 to 20 µg protein/kg of body weight/day, from about 0.5 to 10 µg protein/kg of body weight/day, or about 1 to 4 µg protein/kg of body weight/day. In some embodiments, PEG-IL-10 is administered by continuous infusion to delivery about 50 to 800 µg protein/kg of body weight/day (e.g., about 1 to 16 µg protein/kg of body weight/day of PEG-IL-10). The infusion rate may be varied based on evaluation of, for example, adverse effects and blood cell counts.

For administration of an oral agent, the compositions can be provided in the form of tablets, capsules and the like containing from 1.0 to 1000 milligrams of the active ingredient, particularly 1.0, 3.0, 5.0, 10.0, 15.0, 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient.

Particular dosing regimens (e.g., dosing frequencies) for the IL-10 polypeptides are described elsewhere herein.

In certain embodiments, the dosage of the disclosed IL-10 polypeptide is contained in a "unit dosage form". The phrase "unit dosage form" refers to physically discrete units, each unit containing a predetermined amount of a IL-10 polypeptide of the present disclosure, either alone or in combination with one or more additional agents, sufficient to produce the desired effect. It will be appreciated that the parameters of a unit dosage form will depend on the particular agent and the effect to be achieved.

Kits

The present disclosure also contemplates kits comprising IL-10, and pharmaceutical compositions thereof. The kits are generally in the form of a physical structure housing various components, as described below, and may be utilized, for example, in practicing the methods described above (e.g., administration of a IL-10 polypeptide to a subject in need of restoring cholesterol homeostasis).

A kit can include one or more of the IL-10 polypeptides disclosed herein (provided in, e.g., a sterile container), which may be in the form of a pharmaceutical composition suitable for administration to a subject. The IL-10 polypeptides can be provided in a form that is ready for use or in a form requiring, for example, reconstitution or dilution prior to administration. When the IL-10 polypeptides are in a form that needs to be reconstituted by a user, the kit may also include buffers, pharmaceutically acceptable excipients, and the like, packaged with or separately from the IL-10 polypeptides. When combination therapy is contemplated, the kit may contain the several agents separately or they may already be combined in the kit. Each component of the kit may be enclosed within an individual container, and all of the various containers may be within a single package. A kit of the present disclosure may be designed for conditions necessary to properly maintain the components housed therein (e.g., refrigeration or freezing).

A kit may contain a label or packaging insert including identifying information for the components therein and instructions for their use (e.g., dosing parameters, clinical pharmacology of the active ingredient(s), including mechanism of action, pharmacokinetics and pharmacodynamics, adverse effects, contraindications, etc.). Labels or inserts can include manufacturer information such as lot numbers and expiration dates. The label or packaging insert may be, e.g., integrated into the physical structure housing the components, contained separately within the physical structure, or affixed to a component of the kit (e.g., an ampule, tube or vial).

Labels or inserts can additionally include, or be incorporated into, a computer readable medium, such as a disk (e.g., hard disk, card, memory disk), optical disk such as CD- or DVD-ROM/RAM, DVD, MP3, magnetic tape, or an electrical storage media such as RAM and ROM or hybrids of these such as magnetic/optical storage media, FLASH media or memory-type cards. In some embodiments, the actual instructions are not present in the kit, but means for obtaining the instructions from a remote source, e.g., via the internet, are provided.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below were performed and are all of the experiments that may be performed. It is to be understood that exemplary descriptions written in the present tense were not necessarily performed, but rather that the descriptions can be performed to generate the data and the like described therein. Efforts have been made to ensure accuracy with respect to numbers used (e.g., amounts, temperature, etc.), but some experimental errors and deviations should be accounted for.

Unless indicated otherwise, parts are parts by weight, molecular weight is weight average molecular weight, temperature is in degrees Celsius (° C.), and pressure is at or near atmospheric. Standard abbreviations are used, including the following: bp=base pair(s); kb=kilobase(s); pl=picoliter(s); s or sec=second(s); min=minute(s); h or hr=hour(s); aa=amino acid(s); kb=kilobase(s); nt=nucleotide(s); pg=picogram; ng=nanogram; μg=microgram; mg=milligram; g=gram; kg=kilogram; dl or dL=deciliter; μl or μL=microliter; ml or mL=milliliter; l or L=liter; μM=micromolar; mM=millimolar; M=molar; kDa=kilodalton; i.m.=intramuscular(ly); i.p.=intraperitoneal(ly); SC or SQ=subcutaneous(ly); QD=daily; BID=twice daily; QW=weekly; QM=monthly; HPLC=high performance liquid chromatography; BW=body weight; U=unit; ns=not statistically significant; PBS=phosphate-buffered saline; PCR=polymerase chain reaction; NHS=N-Hydroxysuccinimide; HSA=human serum albumin; MSA=mouse serum albumin; DMEM=Dulbeco's Modification of Eagle's Medium; GC=genome copy; EDTA=ethylenediaminetetraacetic acid; APOL8=Apolipoprotein L 8; APOA2=Apolipoprotein A-II; PCSK9=Proprotein convertase subtilisin/kexin type 9; CYP7A1=cytochrome P450 7A1, cholesterol 7 alpha-hydroxylase, or cholesterol 7-alpha-monooxygenase; ABCG1=ATP-binding cassette sub-family G member 1; CRP=C-reactive Protein; MSR1=Macrophage Scavenger Receptor 1.

Materials and Methods

The following general materials and methods were used, where indicated, or may be used in the Examples below:

Standard methods in molecular biology are described in the scientific literature (see, e.g., Sambrook and Russell (2001) Molecular Cloning, 3rd ed., Cold Spring Harbor Laboratory Press, Cold Spring Harbor, N.Y.; and Ausubel, et al. (2001) Current Protocols in Molecular Biology, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4)).

The scientific literature describes methods for protein purification, including immunoprecipitation, chromatography, electrophoresis, centrifugation, and crystallization, as well as chemical analysis, chemical modification, post-translational modification, production of fusion proteins, and glycosylation of proteins (see, e.g., Coligan, et al. (2000) Current Protocols in Protein Science, Vols. 1-2, John Wiley and Sons, Inc., NY).

Production, purification, and fragmentation of polyclonal and monoclonal antibodies are described (e.g., Harlow and Lane (1999) Using Antibodies, Cold Spring Harbor Laboratory Press, Cold Spring Harbor, N.Y.); standard techniques for characterizing ligand/receptor interactions are available (see, e.g., Coligan et al. (2001) Current Protocols in Immunology, Vol. 4, John Wiley, Inc., NY); methods for flow cytometry, including fluorescence-activated cell sorting (FACS), are available (see, e.g., Shapiro (2003) Practical Flow Cytometry, John Wiley and Sons, Hoboken, N.J.); and fluorescent reagents suitable for modifying nucleic acids, including nucleic acid primers and probes, polypeptides, and antibodies, for use, for example, as diagnostic reagents, are available (Molecular Probes (2003) Catalogue, Molecular Probes, Inc., Eugene, Oreg.; Sigma-Aldrich (2003) Catalogue, St. Louis, Mo.).

Software packages and databases for determining, e.g., antigenic fragments, leader sequences, protein folding, functional domains, glycosylation sites, and sequence alignments, are available (see, e.g., GCG Wisconsin Package (Accelrys, Inc., San Diego, Calif.); and DeCypher™ (TimeLogic Corp., Crystal Bay, Nev.).

Serum IL-10 concentration levels and exposure levels may be determined by standard methods used in the art. For example, a serum exposure level assay can be performed by collecting whole blood (~50 μl/mouse) from mouse tail snips into plain capillary tubes, separating serum and blood cells by centrifugation, and determining IL-10 exposure levels by standard ELISA kits and techniques.

LDLR−/− mice were obtained from The Jackson Lab (Bar Harbor, Me.). Such mice have an elevated serum cholesterol level of 200-400 mg/dl, and their cholesterol level exceeds >2,000 mg/dl when fed a high fat diet. Normal serum cholesterol in the mouse is 80-100 mg/dl.

Livers were excised from mice at necropsy and flash-frozen for subsequent analysis. Liver tissue was used in qPCR analysis via a standard Sybr Green protocol (see, e.g., Life Technologies Corp., Grand Island, N.Y.).

Normalized mRNA units were determined by relative quantification whereby changes in gene expression in a sample are calculated based on gene expression in a reference sample.

Cholesterol tests that directly measure LDL levels were used and are commercially available (e.g., Beckman Coulter, Inc; Brea, Calif.: AU System LDL-Cholesterol Test). Traditional tests (which generally use of a colorimetric assay system) for measuring total serum cholesterol are inexpensive and widely available (e.g., Sigma-Aldrich, St. Louis, Mo.; BioVision, Inc., Milpitas, Calif.).

A mono-/di-PEG-IL-10 mix described in the patent literature (e.g., US 2011/0250163) was used in the examples described below. Two exemplary synthetic schemes are as follows:

Exemplary Scheme No. 1

IL-10 (e.g., rodent or primate) is dialyzed against 50 mM sodium phosphate, 100 mM sodium chloride pH ranges 5-7.4. A 1:1-1:7 molar ratio of 5 kDa PEG-propyladehyde is reacted with IL-10 at a concentration of 1-12 mg/mL in the presence of 0.75-30 mM sodium cyanoborohydride. Alternatively the reaction can be activated with picoline borane in a similar manner. The reaction is incubated at 5-30° C. for 3-24 hours. The pH of the pegylation reaction is adjusted to 6.3, and 7.5 mg/mL of hIL-10 is reacted with PEG to make the ratio of IL-10 to PEG linker 1:3.5. The final concentration of cyanoborohydride is ~25 mM, and the reaction is carried out at 15° C. for 12-15 hours. The mono- and di-PEG IL-10 are the largest products of the reaction, with the concentration of each at ~50% at termination. The reaction may be quenched using an amino acid such as glycine or lysine or, alternatively, Tris buffers. Multiple purification methods can be employed such as gel filtration, anion and cation exchange chromatographies, and size exclusion HPLC (SE-HPLC) to isolate the desired pegylated IL-10 molecules.

Exemplary Scheme No. 2

IL-10 is dialyzed against 10 mM sodium phosphate pH 7.0, 100 mM NaCl. The dialyzed IL-10 is diluted 3.2 times to a concentration of about 0.5 to 12 mg/mL using the dialysis buffer. Prior to the addition of the linker, SC-PEG-12 kDa (Delmar Scientific Laboratories, Maywood, Ill.) and one volume of 100 mM Na-tetraborate at pH 9.1 is added into 9 volumes of the diluted IL-10 to raise the pH of the IL-10 solution to 8.6. The SC-PEG-12K linker is dissolved in the dialysis buffer and the appropriate volume of the linker solution (1.8 to 3.6 mole linker per mole of IL-10) is added into the diluted IL-10 solution to initiate the pegylation reaction. The reaction is carried out at 5° C. in order to control the rate, and the reaction solution is mildly agitated. When the mono-PEG-IL-10 yield, as determined by size exclusion HPLC (SE-HPLC), is close to 40%, the reaction is stopped by adding 1M glycine solution to a final concentration of 30 mM. The pH of the reaction solution is slowly adjusted to 7.0 using an HCl solution, and the reaction is 0.2 micron filtered and stored at −80° C.

PEG-IL-10 was formulated at 0.75-1.0 mg/mL in 10 mM HEPES, pH 6.5, 100 mM NaCl containing 0.05% MSA. Control (placebo)=same formulation matrix without PEG-IL-10.

Immunohistochemistry

Picosirius Red Stain:

Slides were heated in an oven at 60° C. for 45 mins; deparaffinized using xylene and a series of alcohols; rehydrated in water; kept for 60 mins in freshly prepared Picosirius red solution according to manufacturer's instructions; and subjected to two washes in acidified water. Nuclei were stained with Weigert's hematoxylin for 8-10 mins, dehydrated in three changes of 100% ethanol, cleared, and mounted.

Anti-F4/80, Anti-Msr1, PCNA and Sca1:

Liver tissues were fixed with 10% neutral-buffered formaldehyde and were embedded in paraffin. Tissue specimens were cut into 5 μm-thick sections, deparaffinized in xylene sections, and hydrated in a graded series of alcohol solutions (100%, 95%, 80%, 70%, 50%; 3 changes, 5 mins each). The tissues on slides underwent heat-induced epitope retrieval (10 mmol/L sodium citrate buffer at 98° C. for 20 mins), then treated with 3% $H_2O_2$ to quench endogenous peroxidase. Sections were incubated in blocking solution (5% neutral goat serum) for 1 hour at rt. Primary antibodies of choice were applied to the slides and incubated in a humid chamber overnight at 4° C. Secondary biotinylated antibody was then applied at 1:250 dilution (Vector Lab; Burlingame, Calif.), followed by incubation with streptavidin peroxidase. Sections were washed with PBS 3× after each step. Sections were stained with DAB substrate and counterstained with Mayer's hematoxylin for 2 mins. Slides were dehydrated in three changes of 100% ethanol, cleared, and mounted.

Image Quantitation:

For analysis of PEG-rMuIL-10-treated livers compared to vehicle-treated livers, 2-5 mice per group were randomly selected and stained with Sirius Red (Polyscience Inc.; Warrington, Pa.), anti-PCNA (Abcam; Cambridge, Mass.), Hematoxylin (American MasterTech; Lodi, Calif.), anti-Msr1 (Abcam), anti-F4/80 (Abcam), and Sca1 (Abcam). For each liver, 8-10 independent images were collected using the 20× objective. An average area of signal was then analyzed using MetaMorph Imaging Software (Molecular Devices; Sunnyvale, Calif.) by applying a color threshold on a representative field and adjusting the pixel distribution to correspond with a positive signal. All images were taken with a 20× objective.

Bars in the figures represent the median of the datapoints.

Example 1

Effect of PEG-IL-10 on Lipid Panel

The effect of PEG-rmIL-10 exposure on lipid panel-associated parameters was determined in LDLR−/− mice fed a high fat diet. Four groups (10 mice/group) were administered 1 mg/kg, 0.2 mg/kg, or 0.02 mg/kg of PEG-rmIL-10 or vehicle control SC daily for 14 days, after which total serum cholesterol, triglycerides, LDL, HDL, and the LDL/HDL ratio were determined.

Referring to FIG. 2, levels of cholesterol (FIG. 2A); triglycerides (FIG. 2B); and LDL (FIG. 2C) were all significantly reduced at each dose of PEG-rmIL-10 compared to vehicle. More particularly, relative to vehicle control, 1 mg/kg, 0.2 mg/kg, and 0.02 mg/kg PEG-rmIL-10 reduced total serum cholesterol by approximately 68%, 67% and 45%, respectively (FIG. 2A); reduced serum triglycerides by approximately 53%, 61% and 51%, respectively (FIG. 2B); and reduced serum LDL by approximately 75%, 75% and 49%, respectively (FIG. 2C).

Interestingly, the reductions of total serum cholesterol and serum LDL are essentially the same in the groups of animals receiving 1 mg/kg PEG-rmIL-10 and 0.2 mg/kg PEG-rmIL-10. Although an understanding of why this effect occurred is not necessary in order to practice the present disclosure, it is believed to be due to internalization of cholesterol into micelles above a particular IL-10 serum concentration; thus, when comparing the two doses, there is nominal incremental cholesterol and LDL lowering. These dose-escalation results suggest that it is possible to achieve therapeutically relevant reductions in cholesterol, triglycerides and LDL at a pegylated IL-10 dose lower than that which might be associated with severe untoward adverse effects.

Figure 2E:
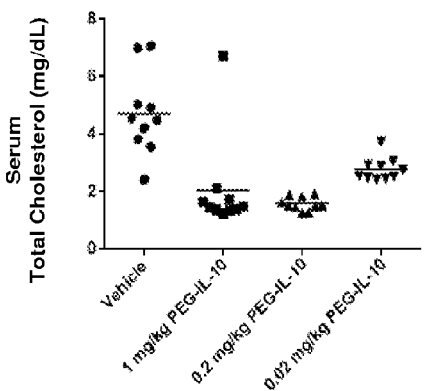

As indicated in FIG. 2D, when compared to vehicle control, increasing doses of PEG-rmIL-10 resulted in decreasing levels of HDL (0.02 mg/kg=15%; 0.2 mg/kg=26%; and 1 mg/kg=32%). The smaller HDL reduction between the 0.2 mg/kg and 1 mg/kg doses than that between the 0.02 mg/kg and 0.2 mg/kg doses is likely due, at least in part, to the same micellular explanation as set forth above. As discussed previously, reduction of HDL (the so called "good cholesterol") might be viewed as unfavorable; however, key opinion leaders have suggested that the detrimental effect of decreases in HDL is likely of more import in subjects having very high cholesterol levels. Referring to FIG. 2E, compared to vehicle control, LDL/HDL ratios were reduced by 41% (0.02 mg/kg), 66% (0.2 mg/kg), and 56% (1 mg/kg). As a larger ratio reduction is preferred, these data demonstrate that the 0.2 mg/kg dose of PEG-rmIL-10 is more beneficial than the 1 mg/kg dose.

Taken together, these data indicate that it is not necessary to exceed an approximately 0.2 mg/kg dose of PEG-IL-10 in mice in order to achieve an optimal therapeutic effect. Thus, the more serious adverse effects (e.g., liver toxicity) observed with higher doses can be avoided. Translation of the murine dose to the human dose should lead to comparable results.

Example 2

Effect of PEG-IL-10 on Regulators of Cholesterol Synthesis

In order to evaluate the mechanism of action of PEG-rmIL-10 in cholesterol synthesis, LDLR−/− mice were fed a high-fat Western diet for four weeks. During weeks three and four, mice were administered PEG-rmIL-10 (1 mg/kg; 0.2 mg/kg; or 0.02 mg/kg) or vehicle control (10 mice in each of the four groups) SC daily, after which livers were analyzed for expression of a panel of genes involved in the cholesterol synthesis pathway (Mevalonate Pathway).

The expression levels of the following hepatic enzymes were down-regulated, relative to HMG-CoA Reductase used as a control, by at least two-fold (data not shown): HMG-CoA Synthase; Phosphomevalonate Kinase; Farnysyl Diphosphate Synthase; and NAD(P)-Dependent Steroid Dehydrogenase. The expression levels of the other hepatic enzymes that were evaluated exhibited changes that were less than the two-fold threshold (data not shown).

These results demonstrate that IL-10 impacts multiple enzymatic steps in the cholesterol synthesis pathway.

Example 3

Effect of PEG-IL-10 on Cholesterol Regulators

In order to evaluate the effects of PEG-rmIL-10 on regulators of bile acid synthesis (CYP7A1); intracellular cholesterol trafficking (APOL8); and cholesterol efflux (ABCG1), LDLR−/− mice were fed a high-fat Western diet for four weeks. During weeks three and four, mice were administered PEG-rmIL-10 (1 mg/kg; 0.2 mg/kg; or 0.02 mg/kg) or vehicle control (10 mice in each of the four groups) SC daily, after which message expression in liver of CYP7A1, APOL8 and ABCG1 was evaluated.

CYP7A1, a cytochrome P450 heme enzyme that oxidizes cholesterol, is the rate-limiting enzyme in the synthesis of bile acid from cholesterol, catalyzing the formation of 7-alpha-hydroxycholesterol. CYP7A1 is sometimes referred to as the bile acid synthase gene. CYP7A1 is down-regulated by Sterol Regulatory Element-binding Proteins (SREBP) when plasma cholesterol levels are low. Conversely, it is up-regulated by the nuclear receptor LXR (Liver X Receptor) when cholesterol (more specifically, oxysterol) levels are high, and this up-regulation increases the production of bile acids and reduces the level of cholesterol in hepatocytes. As indicated in FIG. 3A, 0.2 mg/kg and 0.02 mg/kg PEG-rmIL-10 increased message expression of CYP7A1, indicating that there is increased efflux of cholesterol from the liver.

Interestingly, the 1.0 mg/kg dose of PEG-rmIL-10 essentially had no effect on message expression of CYP7A1. One possible explanation for this result relates to the interplay between IL-1b and IL-10 on CYP7A1. It has been reported that IL-1b can decrease expression levels of CYP7A1 in the liver (see Feingold et al, J. Lipid Res. (1996) 37:223-28). When high doses of PEG-IL-10 are administered in order to combat high serum cholesterol concentrations, IL-1b expression is dramatically enhanced. The high levels of IL-1b mRNA and (likely) protein is thought to feed back to limit the expression of CYP7A1, resulting in little, if any, effect on cholesterol efflux.

APOL8 belongs to the HDL family and plays a central role in cholesterol transport. Increasing doses of PEG-rmIL-10 correlated with increasing message expression of APOL8 (FIG. 3B), resulting in greater intracellular cholesterol trafficking and thus more substrate available for efflux.

Figure 3C:
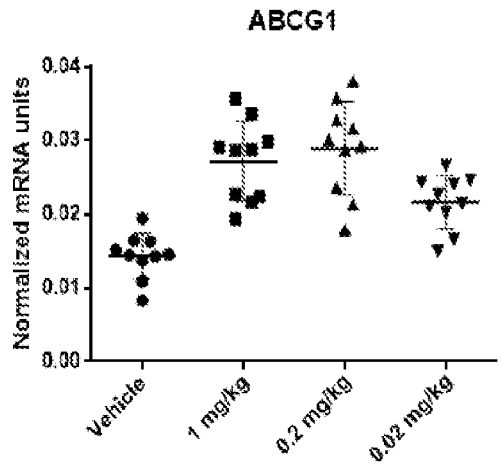

FIG. 3C depicts the effect of PEG-rmIL-10 on ABCG1, which is involved in macrophage cholesterol and phospholipids transport, and may regulate cellular lipid homeostasis in other cell types. ABCG1 is an efflux molecule involved in preparing cholesterol for removal from the liver as bile salts. The data in FIG. 3C indicate that higher doses of PEG-rmIL-10 are associated with increases in ABCG1 message expression, which, in turn, correlates with a reduction in serum cholesterol.

Example 4

Effect of PEG-IL-10 on LDL and HDL Regulation

In order to evaluate the effects of PEG-rmIL-10 on regulators of LDL (PCSK9) and HDL (APOA2), LDLR−/− mice were fed a high-fat Western diet for four weeks. During weeks three and four, mice were administered PEG-rmIL-10 (1 mg/kg; 0.2 mg/kg; or 0.02 mg/kg) or vehicle control (10 mice in each of the four groups) SC daily, after which message expression in liver of PCSK9 and APOA2 was evaluated.

PCSK9 plays a major regulatory role in cholesterol homeostasis. As discussed herein, LDL cholesterol is removed from the blood when it binds to LDL receptors (LDLR) on the surface of liver cells, and is taken up by the cells. PCSK9 binds to the epidermal growth factor-like repeat A (EGF-A) domain of the LDLR, inducing LDLR degradation which, in turn, decreases metabolism of LDL, resulting in hypercholesterolemia. Thus, if PCSK9 does not bind, the receptor can return to the surface of the cell and remove more cholesterol. Agents that block PCSK9 can lower cholesterol and are being developed. As indicated in FIG. 4A, PEG-rmIL-10 down-regulates message expression of PCSK9. As the knock-out mice lack the LDL receptor, these data indicate that PEG-IL-10 dramatically lowers cholesterol in a non-PCSK9-dependent manner (i.e., pegylated IL-10's reduction in cholesterol is independent of regulation of PCSK9).

Figure 4B:
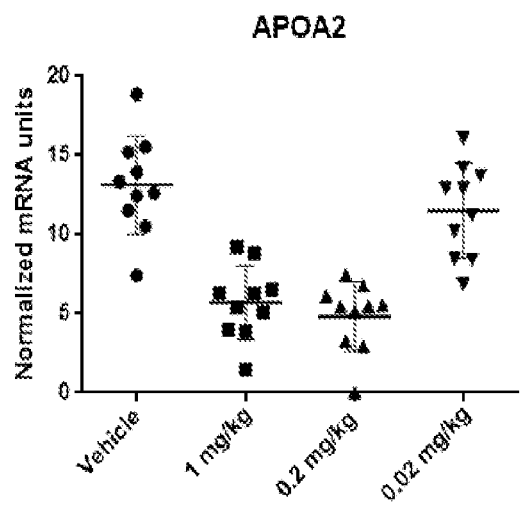

Administration of PEG-rmIL-10 to knockout mice also causes a reduction in the message expression of the HDL particle protein APOA2 (FIG. 4B). APOA2, which is involved in HDL construction, is the second most abundant protein of the high density lipoprotein particles. Thus, the reduction of APOA2 message expression that results from administration of PEG-IL-10 contributes to hypercholesterolemia through reduction of HDL. However, as discussed elsewhere herein, the beneficial effects of pegylated IL-10 on LDL vastly outweigh any less favorable effects due to HDL reduction; this may be especially true when pegylated IL-10 is administered in combination with another agent(s) having a different mechanism of action.

Example 5

Effect of PEG-IL-10 on Regulator of Inflammation

In order to evaluate the effect of PEG-rmIL-10 on regulation of CRP, LDLR−/− mice were fed a high-fat Western diet for four weeks. During weeks three and four, mice were administered PEG-rmIL-10 (1 mg/kg; 0.2 mg/kg; or 0.02 mg/kg) or vehicle control (10 mice in each of the four groups) SC daily, after which message expression in liver of CRP was evaluated.

CRP is a member of the class of acute-phase reactants, as its levels rise dramatically during inflammatory processes occurring in the body. It is thought to assist in complement binding to foreign and damaged cells and enhances phagocytosis by macrophages, which express a receptor for CRP. CRP is also believed to play a role in innate immunity as an early defense system against infections. High levels of CRP have been associated with cardiovascular risk, largely due to its inflammatory and atherosclerotic effects. Therefore, the reduction of CRP message expression seen with pegylated IL-10 administration (FIG. 5) is suggestive of its cardioprotective effect.

Example 6

Effect of PEG-IL-10 on Regulators of Cholesterol Uptake

In order to evaluate the effect of PEG-rmIL-10 on MSR1 and MARCO, regulators of cholesterol uptake, LDLR−/− mice were fed a high-fat Western diet for four weeks. During weeks three and four, mice were administered PEG-rmIL-10 (1 mg/kg; 0.2 mg/kg; or 0.02 mg/kg) or vehicle control (10 mice in each of the four groups) SC daily, after which message expression in livers of MSR1 and MARCO was evaluated.

MSR1, also known as SR-A1 (Scavenger Receptor-A1) and CD204 (Cluster of Differentiation 204), and MARCO, a macrophage receptor also known as SR-A2 (Scavenger Receptor A-2), are scavenger receptors that mediate the endocytosis of LDLs and are thus involved in cholesterol uptake. Increased message expression of both scavenger receptors—MSR1 (FIG. 6A) and MARCO (FIG. 6B)—was observed following administration of pegylated IL-10. As such increased expression correlates with enhanced cholesterol uptake, MSR1 and MARCO are associated with normalizing hypercholesterolemia.

Example 7

Effect of Phagocytotic Cell Depletion on PEG-rMuIL-10-Induced Reduction of Cholesterol The nexus between phagocytotic cells within the myeloid lineage and PEG-rMuIL-10's control of plasma cholesterol was evaluated. Standard techniques were used for removing phagocytotic cells by dosing animals with clodronate liposomes in the presence or absence of PEG-rMuIL-10. Initially, complete depletion of phagocytotic cells in the liver was confirmed by detection with IHC of F4/80. Hepatocyte health was confirmed by TUNEL IHC (no increase in apoptotic cells; data not shown) and H&E (no change in the histological morphology or cellular organization; data not shown) to ensure that hepatocytes were not affected by clodronate.

Wild-type and LDLR−/− C57BL/6 mice (7-8 weeks old) were maintained on normal chow or were fed a high-fat Western diet for 2 weeks prior to dosing. PEG-rMuIL-10 (1 mg/kg) or vehicle (10 mM HEPES, 100 mM NaCl, pH 6.5, 0.05% mouse serum albumin) were dosed subcutaneously daily for 1 to 2 weeks. Mice were maintained on their respective diets throughout dosing. For clodronate depletion studies, mice were dosed IV with clodronate liposomes (5 mg/mL clodronate; Cl) or vehicle liposomes (Li) suspended in 1×PBS, every three days (first dose: 0.2 mL, subsequent doses: 0.1 mL), starting one day before PEG-rMuIL-10 dosing.

Figure 7:
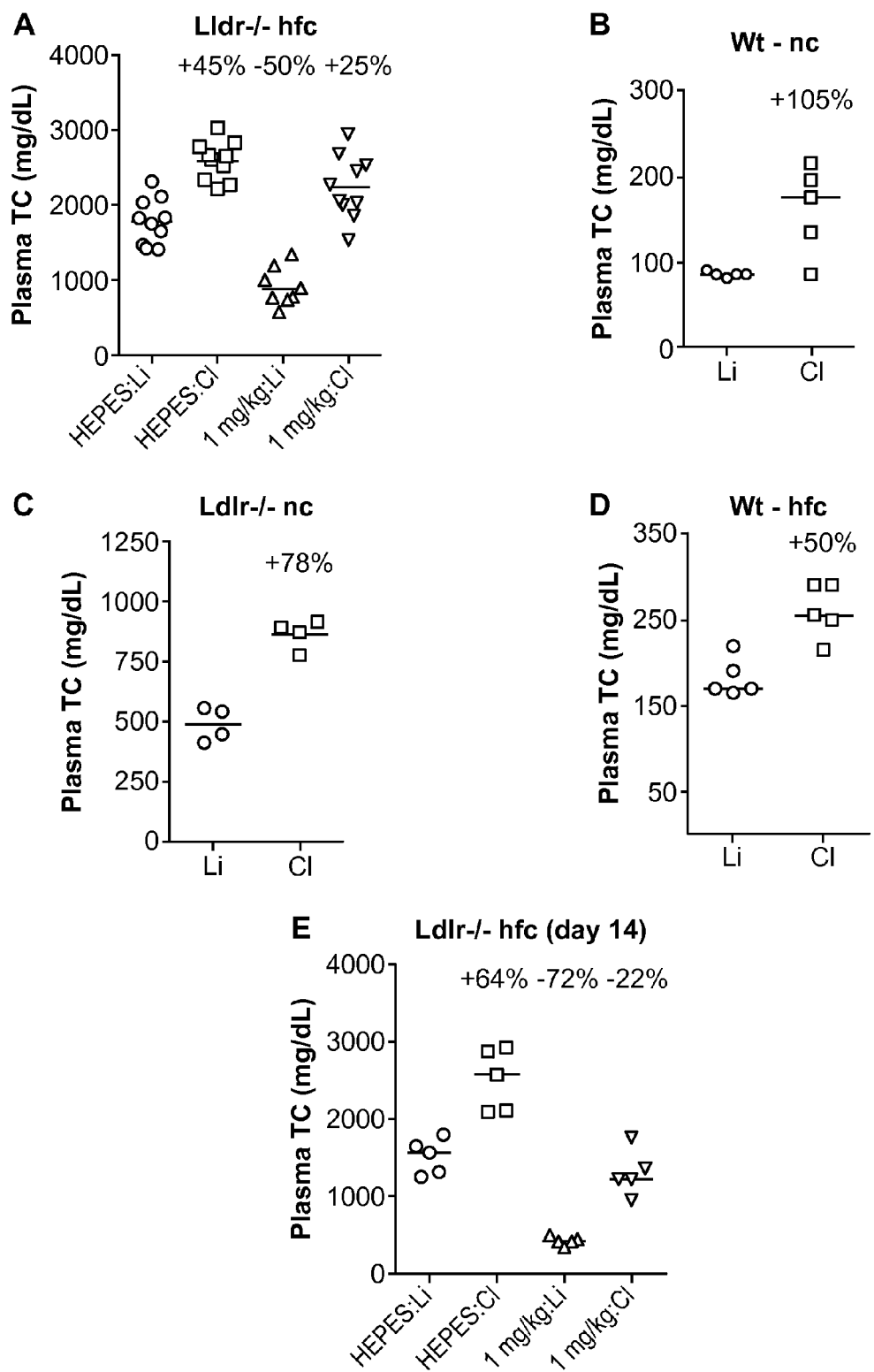
FIG. 7 (Panels A-E) depicts the effect that depletion of phagocytotic cells has on PEG-rMuIL-10-induced cholesterol reduction in LDLR−/− mice and wild-type mice fed a high-fat diet (FIG. 7, Panels A, D and E) and in LDLR−/− mice and wild-type mice fed a normal diet (FIGS. 7C and 7B).

FIG. 7, Panel A depicts the total plasma cholesterol in LDLR−/− mice fed a high-fat diet after 7 days treatment with HEPES/liposomes, HEPES/clodronate, PEG-rMuIL-10/liposomes, and PEG-rMuIL-10/clodronate. FIG. 7, Panel D depicts the total plasma cholesterol in wild-type mice fed a high-fat diet treated with liposomes or clodronate for 24 hours. FIG. 7, Panel C depicts the total plasma cholesterol in LDLR−/− mice fed normal chow treated with liposomes or clodronate for 24 hours. FIG. 7, Panel B depicts the total plasma cholesterol in wild-type mice treated with liposomes or clodronate for 24 hours. FIG. 7, Panel E depicts total plasma cholesterol after 14 days treatment of the mice used to generate the data in FIG. 7, Panel A.

Referring to FIG. 7, Panel A, depletion of phagocytotic cells abolished PEG-rMuIL-10's regulation of plasma cholesterol. Unexpectedly, the clodronate alone caused a 45% increase in total plasma cholesterol. Depletion of phagocytotic cells in wild-type and LDLR−/− mice on normal chow diet (FIG. 7, Panels B and C) and wild-type mice on high-fat diet (FIG. 7, Panel D) resulted in consistently increased plasma cholesterol, suggesting phagocytotic cells are involved in the normal regulation of plasma cholesterol. FIG. 7, Panel E shows that the repopulation of liver Kupffer cells is concomitant with a decrease in plasma cholesterol. Moreover, PEG-rMuIL-10 dosing appeared to accelerate the rate at which the Kupffer cells repopulated the tissue.

Example 8

Effect of PEG-rHuIL-10 on Myeloid Lineage Cell Scavenging

Human peripheral monocytes, human peripheral macrophages, human Kupffer cells and human hepatocytes were treated with PEG-rHuIL-10 in vitro in order to determine which hepatic cells respond to PEG-rHuIL-10.

Figure 8:
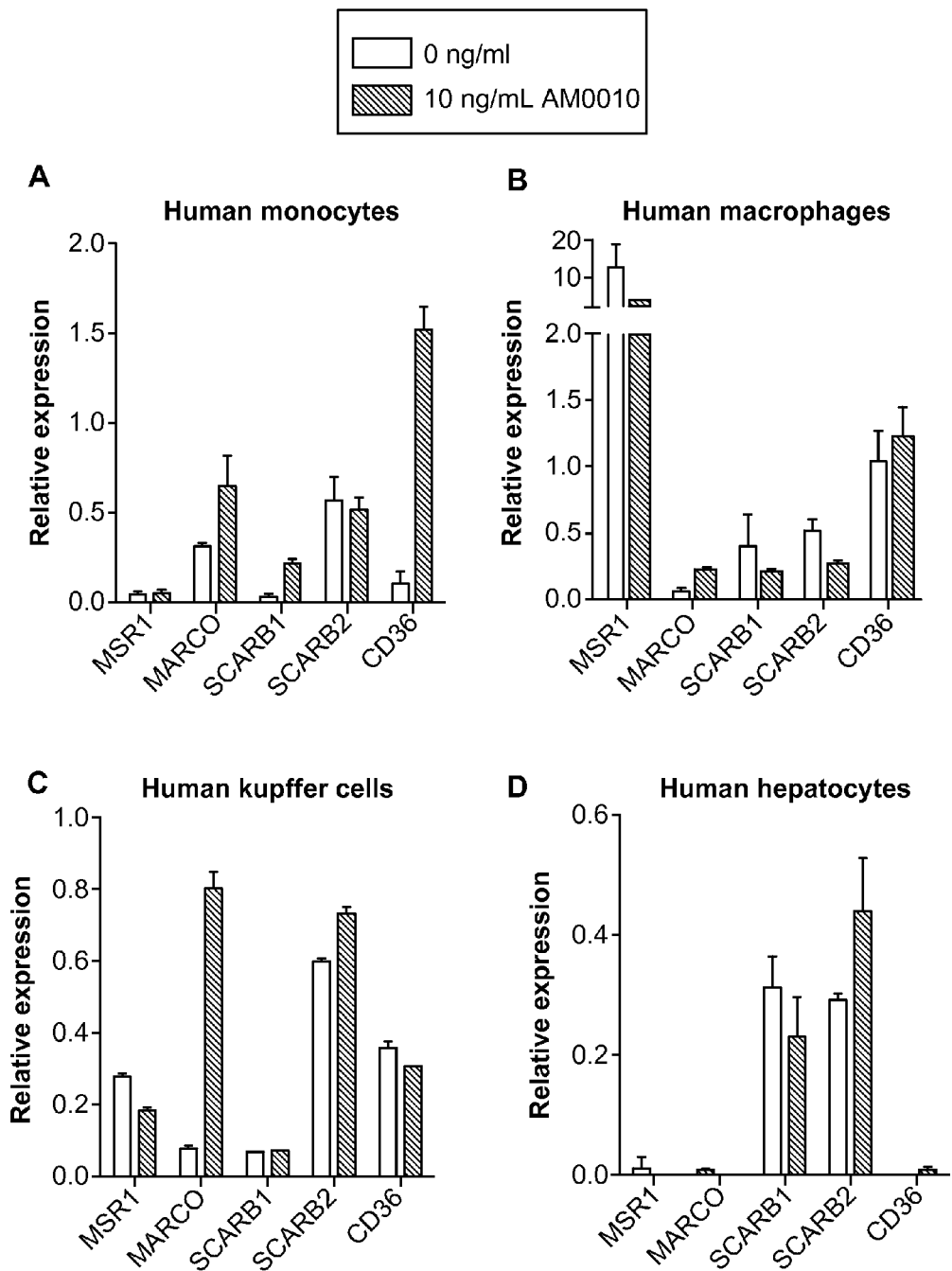
FIG. 8 (Panels A-J) depicts whether human monocytes, macrophages, Kupffer cells or hepatocytes treated with PEG-rHuIL-10 in vitro respond to PEG-rHuIL-10.

Referring to FIG. 8, Panels A-D, $1\times10^5$-$1\times10^6$ cells were analyzed for their expression of MSR1, MARCO, SCARB1, SCARB2, and CD36 after 24 hours exposure to 10 ng/mL PEG-rHuIL-10. FIG. 8, Panels A-D depicts scavenger receptor expression analysis of human peripheral monocytes (FIG. 8, Panel A), human peripheral macrophages (FIG. 8, Panel B), human Kupffer cells (FIG. 8, Panel C), and human hepatocytes (FIG. 8, Panel D). The data in FIG. 8, Panels A-D represent three independent experiments. Scavenger receptor expression was only enhanced on Kupffer cells and peripheral monocytes (see FIG. 8, Panels A-D). Peripheral monocytes differentiated to macrophages when exposed to 50 ng/mL M-CSF for 7 days in cRPMI media. Scavenger receptor regulation appeared to be similar between mice and humans (data not shown), suggesting a conservation of IL-10's biology with regard to effects on the myeloid compartment.

A determination was then made as to whether increased expression of scavenger receptors correlates with enhanced uptake of lipoproteins. Referring to FIG. 8, Panels E-H, cells were exposed to control (w/o) and PEG-rHuIL-10 (10 ng/mL) for 24 hours, with total uptake assessed after 4-5 hours. The data in FIG. 8, Panels E-H represent 3-10 independent experiments. Background (b.g.) mean fluorescence intensity (M.F.I.) from cells not exposed to any form of LDL is also indicated. [*p<0.05, ***p<0.001]. FIG. 8, Panels E-H depict quantitation of LDL, Ac-LDL and Ox-LDL uptake in human monocytes (FIG. 8, Panel E), human macrophages (FIG. 8, Panel F), human Kupffer cells (FIG. 8, Panel G), and human hepatocytes (FIG. 8, Panel H). As indicated in FIG. 8E, PEG-rHuIL-10 increased the uptake of Ac and Ox-LDL, but not LDL, by freshly isolated peripheral blood monocytes. Referring to FIG. 8, Panel F, M-CSF-differentiated macrophages did not respond to PEG-rHuIL-10, whereas PEG-rHuIL-10 increased Kupffer cell uptake of LDL but not Ac-LDL or Ox-LDL (FIG. 8, Panel G). Hepatocyte uptake of LDL, Ox-LDL and Ac-LDL was unchanged in response to PEG-rHuIL-10 (FIG. 8, Panel H). Although myeloid lineage cells are generally phagocytic, these data indicate that the nature of cholesterol uptake is different between monocytes, macrophages, Kupffer cells and hepatocytes in response to PEG-rHuIL-10.

FIG. 8, Panels I and J depict the inhibitory effect of mannose on uptake of Ac-LDL (FIG. 8, Panel I) and Ox-LDL (FIG. 8, Panel J). Cells were pre-exposed to 100 mM mannose prior to co-incubation with Ox-LDL and Ac-LDL. Cells were exposed to control (w/o) and PEG-rHuIL-10 (10 ng/mL) for 24 hours, with total uptake assessed after 4-5 hours. The data in FIGS. 8I and J represent 3-10 independent experiments. Background (b.g.) mean fluorescence intensity (M.F.I.) from cells not exposed to any form of LDL is also indicated. [*p<0.05, ***p<0.001]. Referring to FIGS. 8I and J, mannose inhibited PEG-rHuIL-10's increase in Ac-LDL, but not Ox-LDL uptake by monocytes. These data suggest that PEG-rHuIL-10's control of lipoprotein uptake is via both known and possibly unknown scavenger receptor regulation.

Example 9

Regulation of Cholesterol in Cancer Patients

Total plasma cholesterol was measured in cancer patients treated with PEG-rHuIL-10. Fully consented patients were subjected to weekly peripheral blood collection by trained phlebotomists under IRB approved protocol; FDA study ID# NCT02009449. Serum cholesterol quantitation was performed by local clinical laboratories following standard procedures.

Figure 9:
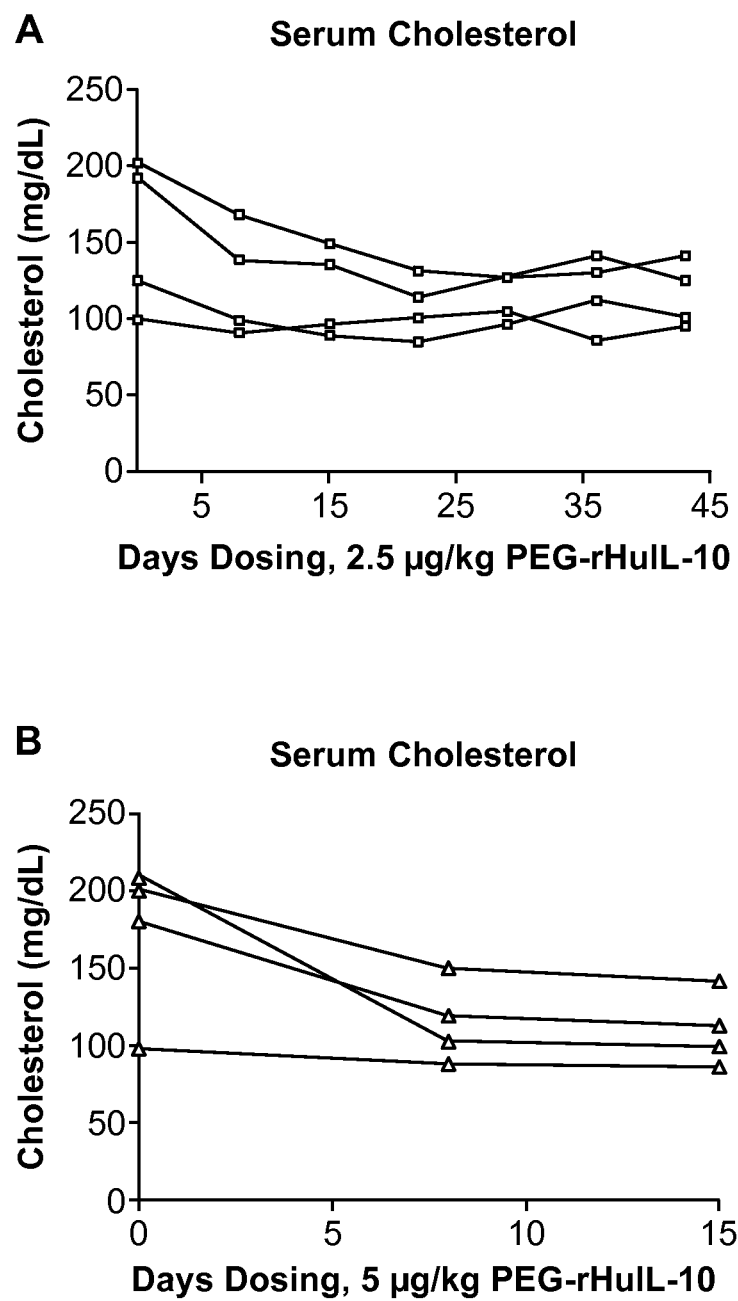
FIG. 9 (Panels A and B) depicts the effect of PEG-rHuIL-10 in cancer patients with low and elevated plasma cholesterol levels.

Patients were trained to self-inject PEG-rHuIL-10 abdominally. PEG-rHuIL-10 was administered to patients at either 2.5 µg/kg (n=4) or 5 µg/kg (n=4) SC daily. Patients were dosed for 15 to 28 days. Referring to FIGS. 9A and 9B, PEG-rHuIL-10 did not affect patients with low plasma cholesterol (~100 mg/dL), while patients with an initial plasma cholesterol of approximately 140 mg/dL exhibited a decrease in plasma cholesterol to about 100 mg/dL following PEG-rHuIL-10 administration. A level of 140 mg/dL or below is consistent with no lifetime risk of a cardiovascular event. Each line on the graphs in FIGS. 9A and B represents an individual patient.

These data indicate that PEG-rHuIL-10 regulates cholesterol only in hypercholesterolemic patients.

Particular embodiments of this invention are described herein, including the best mode known to the inventors for carrying out the invention. Upon reading the foregoing, description, variations of the disclosed embodiments may become apparent to individuals working in the art, and it is expected that those skilled artisans may employ such variations as appropriate. Accordingly, it is intended that the invention be practiced otherwise than as specifically described herein, and that the invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All publications, patent applications, accession numbers, and other references cited in this specification are herein incorporated by reference as if each individual publication or patent application were specifically and individually indicated to be incorporated by reference.

What is claimed is:

1. A method of treating hyperlipidemia in a subject suffering therefrom, said method comprising administering to the subject a therapeutically effective amount of a PEG-IL-10 agent, wherein the amount is sufficient to maintain an IL-10 serum trough concentration of 1.0 pg/mL to 10.0 ng/mL over a period of time of at least 24 hours.

2. The method of claim 1, wherein the IL-10 serum trough concentration is in the range of from 1.0 pg/mL to 1.0 ng/mL.

3. The method of claim 1, wherein the PEG-IL-10 agent comprises mature human IL-10.

4. The method of claim 1, wherein the PEG-IL-10 agent comprises a variant of mature human IL-10, and wherein the variant exhibits activity comparable to the activity of mature human IL-10.

5. The method of claim 1, wherein the disease is hypercholesterolemia.

6. The method of claim 1, wherein the PEG-IL-10 agent comprises at least one PEG molecule covalently attached to at least one amino acid residue of at least one subunit of mature human IL-10.

7. The method of claim 1, wherein the PEG-IL-10 agent comprises a mixture of mono-pegylated and di-pegylated IL-10.

8. The method of claim 1, wherein the PEG component of the PEG-IL-10 agent has a molecular mass from about 5 kDa to about 20 kDa.

9. The method of claim 1, wherein the PEG component of the PEG-IL-10 agent has a molecular mass greater than about 20 kDa.

10. The method of claim 6, wherein at least one PEG molecule is covalently attached to the at least one IL-10 subunit via a linker.

11. The method of claim 1, wherein the PEG-IL-10 agent is administered to the subject at least once daily.

12. The method of claim 1, wherein the method comprises administering at least one additional prophylactic or therapeutic agent.

13. The method of claim 1, wherein the subject is a human.

14. The method of claim 1, wherein the administering is by parenteral injection.

15. The method of claim 14, wherein the parenteral injection is subcutaneous.

* * * * *

UNITED STATES PATENT AND TRADEMARK OFFICE
CERTIFICATE OF CORRECTION

PATENT NO. : 10,010,588 B2
APPLICATION NO. : 14/908992
DATED : July 3, 2018
INVENTOR(S) : John Brian Mumm et al.

It is certified that error appears in the above-identified patent and that said Letters Patent is hereby corrected as shown below:

On the Title Page

Column 2 (Other Publications), Line 5, please delete "/lwww." and insert -- //www. --, therefor.

Column 2 (Other Publications), Line 6, please delete "/recom bi nant-" and insert -- /recombinant- --, therefor.

Column 2 (Other Publications), Line 6, please delete "-1O-" and insert -- -10- --, therefor.

Column 2 (Other Publications), Line 8, please delete "/lwww." and insert -- //www. --, therefor.

Column 2 (Other Publications), Line 9, please delete "/recom bi nant-" and insert -- /recombinant- --, therefor.

Signed and Sealed this
Thirtieth Day of April, 2019

Andrei Iancu
*Director of the United States Patent and Trademark Office*

SEQUENCE LISTING

```
<160> NUMBER OF SEQ ID NOS: 24

<210> SEQ ID NO 1
<211> LENGTH: 178
<212> TYPE: PRT
<213> ORGANISM: Homo sapiens

<400> SEQUENCE: 1

Met His Ser Ser Ala Leu Leu Cys Cys Leu Val Leu Leu Thr Gly Val
1               5                   10                  15

Arg Ala Ser Pro Gly Gln Gly Thr Gln Ser Glu Asn Ser Cys Thr His
            20                  25                  30

Phe Pro Gly Asn Leu Pro Asn Met Leu Arg Asp Leu Arg Asp Ala Phe
        35                  40                  45

Ser Arg Val Lys Thr Phe Phe Gln Met Lys Asp Gln Leu Asp Asn Leu
    50                  55                  60

Leu Leu Lys Glu Ser Leu Leu Glu Asp Phe Lys Gly Tyr Leu Gly Cys
65                  70                  75                  80

Gln Ala Leu Ser Glu Met Ile Gln Phe Tyr Leu Glu Glu Val Met Pro
                85                  90                  95

Gln Ala Glu Asn Gln Asp Pro Asp Ile Lys Ala His Val Asn Ser Leu
            100                 105                 110

Gly Glu Asn Leu Lys Thr Leu Arg Leu Arg Leu Arg Arg Cys His Arg
        115                 120                 125

Phe Leu Pro Cys Glu Asn Lys Ser Lys Ala Val Glu Gln Val Lys Asn
    130                 135                 140

Ala Phe Asn Lys Leu Gln Glu Lys Gly Ile Tyr Lys Ala Met Ser Glu
145                 150                 155                 160

Phe Asp Ile Phe Ile Asn Tyr Ile Glu Ala Tyr Met Thr Met Lys Ile
                165                 170                 175

Arg Asn
```

```
<210> SEQ ID NO 2
<211> LENGTH: 178
<212> TYPE: PRT
<213> ORGANISM: Mus musculus

<400> SEQUENCE: 2

Met Pro Gly Ser Ala Leu Leu Cys Cys Leu Leu Leu Thr Gly Met
1               5                   10                  15

Arg Ile Ser Arg Gly Gln Tyr Ser Arg Glu Asp Asn Cys Thr His
            20                  25                  30

Phe Pro Val Gly Gln Ser His Met Leu Leu Glu Leu Arg Thr Ala Phe
            35                  40                  45

Ser Gln Val Lys Thr Phe Phe Gln Thr Lys Asp Gln Leu Asp Asn Ile
    50                  55                  60

Leu Leu Thr Asp Ser Leu Met Gln Asp Phe Lys Gly Tyr Leu Gly Cys
65                  70                  75                  80

Gln Ala Leu Ser Glu Met Ile Gln Phe Tyr Leu Val Glu Val Met Pro
                85                  90                  95

Gln Ala Glu Lys His Gly Pro Glu Ile Lys Glu His Leu Asn Ser Leu
                100                 105                 110

Gly Glu Lys Leu Lys Thr Leu Arg Met Arg Leu Arg Arg Cys His Arg
            115                 120                 125

Phe Leu Pro Cys Glu Asn Lys Ser Lys Ala Val Glu Gln Val Lys Ser
130                 135                 140

Asp Phe Asn Lys Leu Gln Asp Gln Gly Val Tyr Lys Ala Met Asn Glu
145                 150                 155                 160

Phe Asp Ile Phe Ile Asn Cys Ile Glu Ala Tyr Met Met Ile Lys Met
                165                 170                 175

Lys Ser

<210> SEQ ID NO 3
<211> LENGTH: 11
<212> TYPE: PRT
<213> ORGANISM: Human immunodeficiency virus type 1

<400> SEQUENCE: 3

Tyr Gly Arg Lys Lys Arg Arg Gln Arg Arg Arg
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Synthetic polypeptide

<400> SEQUENCE: 4

Arg Arg Gln Arg Arg Thr Ser Lys Leu Met Lys Arg
1               5                   10

<210> SEQ ID NO 5
<211> LENGTH: 27
<212> TYPE: PRT
<213> ORGANISM: Artificial Sequence
<220> FEATURE:
<223> OTHER INFORMATION: Synthetic polypeptide

<400> SEQUENCE: 5

Gly Trp Thr Leu Asn Ser Ala Gly Tyr Leu Leu Gly Lys Ile Asn Leu
1               5                   10                  15
```

-continued

Lys Ala Leu Ala Ala Leu Ala Lys Lys Ile Leu
            20                  25

<210> SEQ ID NO 6
<211> LENGTH: 33
<212> TYPE: PRT
<213> ORGANISM: Artificial Sequence
<220> FEATURE:
<223> OTHER INFORMATION: Synthetic polypeptide

<400> SEQUENCE: 6

Lys Ala Leu Ala Trp Glu Ala Lys Leu Ala Lys Ala Leu Ala Lys Ala
1               5                   10                  15

Leu Ala Lys His Leu Ala Lys Ala Leu Ala Lys Ala Leu Lys Cys Glu
            20                  25                  30

Ala

<210> SEQ ID NO 7
<211> LENGTH: 16
<212> TYPE: PRT
<213> ORGANISM: Artificial Sequence
<220> FEATURE:
<223> OTHER INFORMATION: Synthetic polypeptide

<400> SEQUENCE: 7

Arg Gln Ile Lys Ile Trp Phe Gln Asn Arg Arg Met Lys Trp Lys Lys
1               5                   10                  15

<210> SEQ ID NO 8
<211> LENGTH: 9
<212> TYPE: PRT
<213> ORGANISM: Artificial Sequence
<220> FEATURE:
<223> OTHER INFORMATION: Synthetic polypeptide

<400> SEQUENCE: 8

Arg Lys Lys Arg Arg Gln Arg Arg Arg
1               5

<210> SEQ ID NO 9
<211> LENGTH: 8
<212> TYPE: PRT
<213> ORGANISM: Artificial Sequence
<220> FEATURE:
<223> OTHER INFORMATION: Synthetic polypeptide

<400> SEQUENCE: 9

Arg Lys Lys Arg Arg Gln Arg Arg
1               5

<210> SEQ ID NO 10
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 10

Tyr Ala Arg Ala Ala Ala Arg Gln Ala Arg Ala
1               5                   10

<210> SEQ ID NO 11
<211> LENGTH: 11
<212> TYPE: PRT
<213> ORGANISM: Artificial Sequence
<220> FEATURE:

<223> OTHER INFORMATION: Synthetic polypeptide

<400> SEQUENCE: 11

Thr His Arg Leu Pro Arg Arg Arg Arg Arg
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic polypeptide

<400> SEQUENCE: 12

Gly Gly Arg Arg Ala Arg Arg Arg Arg Arg
1               5                   10

<210> SEQ ID NO 13
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (5)..(5)
<223> OTHER INFORMATION: S at position 5 may occur n times, where n is
      an integer of at least one.

<400> SEQUENCE: 13

Gly Ser Gly Gly Ser
1               5

<210> SEQ ID NO 14
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (4)..(4)
<223> OTHER INFORMATION: S at position 4 may occur n times, where n is
      an integer of at least one.

<400> SEQUENCE: 14

Gly Gly Gly Ser
1

<210> SEQ ID NO 15
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(1)
<223> OTHER INFORMATION: G at position 1 may occur m times, where m is
      an integer of at least one.
<220> FEATURE:
<221> NAME/KEY: REPEAT
<222> LOCATION: (1)..(5)
<223> OTHER INFORMATION: Positions 1 to 5 may occur n times, where n is
      an integer of at least one.
<220> FEATURE:
<221> NAME/KEY: REPEAT
<222> LOCATION: (2)..(2)
<223> OTHER INFORMATION: S at position 2 may occur o times, where o is
      an integer of at least one.
<220> FEATURE:

```
<221> NAME/KEY: REPEAT
<222> LOCATION: (3)..(3)
<223> OTHER INFORMATION: G at position 3 may occur m times, where m is
      an integer of at least one.
<220> FEATURE:
<221> NAME/KEY: REPEAT
<222> LOCATION: (4)..(4)
<223> OTHER INFORMATION: S at position 4 may occur o times, where o is
      an integer of at least one.
<220> FEATURE:
<221> NAME/KEY: REPEAT
<222> LOCATION: (5)..(5)
<223> OTHER INFORMATION: G at position 5 may occur m times, where m is
      an integer of at least one.

<400> SEQUENCE: 15

Gly Ser Gly Ser Gly
1               5

<210> SEQ ID NO 16
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(5)
<223> OTHER INFORMATION: Positions 1 to 5 may occur n times, where n is
      an integer of at least one.
<220> FEATURE:
<221> NAME/KEY: REPEAT
<222> LOCATION: (5)..(5)
<223> OTHER INFORMATION: S at position 5 may occur m times, where m is
      an integer of at least one.

<400> SEQUENCE: 16

Gly Ser Gly Gly Ser
1               5

<210> SEQ ID NO 17
<211> LENGTH: 5
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(5)
<223> OTHER INFORMATION: Positions 1 to 5 may occur n times, where n is
      an integer of at least one.
<220> FEATURE:
<221> NAME/KEY: REPEAT
<222> LOCATION: (4)..(4)
<223> OTHER INFORMATION: S at position 4 may occur m times, where m is
      an integer of at least one.

<400> SEQUENCE: 17

Gly Ser Gly Ser Gly
1               5

<210> SEQ ID NO 18
<211> LENGTH: 4
<212> TYPE: PRT
<213> ORGANISM: Artificial Sequence
<220> FEATURE:
<223> OTHER INFORMATION: Synthetic polypeptide
<220> FEATURE:
<221> NAME/KEY: REPEAT
<222> LOCATION: (1)..(4)
<223> OTHER INFORMATION: Positions 1 to 4 may occur n times, where n is
      an integer of at least one.
<220> FEATURE:
```

```
<221> NAME/KEY: REPEAT
<222> LOCATION: (4)..(4)
<223> OTHER INFORMATION: S at position 4 may occur m times, where m is
      an integer of at least one.

<400> SEQUENCE: 18

Gly Gly Gly Ser
1

<210> SEQ ID NO 19
<211> LENGTH: 4
<212> TYPE: PRT
<213> ORGANISM: Artificial Sequence
<220> FEATURE:
<223> OTHER INFORMATION: Synthetic polypeptide

<400> SEQUENCE: 19

Gly Gly Ser Gly
1

<210> SEQ ID NO 20
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 20

Gly Gly Ser Gly Gly
1               5

<210> SEQ ID NO 21
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 21

Gly Ser Gly Ser Gly
1               5

<210> SEQ ID NO 22
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 22

Gly Ser Gly Gly Gly
1               5

<210> SEQ ID NO 23
<211> LENGTH: 5
<212> TYPE: PRT
<213> ORGANISM: Artificial Sequence
<220> FEATURE:
<223> OTHER INFORMATION: Synthetic polypeptide

<400> SEQUENCE: 23

Gly Gly Gly Ser Gly
1               5

<210> SEQ ID NO 24
<211> LENGTH: 5
<212> TYPE: PRT
```

```
<213> ORGANISM: Artificial Sequence
<220> FEATURE:
<223> OTHER INFORMATION: Synthetic polypeptide

<400> SEQUENCE: 24

Gly Ser Ser Ser Gly
1               5
```